United States Patent
Joseph et al.

(10) Patent No.: US 12,295,692 B2
(45) Date of Patent: May 13, 2025

(54) STEERABLE CATHETER WITH SHAFT LOAD DISTRIBUTIONS

(71) Applicant: Auris Health, Inc., Redwood City, CA (US)

(72) Inventors: Miles Joseph, San Jose, CA (US); Francis Macnamara, Mountain View, CA (US)

(73) Assignee: Auris Health, Inc., Santa Clara, CA (US)

( * ) Notice: Subject to any disclaimer, the term of this patent is extended or adjusted under 35 U.S.C. 154(b) by 0 days.

(21) Appl. No.: 18/200,620

(22) Filed: May 23, 2023

(65) Prior Publication Data

US 2024/0000533 A1    Jan. 4, 2024

Related U.S. Application Data

(60) Continuation of application No. 16/588,890, filed on Sep. 30, 2019, now Pat. No. 11,701,192, which is a
(Continued)

(51) Int. Cl.
*A61B 34/00* (2016.01)
*A61B 34/30* (2016.01)
(Continued)

(52) U.S. Cl.
CPC ............. *A61B 34/71* (2016.02); *A61B 34/30* (2016.02); *A61M 25/0147* (2013.01);
(Continued)

(58) Field of Classification Search
CPC ........ A61B 2034/301; A61B 2034/715; A61B 34/30; A61B 34/37; A61B 34/71; A61M 2025/015; A61M 25/0147
See application file for complete search history.

(56) References Cited

U.S. PATENT DOCUMENTS 3,572,325 A    3/1971    Bazell et al.
3,913,565 A    10/1975    Kawahara
(Continued)

FOREIGN PATENT DOCUMENTS

CA    2285342    10/1998
CN    1846181    10/2006
(Continued)

OTHER PUBLICATIONS

Camarillo et al., "Mechanics Modeling of Tendon-Driven Continuum Manipulators," IEEE Transaction on Robotics, Dec. 2008, pp. 1262-1273, vol. 24 No. 6.
(Continued)

*Primary Examiner* — Scott Luan
(74) *Attorney, Agent, or Firm* — Frost Brown Todd LLP

(57) ABSTRACT

A steerable catheter system may include a flexible elongate catheter body, a drive mechanism at the proximal end of the catheter body, and at least one group of pullwires extending along a length of the catheter body. The catheter body may include a distal articulating section and a proximal non-articulating section. Each group of pullwires includes at least two pullwires, and each of the pullwires is anchored at a first end to the distal end of the catheter body and at a second end to the drive mechanism. The pullwires of each group are positioned close to one another in the catheter wall to concentrate the forces and cause deflection along the articulating section of the catheter body and diverge away from one another to reach a more separated distribution around a circumference of the catheter body to distribute the forces and prevent deflection along the non-articulating section.

20 Claims, 46 Drawing Sheets

Related U.S. Application Data division of application No. 15/248,316, filed on Aug. 26, 2016, now Pat. No. 10,463,439.

(51) Int. Cl.
*A61M 25/01* (2006.01)
*A61B 34/37* (2016.01)

(52) U.S. Cl.
CPC ......... *A61B 2034/301* (2016.02); *A61B 34/37* (2016.02); *A61B 2034/715* (2016.02); *A61M 2025/015* (2013.01)

(56) References Cited

U.S. PATENT DOCUMENTS

| | | | |
|---|---|---|---|
| 4,294,234 A | 10/1981 | Matsuo | |
| 4,392,485 A | 7/1983 | Hiltebrandt | |
| 4,607,619 A | 8/1986 | Seike et al. | |
| 4,690,175 A | 9/1987 | Ouchi et al. | |
| 4,706,656 A | 11/1987 | Kubota | |
| 4,741,326 A | 5/1988 | Sidall et al. | |
| 4,745,908 A | 5/1988 | Wardle | |
| 4,748,969 A | 6/1988 | Wardle | |
| 4,750,475 A | 6/1988 | Yoshihashi | |
| 4,771,766 A | 9/1988 | Aoshiro | |
| 4,846,791 A | 7/1989 | Hattler et al. | |
| 4,869,238 A | 9/1989 | Opie et al. | |
| 4,906,496 A | 3/1990 | Hosono et al. | |
| 4,907,168 A | 3/1990 | Boggs | |
| 4,925,445 A | 5/1990 | Sakamoto et al. | |
| 4,945,305 A | 7/1990 | Blood | |
| 4,967,732 A | 11/1990 | Inoue | |
| 4,976,812 A | 12/1990 | McConnell et al. | |
| 5,003,982 A | 4/1991 | Halperin | |
| 5,050,585 A | 9/1991 | Takahashi | |
| 5,060,632 A | 10/1991 | Hibino et al. | |
| 5,067,346 A | 11/1991 | Field | |
| 5,078,714 A | 1/1992 | Katims | |
| 5,083,549 A | 1/1992 | Cho et al. | |
| 5,106,387 A | 4/1992 | Kittrell et al. | |
| 5,108,800 A | 4/1992 | Koo | |
| 5,125,909 A | 6/1992 | Heimberger | |
| 5,146,835 A | 9/1992 | McConnell et al. | |
| 5,168,864 A | 12/1992 | Shockey | |
| 5,217,002 A | 6/1993 | Katsurada | |
| 5,251,611 A | 10/1993 | Zehel et al. | |
| 5,257,617 A | 11/1993 | Takahashi | |
| 5,261,391 A | 11/1993 | Inoue | |
| 5,287,861 A | 2/1994 | Wilk | |
| 5,313,934 A | 5/1994 | Wiita et al. | |
| 5,320,696 A | 6/1994 | McConnell et al. | |
| 5,339,799 A | 8/1994 | Kami et al. | |
| 5,341,807 A | 8/1994 | Nardella | |
| 5,368,015 A | 11/1994 | Wilk | |
| 5,386,818 A | 2/1995 | Schneebaum | |
| 5,394,875 A | 3/1995 | Lewis et al. | |
| 5,397,443 A | 3/1995 | Michaels | |
| 5,398,691 A | 3/1995 | Martin et al. | |
| 5,408,409 A | 4/1995 | Glassman et al. | |
| 5,433,215 A | 7/1995 | Athanasiou et al. | |
| 5,447,529 A | 9/1995 | Marchlinski et al. | |
| 5,448,988 A | 9/1995 | Watanabe | |
| 5,469,857 A | 11/1995 | Laurent et al. | |
| 5,477,856 A | 12/1995 | Lundquist | |
| 5,478,330 A | 12/1995 | Imran et al. | |
| 5,482,029 A | 1/1996 | Sekiguchi | |
| 5,489,270 A | 2/1996 | van Erp | |
| 5,492,131 A | 2/1996 | Galel | |
| 5,507,725 A | 4/1996 | Savage et al. | |
| 5,524,635 A | 6/1996 | Uflacker et al. | |
| 5,533,985 A | 7/1996 | Wang | |
| 5,580,200 A | 12/1996 | Fullerton | |
| 5,600,330 A | 2/1997 | Blood | |
| 5,631,973 A | 5/1997 | Green | |
| 5,662,108 A | 9/1997 | Budd et al. | |
| 5,673,704 A | 10/1997 | Marchlinski et al. | |
| 5,681,296 A | 10/1997 | Ishida | |
| 5,697,377 A | 12/1997 | Wittkampf | |
| 5,704,534 A | 1/1998 | Huitema et al. | |
| 5,713,946 A | 2/1998 | Ben-Haim | |
| 5,720,775 A | 2/1998 | Lamard | |
| 5,722,959 A | 3/1998 | Bierman | |
| 5,738,096 A | 4/1998 | Ben-Haim | |
| 5,741,429 A | 4/1998 | Donadio, III | |
| 5,749,362 A | 5/1998 | Funda et al. | |
| 5,749,889 A | 5/1998 | Bacich et al. | |
| 5,754,741 A | 5/1998 | Wang et al. | |
| 5,762,458 A | 6/1998 | Wang et al. | |
| 5,784,542 A | 7/1998 | Ohm et al. | |
| 5,799,055 A | 8/1998 | Peshkin et al. | |
| 5,810,716 A | 9/1998 | Mukherjee et al. | |
| 5,815,640 A | 9/1998 | Wang et al. | |
| 5,825,982 A | 10/1998 | Wright et al. | |
| 5,833,608 A | 11/1998 | Acker | |
| 5,836,869 A | 11/1998 | Kudo et al. | |
| 5,836,874 A | 11/1998 | Swanson et al. | |
| 5,836,990 A | 11/1998 | Li | |
| 5,843,076 A | 12/1998 | Webster, Jr. et al. | |
| 5,845,646 A | 12/1998 | Lemelson | |
| 5,873,817 A | 2/1999 | Kokish et al. | |
| 5,876,325 A | 3/1999 | Mizuno et al. | |
| 5,878,193 A | 3/1999 | Wang et al. | |
| 5,879,287 A | 3/1999 | Yoshihashi | |
| 5,882,347 A | 3/1999 | Mouris-Laan | |
| 5,888,191 A | 3/1999 | Akiba | |
| 5,891,095 A | 4/1999 | Eggers et al. | |
| 5,910,129 A | 6/1999 | Koblish et al. | |
| 5,911,694 A | 6/1999 | Ikeda et al. | |
| 5,925,078 A | 7/1999 | Anderson | |
| 5,935,079 A | 8/1999 | Swanson et al. | |
| 5,938,586 A | 8/1999 | Wilk | |
| 5,938,587 A | 8/1999 | Taylor et al. | |
| 5,950,629 A | 9/1999 | Taylor et al. | |
| 5,953,683 A | 9/1999 | Hansen et al. | |
| 5,983,126 A | 11/1999 | Wittkampf | |
| 6,004,271 A | 12/1999 | Moore | |
| 6,012,494 A | 1/2000 | Balazs | |
| 6,061,587 A | 5/2000 | Kucharczyk et al. | |
| 6,063,022 A | 5/2000 | Ben-Haim | |
| 6,063,095 A | 5/2000 | Wang et al. | |
| 6,068,604 A | 5/2000 | Krause et al. | |
| 6,080,181 A | 6/2000 | Jensen et al. | |
| 6,083,170 A | 7/2000 | Ben-Haim | |
| 6,096,004 A | 8/2000 | Meglan et al. | |
| 6,102,850 A | 8/2000 | Wang et al. | |
| 6,106,511 A | 8/2000 | Jensen | |
| 6,126,651 A | 10/2000 | Mayer | |
| 6,129,668 A | 10/2000 | Haynor et al. | |
| 6,132,368 A | 10/2000 | Cooper | |
| 6,143,013 A | 11/2000 | Samson et al. | |
| 6,157,853 A | 12/2000 | Blume et al. | |
| 6,161,032 A | 12/2000 | Acker | |
| 6,172,499 B1 | 1/2001 | Ashe | |
| 6,174,280 B1 | 1/2001 | Oneda | |
| 6,197,015 B1 | 3/2001 | Wilson | |
| 6,198,974 B1 | 3/2001 | Webster, Jr. | |
| 6,203,493 B1 | 3/2001 | Ben-Haim | |
| 6,226,543 B1 | 5/2001 | Gilboa et al. | |
| 6,228,028 B1 | 5/2001 | Klein et al. | |
| 6,233,476 B1 | 5/2001 | Strommer et al. | |
| 6,233,504 B1 | 5/2001 | Das et al. | |
| 6,234,958 B1 | 5/2001 | Snoke et al. | |
| 6,246,200 B1 | 6/2001 | Blumenkranz et al. | |
| 6,266,551 B1 | 7/2001 | Osadchy et al. | |
| 6,272,371 B1 | 8/2001 | Shlomo | |
| 6,301,496 B1 | 10/2001 | Reisfeld | |
| 6,309,397 B1 | 10/2001 | Julian et al. | |
| 6,310,828 B1 | 10/2001 | Mumm et al. | |
| 6,312,435 B1 | 11/2001 | Wallace et al. | |
| 6,314,856 B1 | 11/2001 | Keith et al. | |
| 6,315,715 B1 | 11/2001 | Taylor et al. | |
| 6,331,181 B1 | 12/2001 | Tierney et al. | |
| 6,363,279 B1 | 3/2002 | Ben-Haim et al. | |
| 6,370,411 B1 | 4/2002 | Osadchy et al. | |

(56) References Cited

U.S. PATENT DOCUMENTS

| | | |
|---|---|---|
| 6,371,952 B1 | 4/2002 | Madhani et al. |
| 6,375,471 B1 | 4/2002 | Wendlandt et al. |
| 6,380,732 B1 | 4/2002 | Gilboa |
| 6,384,483 B1 | 5/2002 | Igarashi et al. |
| 6,393,340 B2 | 5/2002 | Funda et al. |
| 6,398,731 B1 | 6/2002 | Mumm et al. |
| 6,400,979 B1 | 6/2002 | Stoianovici et al. |
| 6,404,497 B1 | 6/2002 | Backman |
| 6,415,171 B1 | 7/2002 | Gueziec et al. |
| 6,424,885 B1 | 7/2002 | Niemeyer et al. |
| 6,436,107 B1 | 8/2002 | Wang et al. |
| 6,464,632 B1 | 10/2002 | Taylor |
| 6,485,411 B1 | 11/2002 | Konstorum |
| 6,491,626 B1 | 12/2002 | Stone et al. |
| 6,491,701 B2 | 12/2002 | Tierney et al. |
| 6,493,573 B1 | 12/2002 | Martinelli et al. |
| 6,493,608 B1 | 12/2002 | Niemeyer |
| 6,526,859 B1 | 3/2003 | Ozawa et al. |
| 6,530,913 B1 | 3/2003 | Giba et al. |
| 6,537,205 B1 | 3/2003 | Smith |
| 6,544,230 B1 | 4/2003 | Flaherty |
| 6,551,273 B1 | 4/2003 | Olson et al. |
| 6,554,793 B1 | 4/2003 | Pauker et al. |
| 6,565,554 B1 | 5/2003 | Niemeyer |
| 6,569,084 B1 | 5/2003 | Mizuno et al. |
| 6,574,355 B2 | 6/2003 | Green |
| 6,580,938 B1 | 6/2003 | Acker |
| 6,587,750 B2 | 7/2003 | Gerbi et al. |
| 6,594,552 B1 | 7/2003 | Nowlin |
| 6,610,007 B2 | 8/2003 | Belson et al. |
| 6,615,155 B2 | 9/2003 | Gilboa |
| 6,618,612 B1 | 9/2003 | Acker et al. |
| 6,620,173 B2 | 9/2003 | Gerbi et al. |
| 6,626,899 B2 | 9/2003 | Houser et al. |
| 6,629,534 B1 | 10/2003 | St. Goar et al. |
| 6,659,939 B2 | 12/2003 | Moll et al. |
| 6,669,709 B1 | 12/2003 | Cohn |
| 6,679,152 B1 | 1/2004 | Head et al. |
| 6,685,698 B2 | 2/2004 | Morley et al. |
| 6,699,235 B2 | 3/2004 | Wallace et al. |
| 6,716,166 B2 | 4/2004 | Govari |
| 6,716,178 B1 | 4/2004 | Kilpatrick et al. |
| 6,726,675 B1 | 4/2004 | Beyar |
| 6,741,883 B2 | 5/2004 | Gildenberg |
| 6,746,422 B1 | 6/2004 | Noriega |
| 6,749,560 B1 | 6/2004 | Konstorum |
| 6,774,624 B2 | 8/2004 | Anderson et al. |
| 6,786,896 B1 | 9/2004 | Madhani et al. |
| 6,790,173 B2 | 9/2004 | Saadat |
| 6,799,065 B1 | 9/2004 | Niemeyer |
| 6,817,973 B2 | 11/2004 | Merril et al. |
| 6,817,974 B2 | 11/2004 | Cooper et al. |
| 6,827,710 B1 | 12/2004 | Mooney et al. |
| 6,827,712 B2 | 12/2004 | Tovey et al. |
| 6,837,846 B2 | 1/2005 | Jaffe |
| 6,852,107 B2 | 2/2005 | Wang et al. |
| 6,858,003 B2 | 2/2005 | Evans et al. |
| 6,905,460 B2 | 6/2005 | Wang et al. |
| 6,908,428 B2 | 6/2005 | Aizenfeld |
| 6,921,362 B2 | 7/2005 | Ouchi |
| 6,958,035 B2 | 10/2005 | Friedman et al. |
| 6,963,792 B1 | 11/2005 | Green |
| 7,008,401 B2 | 3/2006 | Thompson et al. |
| 7,021,173 B2 | 4/2006 | Stoianovici et al. |
| 7,074,179 B2 | 7/2006 | Wang et al. |
| 7,087,049 B2 | 8/2006 | Nowlin et al. |
| 7,090,683 B2 | 8/2006 | Brock et al. |
| 7,130,700 B2 | 10/2006 | Gardeski et al. |
| 7,169,141 B2 | 1/2007 | Brock et al. |
| 7,192,438 B2 | 3/2007 | Margolis |
| 7,225,012 B1 | 5/2007 | Susil et al. |
| 7,280,863 B2 | 10/2007 | Shachar |
| 7,297,142 B2 | 11/2007 | Brock |
| 7,320,700 B2 | 1/2008 | Cooper et al. |
| 7,331,967 B2 | 2/2008 | Lee et al. |
| 7,343,195 B2 | 3/2008 | Strommer et al. |
| 7,371,210 B2 | 5/2008 | Brock |
| 7,404,824 B1 | 7/2008 | Webler et al. |
| 7,494,494 B2 | 2/2009 | Stoianovici et al. |
| 7,540,866 B2 | 6/2009 | Viswanathan et al. |
| 7,569,052 B2 | 8/2009 | Phan et al. |
| 7,594,903 B2 | 9/2009 | Webler et al. |
| 7,645,230 B2 | 1/2010 | Mikkaichi |
| 7,645,231 B2 | 1/2010 | Akiba |
| 7,789,827 B2 | 9/2010 | Landry |
| 7,850,642 B2 | 12/2010 | Moll et al. |
| 7,930,065 B2 | 4/2011 | Larkin et al. |
| 7,963,288 B2 | 6/2011 | Rosenberg et al. |
| 8,046,049 B2 | 10/2011 | Govari et al. |
| 8,052,636 B2 | 11/2011 | Moll et al. |
| 8,092,397 B2 | 1/2012 | Wallace et al. |
| 8,122,809 B2 | 2/2012 | Simpson |
| 8,190,238 B2 | 5/2012 | Moll et al. |
| 8,210,085 B2 | 7/2012 | Lindh et al. |
| 8,219,178 B2 | 7/2012 | Smith et al. |
| 8,246,536 B2 | 8/2012 | Ochi |
| 8,261,648 B1 | 9/2012 | Marchand et al. |
| 8,444,637 B2 | 5/2013 | Podmore et al. |
| 8,460,236 B2 | 6/2013 | Roelle et al. |
| 8,498,691 B2 | 7/2013 | Moll et al. |
| 8,515,215 B2 | 8/2013 | Younge et al. |
| 8,652,030 B2 | 2/2014 | Matsuura et al. |
| 8,671,817 B1 | 3/2014 | Bogusky |
| 8,686,747 B2 | 4/2014 | Berner |
| 8,758,231 B2 | 6/2014 | Bunch et al. |
| 8,827,947 B2 | 9/2014 | Bosman et al. |
| 8,827,948 B2 | 9/2014 | Romo et al. |
| 8,894,610 B2 | 11/2014 | MacNamara et al. |
| 9,138,166 B2 | 9/2015 | Wong et al. |
| 9,173,713 B2 | 11/2015 | Hart et al. |
| 9,186,046 B2 | 11/2015 | Ramamurthy et al. |
| 9,504,604 B2 | 1/2016 | Alvarez |
| 9,254,123 B2 | 2/2016 | Alvarez et al. |
| 9,314,953 B2 | 4/2016 | Lauer |
| 9,427,551 B2 | 8/2016 | Leeflang et al. |
| 9,561,083 B2 | 2/2017 | Yu et al. |
| 9,591,990 B2 | 3/2017 | Chen et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,130,427 B2 | 11/2018 | Tanner et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |

(56) References Cited

U.S. PATENT DOCUMENTS

| | | |
|---|---|---|
| 10,314,463 B2 | 6/2019 | Agrawal et al. |
| 10,363,103 B2 | 7/2019 | Alvarez et al. |
| 10,376,672 B2 | 8/2019 | Yu |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,463,439 B2 | 11/2019 | Joseph et al. |
| 10,470,830 B2 | 11/2019 | Hill |
| 10,482,599 B2 | 11/2019 | Mintz et al. |
| 10,517,692 B2 | 12/2019 | Eyre et al. |
| 10,524,866 B2 | 1/2020 | Srinivasan |
| 10,543,048 B2 | 1/2020 | Noonan et al. |
| 10,639,114 B2 | 5/2020 | Schuh |
| 10,667,875 B2 | 6/2020 | DeFonzo |
| 10,716,637 B2 * | 7/2020 | Kowshik ............... A61B 34/35 |
| 10,743,751 B2 | 8/2020 | Landey et al. |
| 10,751,140 B2 | 8/2020 | Wallace et al. |
| 10,765,303 B2 | 9/2020 | Graetzel et al. |
| 10,765,487 B2 | 9/2020 | Ho |
| 11,701,192 B2 | 7/2023 | Joseph et al. |
| 2001/0004676 A1 | 6/2001 | Ouchi |
| 2001/0009976 A1 | 7/2001 | Panescu et al. |
| 2001/0029366 A1 | 10/2001 | Swanson et al. |
| 2002/0087169 A1 | 7/2002 | Brock et al. |
| 2002/0133174 A1 | 9/2002 | Charles et al. |
| 2002/0138009 A1 | 9/2002 | Brockway et al. |
| 2002/0156369 A1 | 10/2002 | Chakeres |
| 2002/0177789 A1 | 11/2002 | Ferry et al. |
| 2003/0036748 A1 | 2/2003 | Cooper et al. |
| 2003/0050649 A1 | 3/2003 | Brock et al. |
| 2003/0055360 A1 | 3/2003 | Zeleznik et al. |
| 2003/0060927 A1 | 3/2003 | Gerbi et al. |
| 2003/0073908 A1 | 4/2003 | Desai |
| 2003/0074011 A1 | 4/2003 | Gilboa et al. |
| 2003/0109780 A1 | 6/2003 | Coste-Maniere et al. |
| 2003/0130564 A1 | 7/2003 | Martone et al. |
| 2003/0135204 A1 | 7/2003 | Lee et al. |
| 2003/0158545 A1 | 8/2003 | Hovda et al. |
| 2003/0163199 A1 | 8/2003 | Chu et al. |
| 2003/0195664 A1 | 10/2003 | Nowlin et al. |
| 2004/0015122 A1 | 1/2004 | Zhang et al. |
| 2004/0034282 A1 | 2/2004 | Quaid, III |
| 2004/0034365 A1 | 2/2004 | Lentz et al. |
| 2004/0054322 A1 | 3/2004 | Vargas |
| 2004/0072066 A1 | 4/2004 | Cho et al. |
| 2004/0138525 A1 | 7/2004 | Saadat et al. |
| 2004/0152972 A1 | 8/2004 | Hunter |
| 2004/0171929 A1 | 9/2004 | Leitner et al. |
| 2004/0176751 A1 | 9/2004 | Weitzner et al. |
| 2004/0193013 A1 | 9/2004 | Isakawa et al. |
| 2004/0193146 A1 | 9/2004 | Lee et al. |
| 2004/0220588 A1 | 11/2004 | Kermode et al. |
| 2004/0249246 A1 | 12/2004 | Campos |
| 2005/0004515 A1 | 1/2005 | Hart et al. |
| 2005/0027397 A1 | 2/2005 | Niemeyer |
| 2005/0059960 A1 | 3/2005 | Simaan et al. |
| 2005/0070844 A1 | 3/2005 | Chow et al. |
| 2005/0085728 A1 | 4/2005 | Fukuda |
| 2005/0125005 A1 | 6/2005 | Fujikura |
| 2005/0131279 A1 | 6/2005 | Boulais et al. |
| 2005/0131460 A1 | 6/2005 | Gifford, III et al. |
| 2005/0154262 A1 | 7/2005 | Banik et al. |
| 2005/0159646 A1 | 7/2005 | Nordstrom et al. |
| 2005/0159789 A1 | 7/2005 | Brockway et al. |
| 2005/0165276 A1 | 7/2005 | Belson et al. |
| 2005/0165366 A1 | 7/2005 | Brustad |
| 2005/0182295 A1 | 8/2005 | Soper et al. |
| 2005/0182330 A1 | 8/2005 | Brockway et al. |
| 2005/0200324 A1 | 9/2005 | Guthart et al. |
| 2005/0203382 A1 | 9/2005 | Govari et al. |
| 2005/0222554 A1 | 10/2005 | Wallace et al. |
| 2005/0222581 A1 | 10/2005 | Fischer et al. |
| 2005/0234293 A1 | 10/2005 | Yamamoto |
| 2005/0256452 A1 | 11/2005 | DeMarchi |
| 2005/0272975 A1 | 12/2005 | McWeeney et al. |
| 2005/0273085 A1 | 12/2005 | Hinman et al. |
| 2005/0288549 A1 | 12/2005 | Mathis |
| 2006/0013523 A1 | 1/2006 | Childers et al. |
| 2006/0025679 A1 | 2/2006 | Viswanathan et al. |
| 2006/0041188 A1 | 2/2006 | Dirusso et al. |
| 2006/0058647 A1 | 3/2006 | Strommer et al. |
| 2006/0111692 A1 | 5/2006 | Hlavka et al. |
| 2006/0161045 A1 | 7/2006 | Merril et al. |
| 2006/0178556 A1 | 8/2006 | Nasser et al. |
| 2006/0241368 A1 | 10/2006 | Fichtinger et al. |
| 2006/0264708 A1 | 11/2006 | Horne |
| 2006/0271036 A1 | 11/2006 | Garabedian et al. |
| 2006/0276827 A1 | 12/2006 | Mitelberg et al. |
| 2006/0293864 A1 | 12/2006 | Soss |
| 2007/0016130 A1 | 1/2007 | Leeflang et al. |
| 2007/0038181 A1 | 2/2007 | Melamud et al. |
| 2007/0060847 A1 | 3/2007 | Leo et al. |
| 2007/0060879 A1 | 3/2007 | Weitzner et al. |
| 2007/0065077 A1 | 3/2007 | Childers et al. |
| 2007/0112355 A1 | 5/2007 | Salahieh |
| 2007/0123851 A1 | 5/2007 | Alejandro et al. |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0156019 A1 | 7/2007 | Larkin et al. |
| 2007/0249901 A1 | 10/2007 | Ohline et al. |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2007/0287999 A1 | 12/2007 | Malecki et al. |
| 2007/0293724 A1 | 12/2007 | Saadat et al. |
| 2007/0299434 A1 | 12/2007 | Malecki et al. |
| 2008/0009750 A1 | 1/2008 | Aeby et al. |
| 2008/0015445 A1 | 1/2008 | Saadat et al. |
| 2008/0033284 A1 | 2/2008 | Hauck |
| 2008/0039255 A1 | 2/2008 | Jinno et al. |
| 2008/0051629 A1 | 2/2008 | Sugiyama et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitpatrick |
| 2008/0146874 A1 | 6/2008 | Miller |
| 2008/0147089 A1 | 6/2008 | Loh |
| 2008/0177285 A1 | 7/2008 | Brock et al. |
| 2008/0183071 A1 | 7/2008 | Strommer et al. |
| 2008/0188890 A1 | 8/2008 | Weitzner et al. |
| 2008/0208001 A1 | 8/2008 | Hadani |
| 2008/0212082 A1 | 9/2008 | Froggatt et al. |
| 2008/0218770 A1 | 9/2008 | Moll et al. |
| 2008/0225505 A1 | 9/2008 | Martin |
| 2008/0262480 A1 | 10/2008 | Stahler et al. |
| 2008/0281293 A1 | 11/2008 | Peh et al. |
| 2008/0300592 A1 | 12/2008 | Weitzner et al. |
| 2008/0319311 A1 | 12/2008 | Hamadeh |
| 2009/0024141 A1 | 1/2009 | Stahler et al. |
| 2009/0054884 A1 | 2/2009 | Farley et al. |
| 2009/0099420 A1 | 4/2009 | Woodley et al. |
| 2009/0099554 A1 | 4/2009 | Forster et al. |
| 2009/0163851 A1 | 6/2009 | Holloway |
| 2009/0221908 A1 | 9/2009 | Glossop |
| 2009/0247880 A1 | 10/2009 | Naruse et al. |
| 2009/0254083 A1 | 10/2009 | Wallace et al. |
| 2009/0262109 A1 | 10/2009 | Markowitz et al. |
| 2009/0299344 A1 | 12/2009 | Lee et al. |
| 2009/0306587 A1 | 12/2009 | Milijasevic et al. |
| 2009/0318797 A1 | 12/2009 | Hadani |
| 2010/0030023 A1 | 2/2010 | Yoshie |
| 2010/0073150 A1 | 3/2010 | Olson et al. |
| 2010/0081920 A1 | 4/2010 | Whitmore, III et al. |
| 2010/0114115 A1 | 5/2010 | Schlesinger et al. |
| 2010/0130823 A1 | 5/2010 | Ando |
| 2010/0168918 A1 | 7/2010 | Zhao |
| 2010/0217184 A1 | 8/2010 | Koblish et al. |
| 2010/0249497 A1 | 9/2010 | Peine et al. |

(56) References Cited

U.S. PATENT DOCUMENTS

| | | |
|---|---|---|
| 2010/0249506 A1 | 9/2010 | Prisco et al. |
| 2010/0280320 A1 | 11/2010 | Alvarez et al. |
| 2010/0280525 A1 | 11/2010 | Alvarez et al. |
| 2011/0009863 A1 | 1/2011 | Stanislaw |
| 2011/0046441 A1 | 2/2011 | Wiltshire et al. |
| 2011/0048216 A1 | 3/2011 | Lindh et al. |
| 2011/0077681 A1 | 3/2011 | Nagano |
| 2011/0098533 A1 | 4/2011 | Onoda |
| 2011/0130718 A1 | 6/2011 | Kidd et al. |
| 2011/0148442 A1 | 6/2011 | Berner |
| 2011/0152880 A1 | 6/2011 | Alvarez et al. |
| 2011/0162195 A1 | 7/2011 | Webster et al. |
| 2011/0245844 A1 | 10/2011 | Jinno et al. |
| 2011/0261183 A1 | 10/2011 | Ma et al. |
| 2011/0306836 A1 | 12/2011 | Ohline et al. |
| 2012/0071822 A1 | 3/2012 | Romo et al. |
| 2012/0071894 A1 | 3/2012 | Tanner et al. |
| 2012/0071895 A1 | 3/2012 | Stahler et al. |
| 2012/0123327 A1 | 5/2012 | Miller |
| 2012/0136419 A1 | 5/2012 | Zarembo et al. |
| 2012/0137491 A1 | 6/2012 | Macnamara |
| 2012/0143226 A1 | 6/2012 | Belson et al. |
| 2012/0190976 A1 | 7/2012 | Kleinstreuer |
| 2012/0191107 A1 | 7/2012 | Tanner et al. |
| 2012/0221038 A1 | 8/2012 | Simpson |
| 2012/0239012 A1 | 9/2012 | Laurent et al. |
| 2012/0259244 A1 | 10/2012 | Roberts et al. |
| 2012/0283747 A1 | 11/2012 | Popovic |
| 2012/0289777 A1 | 11/2012 | Chopra |
| 2013/0018400 A1 | 1/2013 | Milton et al. |
| 2013/0030363 A1 | 1/2013 | Wong et al. |
| 2013/0030519 A1 | 1/2013 | Tran et al. |
| 2013/0035537 A1 | 2/2013 | Wallace et al. |
| 2013/0090552 A1 | 4/2013 | Ramamurthy et al. |
| 2013/0109957 A1 | 5/2013 | Hooft et al. |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0204124 A1 | 8/2013 | Duindam |
| 2013/0226151 A1 | 8/2013 | Suehara |
| 2013/0303892 A1 | 11/2013 | Zhao |
| 2013/0304091 A1 | 11/2013 | Straehnz |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0012288 A1 | 1/2014 | Darisse |
| 2014/0046313 A1 | 2/2014 | Pederson et al. |
| 2014/0142591 A1 | 5/2014 | Alvarez et al. |
| 2014/0200402 A1 | 7/2014 | Snoke et al. |
| 2014/0235943 A1 | 8/2014 | Paris |
| 2014/0276594 A1 | 9/2014 | Tanner et al. |
| 2014/0276936 A1 | 9/2014 | Kokish et al. |
| 2014/0316397 A1 | 10/2014 | Brown |
| 2014/0343416 A1 | 11/2014 | Panescu |
| 2014/0357984 A1 | 12/2014 | Wallace et al. |
| 2014/0364870 A1 | 12/2014 | Alvarez et al. |
| 2015/0031950 A1 | 1/2015 | Drontle et al. |
| 2015/0255782 A1 | 9/2015 | Kim et al. |
| 2015/0374956 A1* | 12/2015 | Bogusky ........... A61M 25/0052 604/95.04 |
| 2016/0000414 A1 | 1/2016 | Brown |
| 2016/0001038 A1 | 1/2016 | Romo et al. |
| 2016/0007881 A1 | 1/2016 | Wong et al. |
| 2016/0067450 A1 | 3/2016 | Kowshik |
| 2016/0183841 A1 | 6/2016 | Duindam et al. |
| 2016/0227982 A1 | 8/2016 | Takahashi |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0346049 A1 | 12/2016 | Allen et al. |
| 2016/0372743 A1 | 12/2016 | Cho et al. |
| 2016/0374590 A1 | 12/2016 | Wong et al. |
| 2017/0007337 A1 | 1/2017 | Dan |
| 2017/0071684 A1 | 3/2017 | Kokish et al. |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0281218 A1 | 10/2017 | Timm |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0055589 A1 | 3/2018 | Joseph et al. |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0105110 A1 | 4/2019 | Tanner et al. |
| 2019/0105776 A1 | 4/2019 | Ho et al. |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0307987 A1 | 10/2019 | Yu |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0046942 A1 | 2/2020 | Alvarez |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |

(56) References Cited

U.S. PATENT DOCUMENTS

| | | |
|---|---|---|
| 2020/0146769 A1 | 5/2020 | Eyre |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| CN | 1857877 | 11/2006 |
| CN | 102316817 | 1/2012 |
| CN | 102458295 | 5/2012 |
| CN | 102665590 | 9/2012 |
| CN | 102711586 | 10/2012 |
| CN | 102973317 | 3/2013 |
| CN | 103767659 | 5/2014 |
| CN | 103930063 | 7/2014 |
| EP | 0543539 | 5/1993 |
| EP | 0776739 | 6/1997 |
| EP | 1285634 | 2/2003 |
| EP | 1442720 | 8/2004 |
| EP | 0904796 | 11/2004 |
| EP | 2204208 | 7/2010 |
| GB | 2102590 | 2/1983 |
| JP | 2006-525087 | 11/2006 |
| JP | 2007-511247 | 5/2007 |
| JP | 2010-046384 | 3/2010 |
| JP | 2011-015992 | 1/2011 |
| JP | 2012-105793 | 6/2012 |
| WO | WO 1994/014494 | 7/1994 |
| WO | WO 1997/044089 | 11/1997 |
| WO | WO 2000/011495 | 3/2000 |
| WO | WO 2000/045193 | 8/2000 |
| WO | WO 2000/067640 | 11/2000 |
| WO | WO 2001/056457 | 8/2001 |
| WO | WO 2002/074178 | 9/2002 |
| WO | WO 2003/077769 | 9/2003 |
| WO | WO 2003/091839 | 11/2003 |
| WO | WO 2004/039273 | 5/2004 |
| WO | WO 2004/104714 | 12/2004 |
| WO | WO 2004/105849 | 12/2004 |
| WO | WO 2005/032637 | 4/2005 |
| WO | WO 2005/081202 | 9/2005 |
| WO | WO 2005/087128 | 9/2005 |
| WO | WO 2007/146987 | 12/2007 |
| WO | WO 2007/149841 | 12/2007 |
| WO | WO 2008/033589 | 3/2008 |
| WO | WO 2008/097540 | 8/2008 |
| WO | WO 2009/097461 | 6/2009 |
| WO | WO 2009/092059 | 7/2009 |
| WO | WO 2010/081187 | 7/2010 |
| WO | WO 2010/127162 | 11/2010 |
| WO | WO 2011/005335 | 1/2011 |
| WO | WO 2011/132409 | 10/2011 |
| WO | WO 2013/107468 | 7/2013 |
| WO | WO 2015/093602 | 12/2013 |
| WO | WO 2016/003052 | 1/2016 |

OTHER PUBLICATIONS

Jung et al., "A Modeling Approach for Continuum Robotic Manipulators: Effects of Nonlinear Internal Device Friction," IEEE-RSJ International Conference on Intelligent Robots and Systems, Sep. 25-30, 2011, pp. 5139-5146, California.

Chinese Office Action dated Aug. 19, 2010, for Application No. 200780006359.8, 6 pages.

European Office Action dated Dec. 9, 2008, for Application No. 07757358.2, 3 pages.

Extended European Search Report dated Apr. 14, 2014, for Application No. 13193922.5, 9 pages.

International Search Report and Written Opinion dated Jun. 27, 2005, for International Application No. PCT/US2005/007108, 10 pages.

International Search Report and Written Opinion dated Dec. 12, 2006, for International Application No. PCT/US2006/026218, 11 pages.

International Search Report and Written Opinion dated Jul. 12, 2007, for International Application No. PCT/US2007/062617, 9 pages.

International Preliminary Report on Patentability dated Aug. 26, 2008, for International Application No. PCT/US2007/062617, 7 pages.

\* cited by examiner

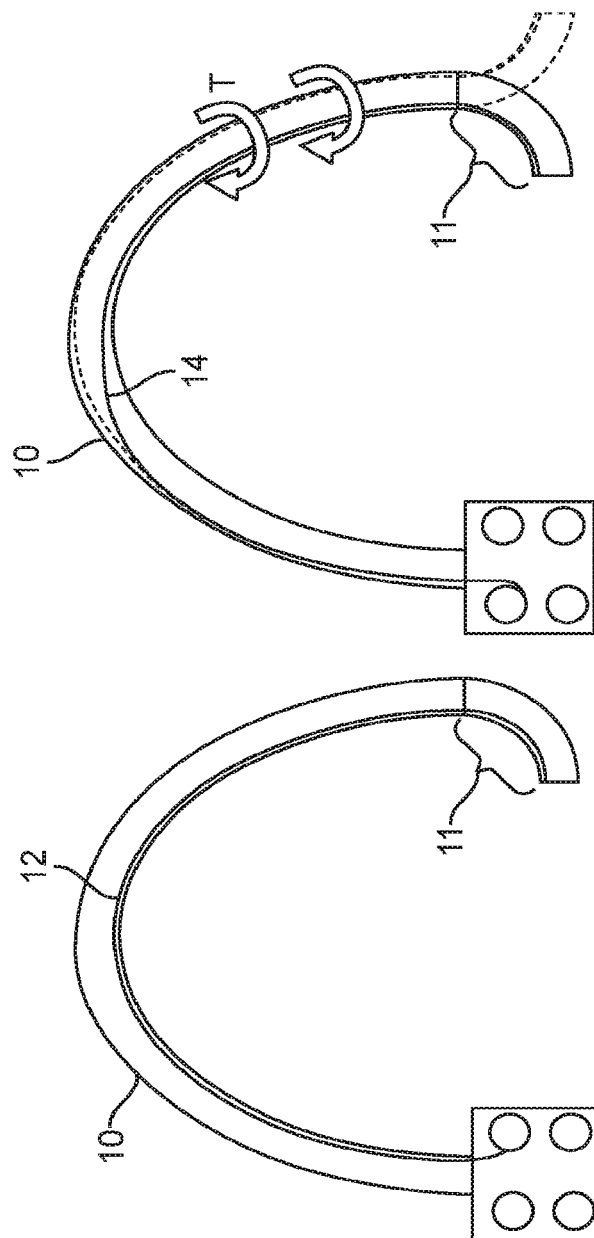

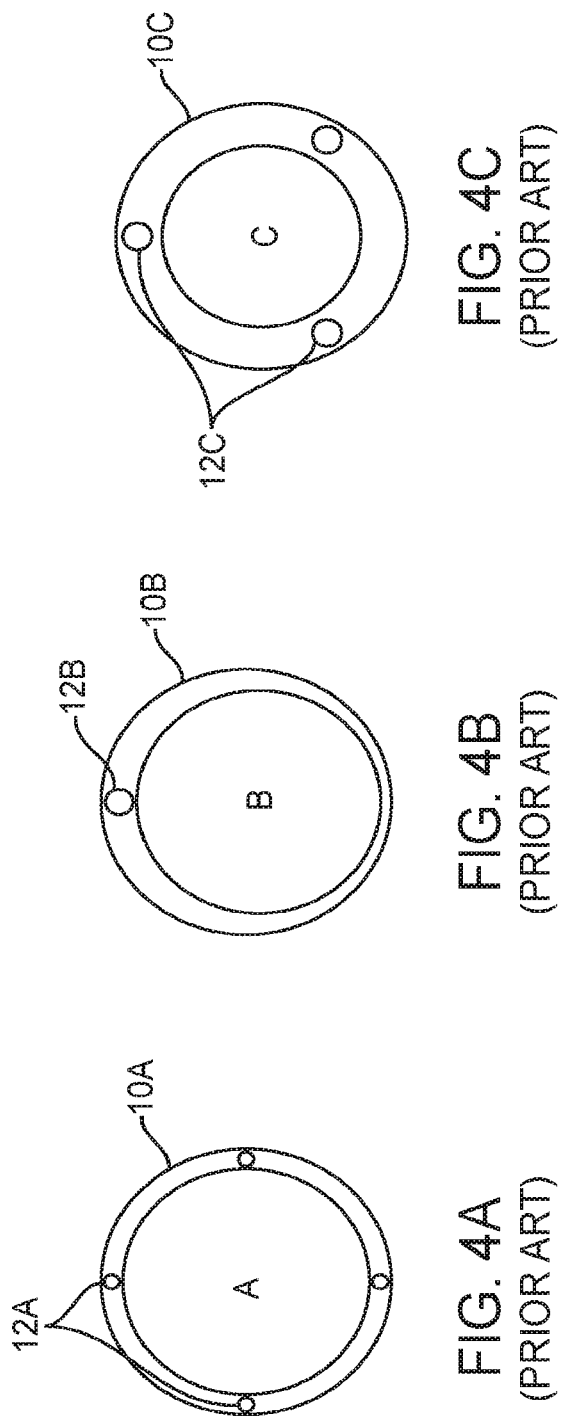

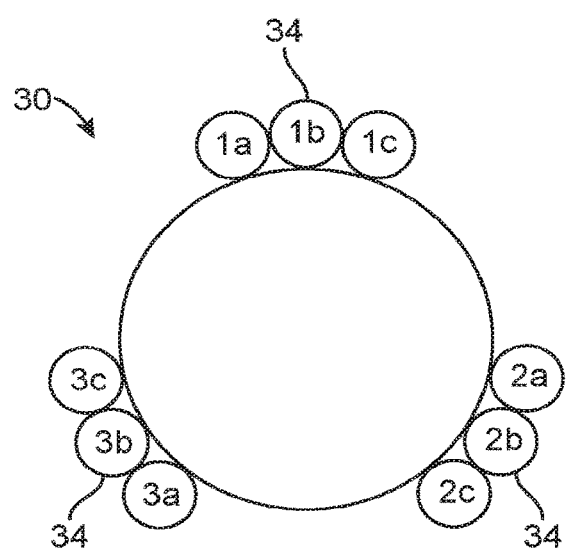
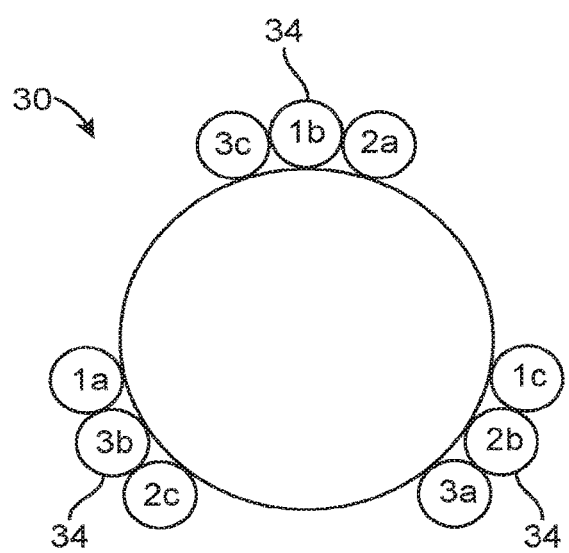
FIG. 7A — Articulation Section
FIG. 7B — Shaft Section

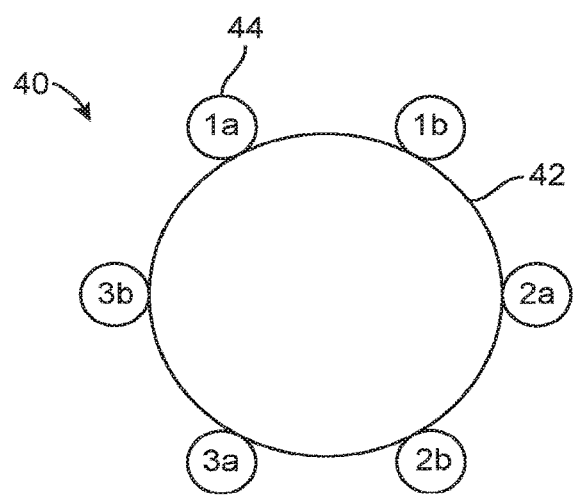 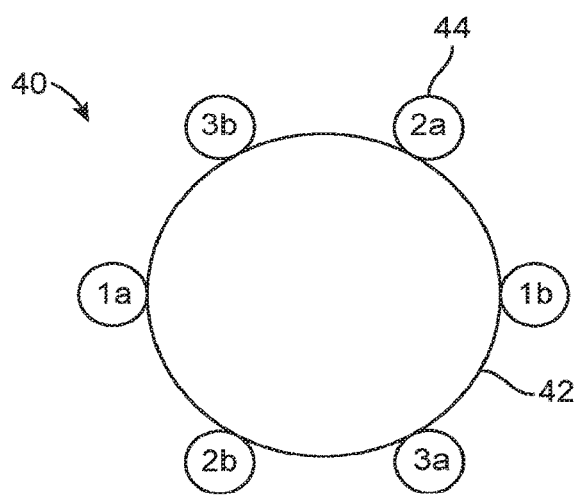
FIG. 8A — Articulation Section
FIG. 8B — Shaft Section

Articulation Section

Shaft Section

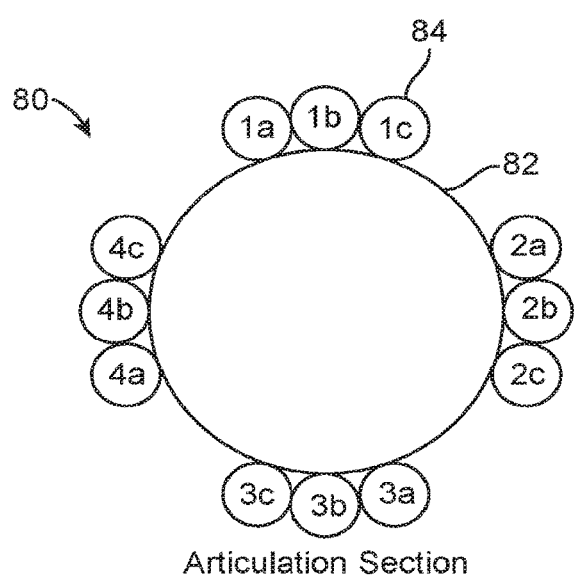 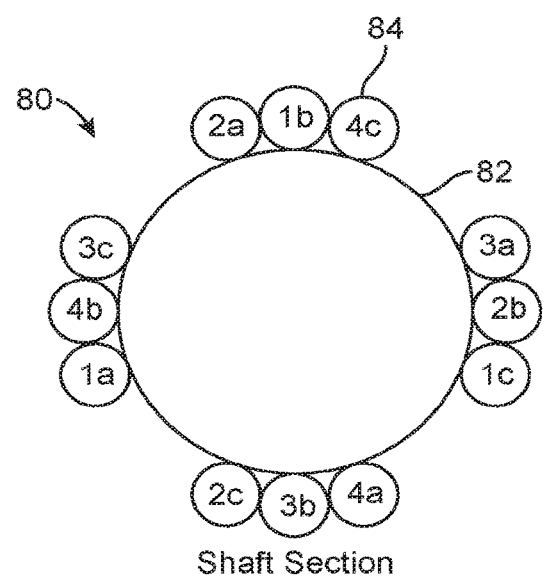
FIG. 12A — Articulation Section
FIG. 12B — Shaft Section

Articulation Section

Shaft Section

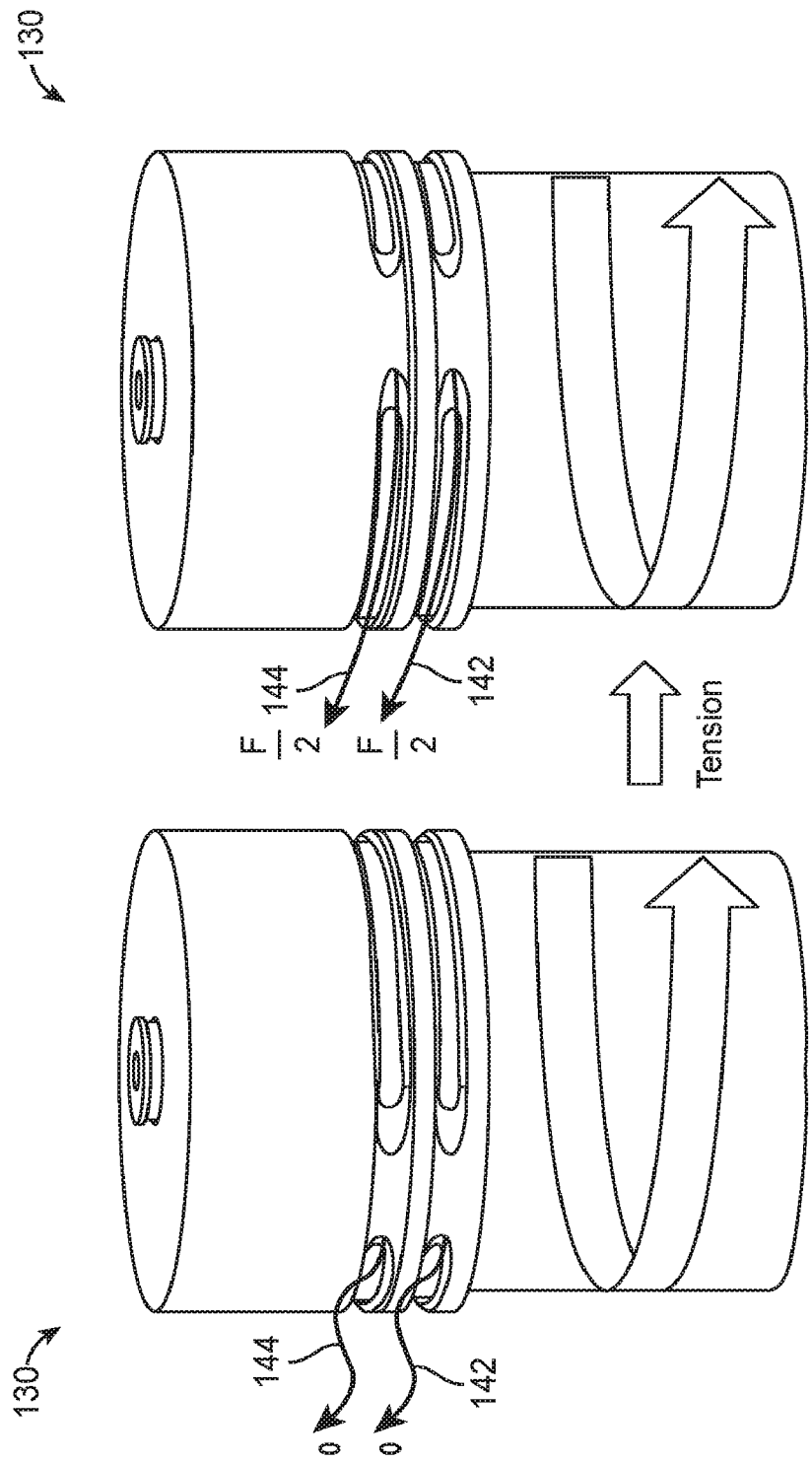

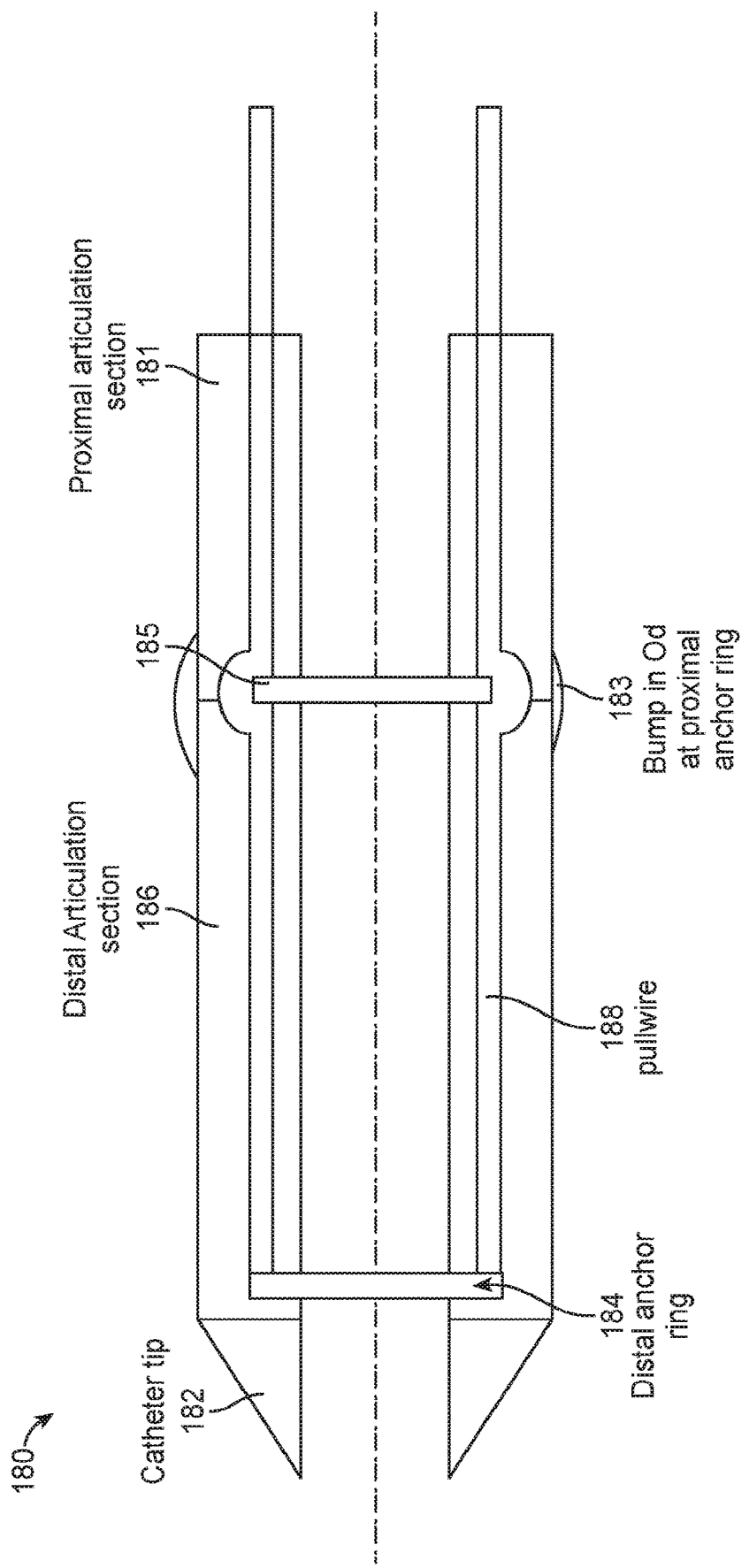

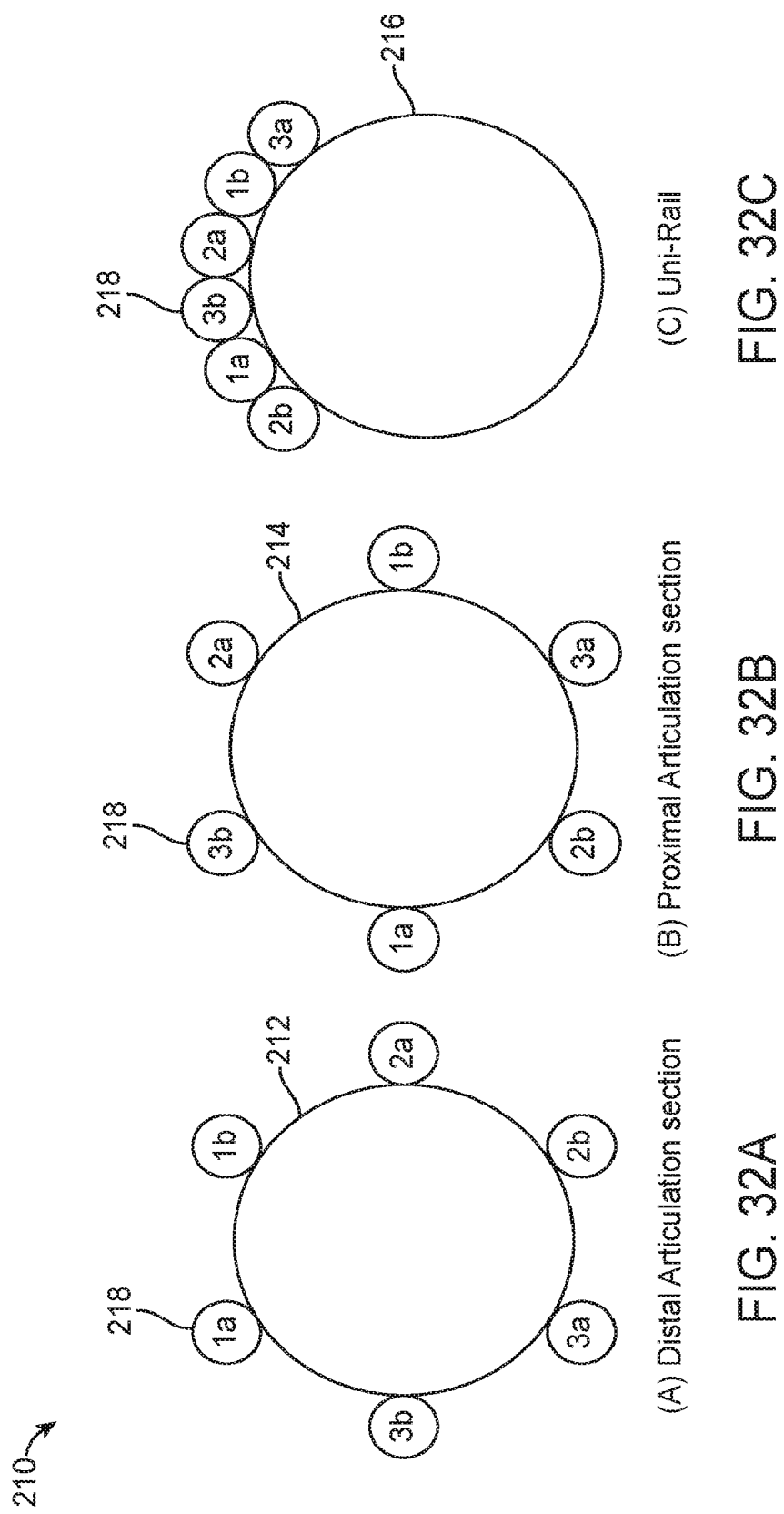

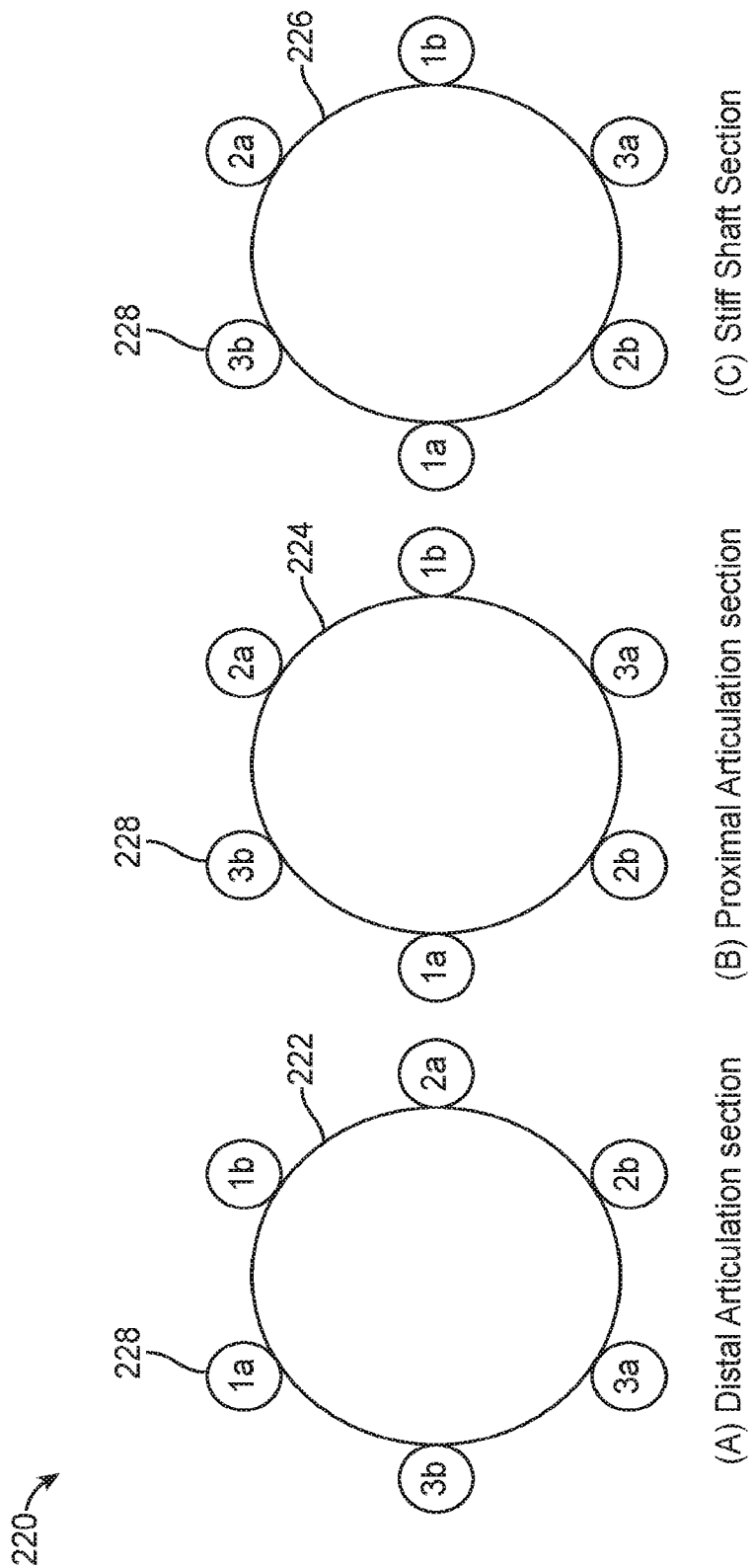

STEERABLE CATHETER WITH SHAFT LOAD DISTRIBUTIONS

This application is a continuation of U.S. patent application Ser. No. 16/588,890, filed Sep. 30, 2019, entitled "Steerable Catheter with Shaft Load Distributions," issued as U.S. Pat. No. 11,701,192 on Jul. 18, 2023; and which is a divisional U.S. patent application Ser. No. 15/248,316, filed Aug. 26, 2016, entitled "Steerable Catheter with Shaft Load Distributions," issued as U.S. Pat. No. 10,463,439 on Nov. 5, 2019,

FIELD

The invention relates generally to minimally-invasive instruments and systems, such as manually or robotically steerable catheter systems. More specifically, the invention relates to steerable catheter systems for performing minimally invasive diagnostic and therapeutic procedures.

BACKGROUND

Robotic steerable catheter systems typically include a flexible catheter shaft having an articulation section at a distal tip. These systems are designed to facilitate access to distal target sites in the human anatomy and require simultaneous articulation of the distal tip with continued insertion or retraction of the catheter. Pullwire based articulating catheters typically have pullwires passing through the shaft, and each pullwire is anchored to a fixed location around the distal tip. Each pullwire is then selectively tensioned to articulate the tip in various directions. As such, the catheter shaft should be laterally flexible to follow the curvature in the anatomy, but axially rigid to resist the high axial loads being applied to articulate the catheter tip.

Increasing the lateral flexibility of the catheter, however, introduces catheter navigation problems that may not otherwise occur when the catheter is laterally stiff. For example, many steerable catheters have a multitude of free floating pullwires (e.g., four pullwires), circumferentially spaced in the wall of the catheter and attached to a control ring embedded in the distal end of the catheter. If four pullwires are provided, the pullwires may be orthogonally spaced from each other. Each of these pullwires is offset from the center axis of the catheter, so that when a wire is tensioned to steer the catheter's distal tip under ideal conditions, the resulting bending moment causes the distal tip to articulate in the direction of the pullwire that is tensioned. However, the compressive forces from the tensioned pullwire on the relatively flexible catheter shaft also cause the shaft to compress and/or to experience other undesired effects.

For example, flexible shafts adapt to the shape of the anatomy as they track through it. This results in a curved shaft. The curvature of the catheter shaft may make the articulation performance of the catheter unrepeatable and inconsistent. In particular, because the pullwires are offset from the neutral axis of the catheter shaft, bending the catheter shaft causes the pullwires on the outside of the curve to tighten while the pullwires on the inside of the curve slacken. As a result, the amount of tension that should be applied to the pullwires in order to effect the desired articulation of the distal tip varies in accordance with the amount of curvature applied to the catheter shaft.

Referring to FIGS. 1A and 1B, a prior art catheter 10 with an articulating distal portion 11 (or "distal tip") is shown, to illustrate another example of the challenges faced when articulating a catheter in a body. As illustrated, one challenge is that the articulated distal tip 11, when bent, tends to align its curvature with the curvature of the shaft of the catheter 10. In particular, as shown in FIG. 1B, operating or tensioning a pullwire 14 on the outside edge of a bend may cause the catheter 10 to rotate or twist. This rotation or twist phenomenon is known as "curve alignment," because the distal tip 11 and shaft of the catheter 10 tend to rotate until the tensioned pullwire 14 is on the inside of the bend, and the curve in the distal tip 11 is aligned with the curvature in the shaft. That is, when the proximal shaft section of the catheter 10 is curved (as it tracks through curved anatomy), and the distal tip 11 is commanded to articulate, the curvature in the shaft can impact the articulation performance of the distal tip 11.

In FIG. 1A, the pullwire 12 that is pulled happens to be on the inside of the bend of the catheter shaft 10, and the distal tip 11 articulates to the left as intended. However, if it is desired to bend the distal tip 11 in a direction that is not aligned with the curvature of the proximal portion of the catheter 10, (e.g., if it is desired to bend the distal tip 11 to the right, as shown by the dotted distal tip outline in FIG. 1B), the pullwire 14 on the outside of the bend is pulled. A torsional load (T) is applied to the shaft as tension increases on the pullwire 14 on the outside of the bend. This torsional load rotates the shaft until the pulled pullwire 14 is on the inside of the bend. As shown in FIG. 1B, the initial position of the outer pullwire 14 is depicted by a dashed line, and the rotated position following application of the torsional load is depicted by the solid line. In effect, the tensioned pullwire 14 on the outside of the bend takes the path of least resistance, which may often rotate the shaft to the inside of the bend (as shown by the thick, solid-tipped arrows in FIG. 1B), rather than articulating the distal tip 11 as the user intends. This results in the distal tip 11 pointing to the left, as shown in the solid-line version of the distal tip 11, even though the user wanted to bend the distal tip 11 to the right, as shown in the dotted-line version. This unintentional rotation of the shaft causes instability of the catheter distal tip 11 and prevents the physician from being able to articulate the distal tip 11 to the right. In other words, no matter which direction the catheter distal tip 11 is intended to be bent, it may ultimately bend in the direction of the proximal curve. This phenomenon is known as curve alignment, because the pullwire 14 that is under tension puts a compressive force on both the proximal and distal sections of the catheter 10 causing both the proximal and distal curvatures to align in the same direction in order to achieve the lowest energy state.

The operator may attempt to roll the entire catheter 10 from the proximal end in order to place the articulated distal tip in the desired direction. However, this moves the tensioned inside pullwire 14 to the outside of the proximal bend, causing further tensioning of the pullwire 14. This increased tension on the pullwire 14 on the outside of the bend can cause an unstable position. The catheter shaft 10 wants to return to a lower energy state and may do so by quickly whipping around to get the tensioned pullwire 14 back to the inside of the bend. In a multi-direction catheter, the operator may attempt to pull a different pullwire to try to bend the distal tip to the right, but as soon as the tension is built up on that wire, it also wants to spin the distal tip around and return to the inside of the bend. Continued attempts to try to find a pullwire to articulate the distal tip against the direction of curvature of the catheter shaft may lead to rotation or windup of the catheter shaft. This stored energy in the shaft can lead to whipping of the catheter shaft to return to a lower energy state and may injure the patient.

FIGS. 2A and 2B illustrate another example of the challenges faced when articulating a flexible catheter 10. When performing a steering maneuver with a flexible catheter 10, the tension on the pullwire(s) causes axial compression on the catheter shaft, which bends the distal tip 11 of the catheter 10. This axial compression may cause undesired lateral deflection in flexible catheter shafts, thereby rendering the catheter mechanically unstable. FIGS. 2A and 2B illustrate how prior art flexible instruments exhibit unwanted lateral shaft deflection when one or more pullwires are pulled. In these figures, the pullwires run through the wall of the catheter shaft. An example of ideal articulation performance is shown in FIG. 2B. If the shaft is made of stiff materials, then the catheter distal tip 11 is more likely to exhibit ideal articulation performance. If the catheter shaft is made of more flexible, trackable materials, then the catheter 10 is more likely to bend as shown in FIG. 2A, with bending occurring not only in the distal tip 11, but also along a length of the catheter shaft. The shaft of the catheter is being muscled by the pullwires and experiencing unwanted lateral deflection.

The additional lateral deflection of the shaft of the catheter 10 may be undesirable, because it may unintentionally force the catheter against the anatomy. This has the potential for injury and distracts the operator, because he or she must constantly monitor what the shaft is doing. If the shaft is in a constrained position within the arteries, such as passing over the iliac bifurcation, the arterial rigidity may stop the shaft from being muscled by the pullwires. But alternatively, the catheter shaft may be in a more flexible artery, such as the splenic artery, where the catheter may damage or distort the shape of the artery.

Referring to FIGS. 3A-3C, if a catheter 10 is in a large artery or open chamber, such as the aorta or heart, the catheter 10 may have space to deflect. This creates an additional problem, because the more space the catheter shaft has to deflect, the greater the impact on the amount of catheter tip articulation. For example, FIGS. 3A-3C show the catheter 10 in three different configurations. In FIG. 3A, both the proximal shaft and the distal articulation tip 11 are straight. In FIG. 3B, a pullwire has been pulled a distance x, and the articulation tip 11 has bent 90 degrees. The proximal shaft has not bent. This may occur, for example, when the shaft is constrained by the anatomy. In FIG. 3C, the pullwire has been tensioned an equal amount as in FIG. 3B, but the shaft has also compressed. Therefore, in FIG. 3C, some of the pullwire displacement has been "used up" to compress the shaft, and hence there is less compression of the articulation tip 11. As a result, the articulation tip 11 only bends approximately 80 degrees in FIG. 3C. It would be desirable to isolate bending to the distal articulation tip 11, to aid in predictability and controllability. In other words, an ideal catheter instrument would have a distal articulation tip 11 that bends as commanded and is not dependent on the anatomical path or the stiffness of the vasculature.

Undesirable lateral motion related to muscling and undesirable rotational motion related to curve alignment both result from the same forces associated with pullwire tensioning. Each of these mechanical challenges contributes to the instability and poor control of the catheter tip, as well as decreased catheter tracking performance. Some steerable catheters overcome these problems and resist compressive and torsional forces by increasing the axial stiffness of the entire catheter shaft (e.g., by varying wall thickness, material durometer, and/or braid configuration), or alternatively by incorporating axially stiff members within the catheter shaft to take the axial load. But these changes also laterally stiffen the catheter shaft, making it less maneuverable, and thereby causing new difficulties in tracking the catheter through the vasculature of the patient. Therefore, the catheter designer is forced to compromise between articulation performance and shaft tracking performance.

Another design intended to overcome the problems of muscling and curve alignment involves locating all the pullwires in the shaft close to the neutral axis, as described in U.S. Pat. No. 8,894,610. This is known as the "unirail design" for a catheter. While the unirail design locates all pullwires in one location, it is impossible to locate all pullwires exactly on the neutral axis, so the catheter continues to experience some slight unwanted shaft curvature. Catheter designers typically need to design some lateral stiffness into the catheter shaft, to try to minimize this unwanted curvature. Therefore, the shaft of the unirail catheter cannot be designed with very low lateral stiffness.

Another strategy is to spiral the pullwires around the circumference of the catheter shaft, as described in U.S. patent application Ser. No. 14/542,373 (U.S. Patent App. Pub. No. 2015/0164594), issued as U.S. Pat. No. 10,405,939 on Sep. 10, 2019. This is known as the helical design and can be used to balance loads in the catheter shaft. However, continuously spiraling the pullwires leads to increased friction in the catheter system, and so there is still a tradeoff between shaft flexibility and articulation performance.

Other steerable catheters overcome this problem by using free floating coil pipes in the wall of the catheter to respectively house the pullwires, thereby isolating the articulation loads from the catheter shaft. (Embodiments and details are described in U.S. patent application Ser. No. 13/173,994, entitled "Steerable Catheter," (U.S. Patent App. Pub. No. 2012/0071822), issued as U.S. Pat. No. 8,827,948 on Sep. 9, 2014, which is expressly incorporated herein by reference in its entirety.) However, the use of coil pipes adds to the cost of the catheter and takes up more space in the shaft, resulting in a thicker catheter wall. Such a design is not appropriate for catheters with small outer diameters intended for use in narrow vasculature.

Pullwire-based steerable catheters typically incorporate the steering pullwires into the walls of the catheters, and the catheters must be designed to accommodate the thickness and arrangement of the pullwires. Referring to FIGS. 4A-4C, various examples of pullwire-based steerable catheters 10A-10C are provided, each including steering pullwires 12A-12C in the wall of the respective catheter. The diameter of the steering pullwires 12A-12C usually determines the wall thickness that can be achieved. For example, in the embodiment illustrated in FIG. 4A, there are four small pullwires 12A evenly spaced around the circumference of the catheter 10A, whereas in FIG. 4C, there are three larger diameter pullwires 12C equally spaced around the circumference of the catheter 10C. The embodiment in FIG. 4A has a thinner wall, due to the smaller diameter of the pullwires 12A. Thinner walls are preferable, because, as shown, they allow for a larger inner diameter (ID) for a given outer diameter (OD), or a smaller OD for a given ID. In other words, thin walls allow for the smallest OD:ID ratio. Advantageously, larger inner diameters allow for delivery of a broader range of tools. Smaller outer diameters allow for access to narrower blood vessels, thereby increasing the number of procedures that can be performed with steerable catheters. Smaller ODs also allow for smaller incisions in patients and hence, faster recovery times.

One barrier to achieving a small OD:ID ratio is the diameter of the pullwires. For example, the relatively small pullwires 12A in FIG. 4A have less tensile strength than the pullwires of FIGS. 4B and 4C, and this can limit the articulation force that can be applied to bend the distal articulation tip. The embodiment in FIG. 4B is an alternative option, which uses larger pullwires 12B while maintaining a larger ID. Here, the OD and ID of the catheter 10B are not concentric. There is only one pullwire 12B, so the wall thickness is thinner in the area opposite the pullwire 12B to maximize the inner lumen. This catheter embodiment 10B, however, has a reduced degree of freedom (i.e., less maneuverability) at the distal tip. Accordingly, each design has significant tradeoffs.

Thus, although a number of innovations have been made, major unresolved challenges remain when using pullwires to articulate the distal tip of a flexible catheter. It would, therefore, be desirable to have improved steerable catheters, designed to particularly address at least some of the challenges described above. Ideally, such improved catheters would have a desired combination of stiffness, flexibility, and ease of articulation. Also ideally, the catheters would have a desirable inner diameter and outer diameter to make them suitable for passing instruments and for advancing through small incisions and vasculature. At least some of these objectives will be addressed by the embodiments described herein.

BRIEF SUMMARY

Advantageously, various steerable catheter embodiments provided herein use multiple pullwires to steer the distal tip (or "articulating section") in a single articulation direction. Those pullwires then diverge into a more spaced distribution of pullwires in the proximal shaft section (or "non-articulating section"). This results in a bending moment in the distal articulating section and no bending moment in the shaft of the catheter. This design can be repeated, so that three or more sets of pullwires may be used to create an omnidirectional articulating section. With this design, the articulating section can be independently controlled by pullwires, while the catheter experiences no shaft bending or unintended rotation. In other words, this configuration of pullwires allows a catheter shaft to have minimal lateral stiffness, and yet be able to withstand pullwire forces without experiencing unintended bending or rotation. This configuration also allows for the manufacture of thinner walled catheters, because smaller-diameter pullwires may be used in this design, compared to traditional pullwire systems, resulting in an overall reduction in outer diameter (OD) and/or increase in inner diameter (ID).

In one aspect of the present disclosure, a steerable catheter system may include a flexible elongate catheter body, a drive mechanism at the proximal end of the catheter body, and at least one group of pullwires within a catheter wall of the catheter body, extending along a length of the catheter body. The catheter body may include a catheter wall forming a central lumen, a proximal end, a distal end, a distal articulating section, and a proximal non-articulating section. Each group of pullwires includes at least two pullwires, and each of the pullwires is anchored at a first end to the catheter body and at a second end to the drive mechanism. The pullwires of each group are positioned close to one another along the articulating section of the catheter body and diverge away from one another to reach a more separated distribution along the non-articulating section.

In some embodiments, the two pullwires in each group are distributed uniformly around the circumference in the non-articulating section. In some embodiments, each group of pullwires includes three or more pullwires, and the more separated distribution of the three or more pullwires in the non-articulating section means that each pullwire in a given group is positioned less than 180 degrees away from each immediately adjacent pullwire in the given group.

Various alternative embodiments may include any suitable number of groups of pullwires and any suitable number of pullwires per group. For example, some embodiments may include three groups of pullwires with at least two pullwires per group, other embodiments may include three groups of pullwires with at least three pullwires per group, etc.

In some embodiments, the system may also include a robotic instrument driver, which includes a splayer comprising multiple pulleys. Each of the pulleys is attached to one of the pullwires, and each of the pulleys is configured to be rotated by a motor in the robotic instrument driver. In some of these embodiments, each of the pulleys may be configured to be rotated to generate tension in the two pullwires, where an increase in tension on all of the at least two pullwires contributes to deflection of the articulating section of the catheter body. Also in some embodiments, the tension on the two pullwires contributes to a bending moment in the articulating section of the catheter body while cancelling the bending moment in the non-articulating section.

In other embodiments, the system may also include a robotic instrument driver, where the drive mechanism includes a splayer having multiple pulleys, and where each of the pulleys is attached to one group of pullwires. Each of the multiple pulleys interfaces with a motor in the instrument driver to increase tension in the one group of pullwires to articulate the catheter body. Such embodiments may also include a load balancing actuation mechanism for facilitating proportional tensioning of each pullwire within at least one group of pullwires. Examples of load balancing actuation mechanisms include a two-way whiffletree, a three-way whiffletree, an elastic pullwire, a two-way differential, and a three-way differential.

In some embodiments, the catheter body has a cylindrical shape. In some embodiments, the at least two pullwires of the group of pullwires spiral around the catheter body along a divergence section, disposed between the articulating section and the non-articulating section, to transition from their positions in the articulating section to their positions in the non-articulating section.

In another aspect of the present disclosure, a multiple-bend steerable catheter may include a flexible elongate catheter body and multiple pullwires within a catheter wall of the catheter body, fixed to the distal end of the catheter body and extending along the catheter body to the proximal end. The catheter body may include a catheter wall forming a central lumen, a proximal end, a distal end, a distal articulating section at the distal end of the catheter body, a proximal non-articulating section at the proximal end of the catheter body, and a proximal articulating section located between the distal articulating section and the proximal non-articulating section. The pullwires are configured in groups of at least two pullwires each, and the at least two pullwires of each group are positioned closer to one another in the distal articulation section than in the proximal articulation section.

Some embodiments include three groups of two pullwires each, where the pullwires in each group are located close to one another in the distal articulating section and are located directly across from one another in the proximal articulating section. In alternative embodiments, all of the pullwires are located along one side of the catheter body in the proximal non-articulating section. In some embodiments, the pullwires in each group are located directly across from one another in the proximal non-articulating section, and the proximal non-articulating section of the catheter body is stiffer than the distal articulating section and the proximal articulating section.

In some embodiments, the at least two pullwires in each group of pullwires are located in first circumferential positions along the distal articulating section, second circumferential positions along the proximal articulating section, and third circumferential positions along the proximal non-articulating section, where the second circumferential positions are farther apart from one another than the first circumferential positions. In one such embodiment, the third circumferential positions are the same as the second circumferential positions, and the proximal non-articulating section of the catheter body is stiffer than the distal articulating section and the proximal articulating section.

Some embodiments of the catheter may include twelve pullwires, which may include a first collection of nine pullwires grouped together in the second circumferential position on one side of the catheter body in the proximal articulating section, where the nine pullwires are separated into three groups of three pullwires in the first circumferential position, with each of the three groups separated from the other two groups by 120 degrees in the distal articulating section, and where one pullwire from each of the three groups of pullwires is positioned 120 degrees from the other two pullwires from each of the three groups in the third circumferential position in the proximal non-articulating section. The twelve pullwires may also include second collection of three pullwires uniformly positioned around the catheter body in the first circumferential position in the distal articulating section and in the second circumferential position in the proximal non-articulating section, wherein the three pullwires are distributed to an opposite side of the catheter body from the nine wires in the second circumferential position in the proximal articulating section. In these embodiments, the distal articulating section is configured to articulate when one or two of the three groups of the first collection of nine pullwires are tensioned with an amount of force equal to an amount of force applied to the second collection of three pullwires. Also in these embodiments, the proximal articulating section is configured to articulate when the second collection of three pullwires is pulled in a first direction uniformly or when the first collection of nine pullwires is pulled in a second, opposite direction uniformly.

Other embodiments of the catheter may include six pullwires, including a first collection of three pullwires positioned to articulate the distal articulating section, such that they are uniformly positioned around the catheter body in the distal articulating section and positioned to one side of the catheter body in the proximal articulating section. The six pullwires may also include a second collection of three pullwires positioned to articulate the proximal articulating section, such that they are uniformly positioned around the catheter body in the distal articulating section and distributed to one side of the catheter body in the proximal articulating section at 180 degrees opposite the first collection of three pullwires. In some of these embodiments, the distal articulating section is configured to articulate when one or two of the first collection of pullwires are tensioned with an amount of force equal to an amount of force applied to the second collection of three pullwires. Additionally, the proximal articulating section is configured to articulate when the second collection of three pullwires is pulled in a first direction uniformly or when the first collection of three pullwires is pulled in a second, opposite direction uniformly.

In yet another embodiment, the catheter may include six pullwires, including three pairs of two pullwires each. Each of the three pairs of pullwires may be spaced 120 degrees apart from the other two pairs of pullwires around the catheter body in the first circumferential position in the distal articulating section, and the two pullwires of each of the three pairs separate from one another and are positioned 180 degrees opposite each other around the catheter body in the second circumferential position in the proximal articulating section. In some embodiments, all six pullwires may be positioned on one side of the catheter body in the third circumferential position in the non-articulating proximal section.

In another aspect of the present disclosure, a steerable robotic catheter system may include an instrument driver, including at least one rotary output shaft, a flexible elongate catheter, including at least one group of three pullwires attached to and extending along a wall of the catheter body, and a drive interface connecting the catheter to the instrument driver. The drive interface includes a load balancing mechanism configured such that when the at least one rotary output shaft of the instrument driver is rotated, equal tension is applied to the three pullwires. In some embodiments, the load balancing mechanism may include a three-way differential. The three-way differential may include a sun gear, a ring gear, multiple planetary gears, a first stage fixed to a first of the three pullwires and driven by the sun gear, and a two-way differential driven by the ring gear. The two-way differential may include second and third stages fixed to second and third pullwires of the three pullwires, respectively. The sun gear may have a diameter that is half as large as a diameter of the ring gear, such that when the output shaft of the instrument driver is rotated, equal tension is applied to all of the three pullwires.

In yet another aspect of the present disclosure, a steerable robotic catheter system may include: instrument driver, including at least one rotary output shaft; a flexible elongate catheter, including a catheter body and at least one group of three pullwires attached to and extending along a wall of the catheter body; and a drive interface connecting the catheter to the instrument driver. The drive interface may include a planetary gear system, which in turn may include a sun gear, a ring gear, multiple planetary gears, and a two-way differential with a first stage and a second stage. The two way differential is driven by the ring gear, a first pullwire of the three pullwires is attached to the first stage, and a second pullwire of the three pullwires is attached to the second stage, and the sun gear has a diameter that is half a diameter of the ring gear. A third pullwire of the three pullwires is attached to the sun gear, such that when the rotary output shaft of the instrument driver is rotated, equal tension is applied to all of the three pullwires. Some embodiments may include four rotary output shafts and four groups of three pullwires each.

In another aspect of the present disclosure, a steerable robotic catheter system may include: an instrument driver, including at least one rotary output shaft; a flexible elongate catheter, including a catheter body and at least one group of two pullwires attached to and extending along a wall of the catheter body; and a drive interface connecting the catheter to the instrument driver. The drive interface includes a load balancing mechanism configured such that when the at least one rotary output shaft of the instrument driver is rotated, equal tension is applied to the two pullwires of the at least one group of pullwires. In some embodiments, the load balancing mechanism may include a two-way differential mechanism, which includes a rotating input shaft, at least one pinion coupled to and driven by the rotating input shaft, a first rotary stage coupled with the at least one pinion and attached to a first of the two pullwires, and a second rotary stage coupled with the at least one pinion and attached to a second of the two pullwires. Rotation of the input shaft results in equal load applied to the two pullwires independent of original lengths of the two pullwires. In other embodiments, the load balancing mechanism may include a two-way whiffletree.

At least some of these aspects and embodiments are described in greater detail in the following Detailed Description, along with the attached drawing figures.

BRIEF DESCRIPTION OF THE DRAWINGS

FIGS. 1A and 1B are diagrammatic top views of a prior art steerable catheter, illustrating twisting of the catheter;

FIGS. 4A-4C are diagrammatic cross-sectional views of prior art steerable catheters, illustrating three different configurations for positioning pullwires in the wall of a catheter;

FIGS. 7A and 7B are diagrammatic cross-sectional views of a steerable, nine-pullwire catheter, illustrating one possible configuration for pullwires along a distal articulation section (FIG. 7A) and a proximal shaft section (FIG. 7B) of the catheter, according to one embodiment;

FIGS. 8A and 8B are diagrammatic cross-sectional views of a steerable, six-pullwire catheter, illustrating one possible configuration for pullwires along a distal articulation section (FIG. 8A) and a proximal shaft section (FIG. 8B) of the catheter, according to one embodiment;

FIGS. 12A and 12B are diagrammatic cross-sectional views of a steerable, twelve-pullwire catheter, illustrating one possible configuration for pullwires along a distal articulation section (FIG. 12A) and a proximal shaft section (FIG. 12B) of the catheter, according to one embodiment;

FIGS. 23A-23C are perspective views of the two-way differential of FIG. 17, illustrating three different tension balancing scenarios;

FIG. 28 is a side, cross-sectional view of a distal portion of a pullwire catheter;

FIGS. 32A-32C are diagrammatic cross-sectional views of a multi-bend, six-pullwire catheter, illustrating one possible configuration for pullwires along a distal articulation section (FIG. 32A), a proximal articulation section (FIG. 32B), and a shaft section (FIG. 32C), according to one embodiment; and FIGS. 33A-33C are diagrammatic cross-sectional views of a multi-bend, six-pullwire catheter, illustrating one possible configuration for pullwires along a distal articulation section (FIG. 33A), a proximal articulation section (FIG. 33B), and a shaft section (FIG. 33C), according to an alternative embodiment.

DETAILED DESCRIPTION

Figures 2A, 2B:
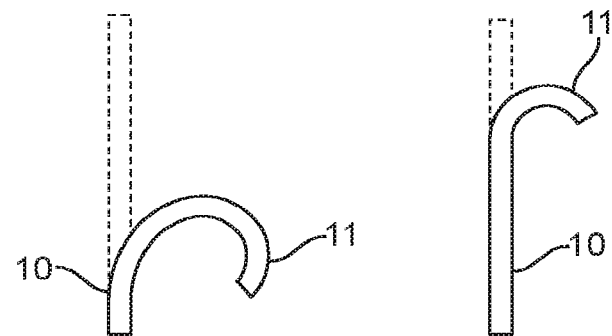
FIGS. 2A and 2B are diagrammatic side views of a prior art steerable catheter, illustrating unwanted proximal bending of the catheter.
Figure 3A:
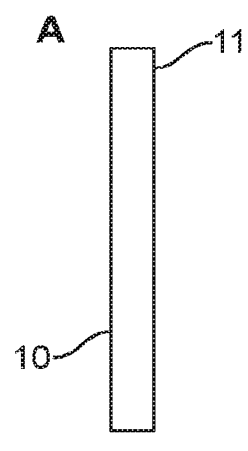
FIGS. 3A-3C are diagrammatic side views of a prior art steerable catheter, illustrating unwanted proximal bending of the catheter.
Figure 3B:
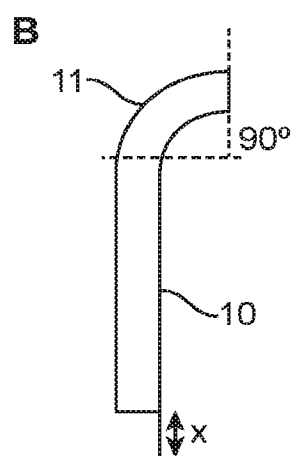
Figure 3C:
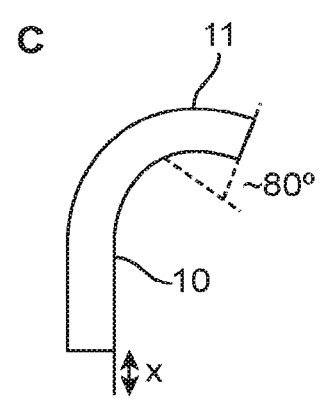

Referring now to the drawings, illustrative embodiments are shown in detail. Although the drawings represent the embodiments, the drawings are not necessarily to scale, and certain features may be exaggerated to better illustrate and explain an innovative aspect of an embodiment. Further, the embodiments described herein are not intended to be exhaustive or otherwise limit or restrict the invention to the precise form and configuration shown in the drawings and disclosed in the following detailed description.

To address at least some of the challenges with steerable catheters discussed above, a number of embodiments of a "polyrail" catheter will be described in detail below. In general, these embodiments include multiple pullwires (also referred to as "control wires," or simply, "wires"), which are spaced around a circumference of a catheter along a proximal portion of the catheter shaft and then converge toward one another so that they are touching or immediately adjacent one another along a distal, articulating portion (i.e., a distal tip) of the catheter. The embodiments typically include at least one set of at least two pullwires, but they may optionally include multiple sets of two or more pullwires. One embodiment, for example, may include three sets of three pullwires each.

In various embodiments provided herein, a steerable catheter is provided having a catheter shaft (i.e., body) formed of sidewalls. The actual shaft or body of the catheter typically runs the entire length of the catheter and includes one or more articulation sections and a proximal, non-articulating section. In this application, the terms "shaft section" and "shaft" are sometimes used to refer to the proximal portion of the catheter shaft that does not articulate, in contrast to the more distal portion (or portions) of the catheter shaft that does (or do) articulate.

Various exemplary embodiments may be used as part of a robotic catheter manipulation system as described below, but the invention is not limited to use in robotic systems. Several exemplary embodiments are described below in further detail, but these embodiments are only examples and should not be interpreted as limiting the scope of the invention as set forth in the claims.

Figure 5:
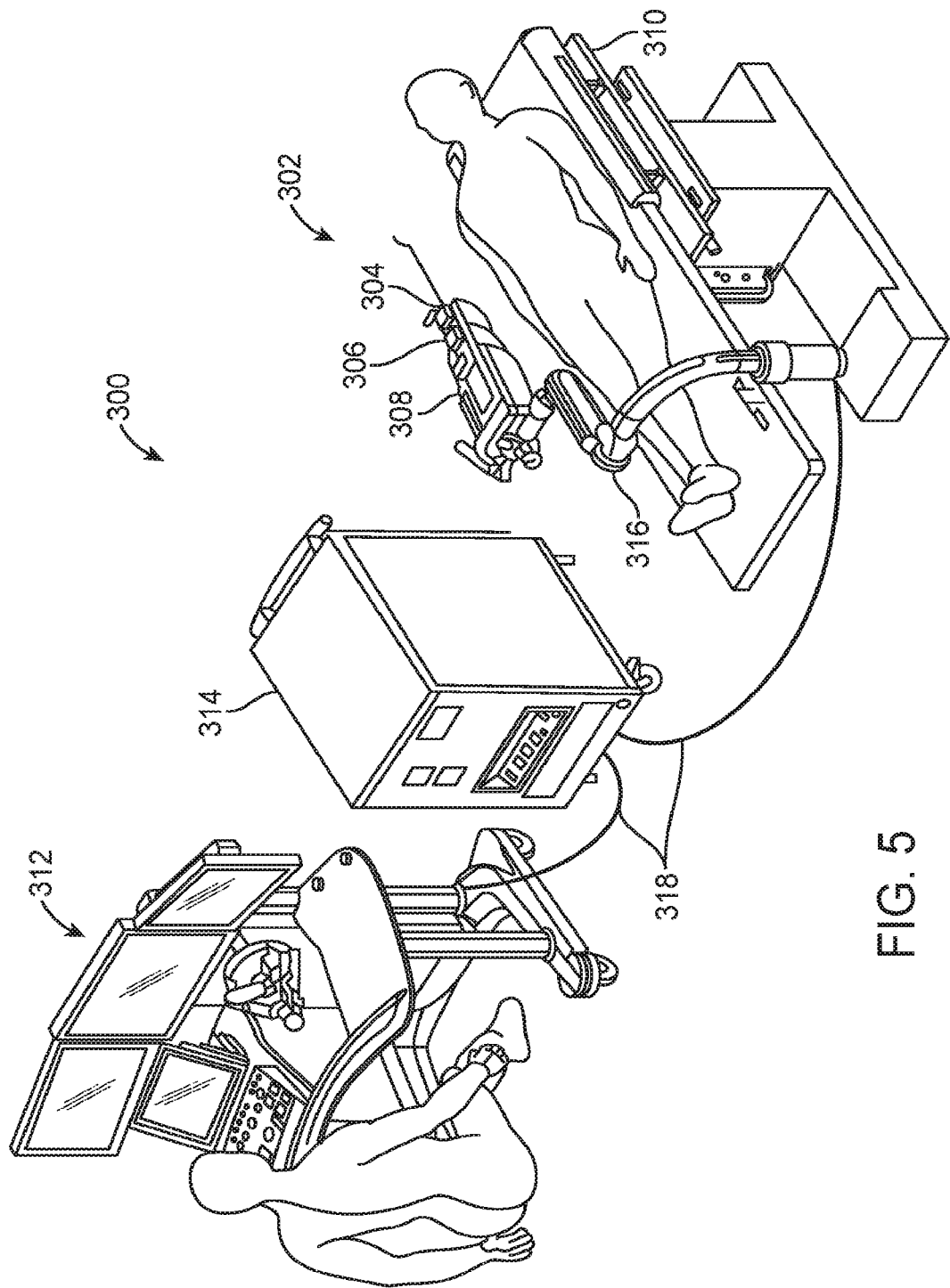
FIG. 5 is a perspective view of a surgical robotic system, in which any of the embodiments described herein may be incorporated.

Referring to FIG. 5, one embodiment of a robotically controlled surgical system 300 is illustrated. System 300 may include a robotic catheter assembly 302, having a first or outer steerable complement, otherwise referred to as a robotic sheath or sheath instrument 304 (also referred to simply as a "sheath") and/or a second or inner steerable component, otherwise referred to as a robotic catheter, guide or catheter instrument 306 (also referred to simply as a "catheter"). Catheter assembly 302 is controllable using a robotic instrument driver 308. During use, a patient is positioned on an operating table or surgical bed 310, to which robotic instrument driver 308 may be coupled or mounted. In the illustrated example, system 300 includes an operator workstation 312, an electronics rack 314 and an associated bedside electronics box (not shown), a setup joint mounting brace 316, and instrument driver 308. A physician (or "operator") sits at operator workstation 312 and can monitor the surgical procedure and patient vitals and control one or more catheter devices. Operator workstation 312 may include a computer monitor to display a three dimensional object, such as a catheter instrument or component thereof, e.g., a guidewire and/or a catheter sheath. In some cases, the catheter instrument may be displayed within, or relative to, a body cavity, organ or portion of an organ, e.g., a chamber of a patient's heart. In one example, the operator uses a computer mouse to move a control point around the display to control the position of the catheter instrument.

System components may be coupled together via cables or other suitable connectors 318 to provide for data communication. In some embodiments, one or more components may be equipped with wireless communication components to reduce or eliminate cables 318. Communication between components may also be implemented over a network or over the Internet. In this manner, a surgeon or other operator may control a surgical instrument while being located away from or remotely from radiation sources (e.g., behind a shield or partition), thereby decreasing radiation exposure. With the option for wireless or networked operation, the surgeon may even be located remotely from the patient in a different room or building.

Figure 6A:
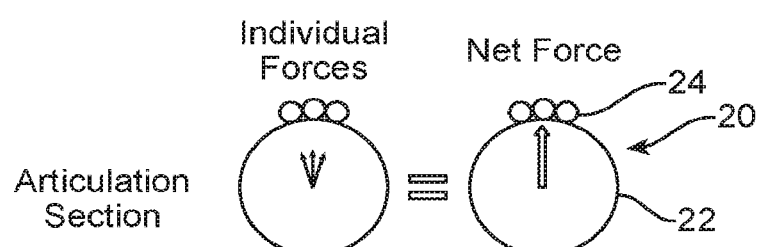
FIGS. 6A-6C are diagrammatic cross-sectional views of a steerable catheter, illustrating one possible configuration for pullwires at various locations along the length of the catheter, according to one embodiment.

I. Localization of Forces and Distribution of Forces—Multi-Directional Single-Bend Catheters Referring to FIGS. 6A-6C, cross-sectional, diagrammatic views of one embodiment of a polyrail catheter 20 are illustrated. FIG. 6A illustrates a cross-section of a catheter 20 having a sidewall 22 and three pullwires 24, taken from a distal articulation section (i.e., distal tip) of the catheter 20. Again, this figure is diagrammatic in nature, as is evident by the fact that the pullwires 24 are shown resting on the outer surface of the sidewall 22, whereas typically they are integrated into the sidewall 22. This simplified representation of the pullwires and sidewall is used in FIGS. 6A-6C and in many subsequent figures described below, for simplicity and ease of understanding. Although pullwires are shown on the exterior/outer surface of the sidewalls in these figures, in actual catheter devices described herein, the pullwires will typically (though not necessarily) be located within the sidewall of a given catheter embodiment.

Figure 6B:
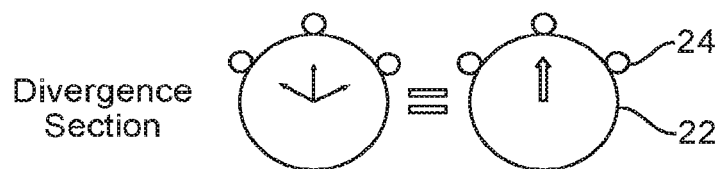
Figure 6C:
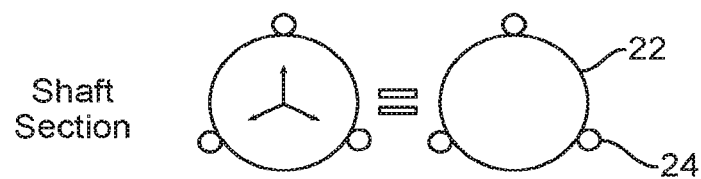

The exemplary embodiment of FIGS. 6A-6C includes only three pullwires 24 and is unidirectional—i.e., articulates in only one direction. This simple example is used here for ease of explanation. FIG. 6B is a cross-sectional view at a middle divergence section of the catheter 20, and FIG. 6C is a cross-sectional view of a more proximal shaft section. This embodiment circumferentially distributes the strain from pullwire tension in the shaft section (FIG. 6C) through a circumferentially spaced placement of the control wires, and then localizes the strain in the articulation section (FIG. 6A). This isolates the proximal shaft section from bending deflection during articulation, without requiring a stiffness gradient along the length of the catheter 20. This creates a more free and open design space, where the catheter stiffness and mechanical properties can be optimized for specific clinical requirements, rather than engineering requirements. Articulation load localization and shaft load distribution can be achieved by using multiple pullwires 24 for one articulation direction, which are circumferentially grouped together in the articulation section (FIG. 6A) and circumferentially distributed in the shaft section (FIG. 6C). Tension applied equally to each pullwire 24 results in a bending moment in the articulation section, while the non-articulating shaft section of the catheter is unaffected.

Again, the cross-sectional views of FIGS. 6A-6C illustrate a three-wire example, with a single articulation direction. In the articulation section (FIG. 6A), all the pullwires 24 are concentrated toward one side, so there is a net bending moment pointing toward the 12 o'clock direction. The magnitude of the bending moment depends on the diameter of the catheter sidewall 22, the distance of the pullwire from the neutral axis and/or the articulation force. In the divergence section (FIG. 6B) of the catheter 20, the pullwires 24 are more distributed but still symmetrical around the 12 o'clock articulation direction. As the pullwires 24 diverge in the divergence section, each of the pullwires 24 creates the same magnitude of bending moment as it did in the articulation section, but the bending moments are now applied in different directions, as shown. Since the pullwires 24 are more distributed but symmetrical around the articulation direction, the components of the bending moment from each of the outside two pullwires 24, which are not in the direction of bending, cancel each other. Thus, there is still a resultant bending moment to the 12 o'clock position, but not as large as in the articulation section.

The pullwires 24 are equally spaced in the proximal shaft section (FIG. 6C), and if equal load is applied to each of the three pullwires 24, the overall combined bending moment is zero. At this point, each pullwire 24 creates its own bending moment, but because the pullwires 24 are uniformly distributed, the net result is zero. Thus, there is no bending moment along the length of the proximal shaft section. The symmetric distribution of forces results in a reduction in shaft muscling. This symmetric distribution of forces means that stiffening the catheter shaft is not necessary to reduce unwanted bending or muscling. The advantage of this design is that the articulation section can be fully defined, meaning completely isolated from the proximal shaft section, without changing the stiffness of either section. The shaft section can remain flexible, such that tracking performance is enhanced and potential trauma to the patient's body is minimized. Using multiple pullwires 24 per articulation direction also increases the effective tensile strength of that direction, enabling the reduction of wire diameter and resulting in overall catheter wall thickness reduction, without compromising safety or risking pullwire failure.

While some catheter embodiments include pullwires that are uniformly spaced in the catheter shaft section, it is not necessary to have uniform distribution, if there are more than two pullwires per group. With two pullwires per group, the wires are preferably 180° apart (i.e., opposite each other) in the shaft, and an equal load should be applied to both wires to ensure load balancing and no bending moment. However, if there are three or more wires per group, the spaced pullwires of the shaft section may not be equally distributed around the circumference. Rather, in some embodiments, the pullwires are spaced around the circumference in a non-equal distribution. The minimum requirement for such an arrangement is that each pullwire is positioned less than 180° away from its two adjacent pullwires (i.e., the pullwires immediately to its left and right). In such embodiments, any applied load must be proportionally distributed among the pullwires, based on the spacing, to ensure the load is distributed evenly. This will be explained further below.

To achieve an omnidirectional articulation section (i.e., an articulation section able to articulate in all directions), at least three groups of pullwires are employed in some embodiments. In some embodiments, for example, each group of pullwires includes three pullwires, which are redistributed in the shaft section to allow for equal load distribution around the circumference of the shaft section. With three pullwires per group and three groups of pullwires, such an omnidirectional catheter embodiment includes nine pullwires. In other embodiments, any suitable number and arrangement of pullwires may be provided.

While the exact pullwire arrangement may vary, each of the catheters described herein includes an articulation section, a divergence section, and a shaft section. The articulation section includes one or more "articulation sets" of pullwires. Each articulation set is formed of multiple pullwires clustered together. As used herein, "clustered together" may mean the pullwires are touching, almost touching, positioned closer to each other than to any other pullwires, or are simply adjacent/neighboring pullwires. When some of or all the pullwires in a given articulation set are tensioned, the articulation section experiences a bending moment in the direction of that set. In omni-directional embodiments, the articulation section of the catheter includes at least three articulation sets of pullwires. If some or all pullwires in a first articulation set are tensioned while no other pullwires are tensioned, the articulation section will experience a bending moment in the direction of the first articulation set. If an equal amount of tension is applied to pullwires in a first articulation set and to pullwires in an adjacent second articulation set, the articulation section will experience a bending moment in a direction half way between the first and second articulation sets. The tension forces applied to one or more articulation sets may be adjusted in order to achieve articulation in any desired direction.

In the shaft section, the pullwires are arranged so as to minimize or eliminate bending moments and resultant compression and torsional forces. That is, the pullwires that formed a given articulation set in the articulation section are substantially distributed around the circumference of the catheter in the shaft section, in order to distribute loads. In some embodiments, the pullwires forming an articulation set are equally distributed around the circumference of the catheter by the time they reach the shaft section. In some embodiments, the pullwires of the shaft section are grouped into multiple "shaft sets." In at least some such embodiments, no pullwires found together in a given articulation set are found together in any given shaft set. That is, the arrangement of pullwires is changed to form different groupings between the articulation section and the shaft section. The pullwires are rearranged into different groupings, so that a tension applied to one articulation set can cause a bending moment in one direction in the articulation section while that same tension can be distributed equally around the circumference of the shaft section (so that the forces in the shaft section cancel each other and no bending moment is experienced in the shaft section).

Between the articulation section and the shaft section is a divergence section in which the positions of the pullwires transition from the arrangement of the articulation sets to the arrangement of the shaft sets. Any suitable means of transitioning may be used. In some embodiments, at least some of the pullwires overlap one another in the divergence section, in order to transition from their distal circumferential positions in the articulation section to their proximal circumferential positions in the shaft section.

Figure 7C:
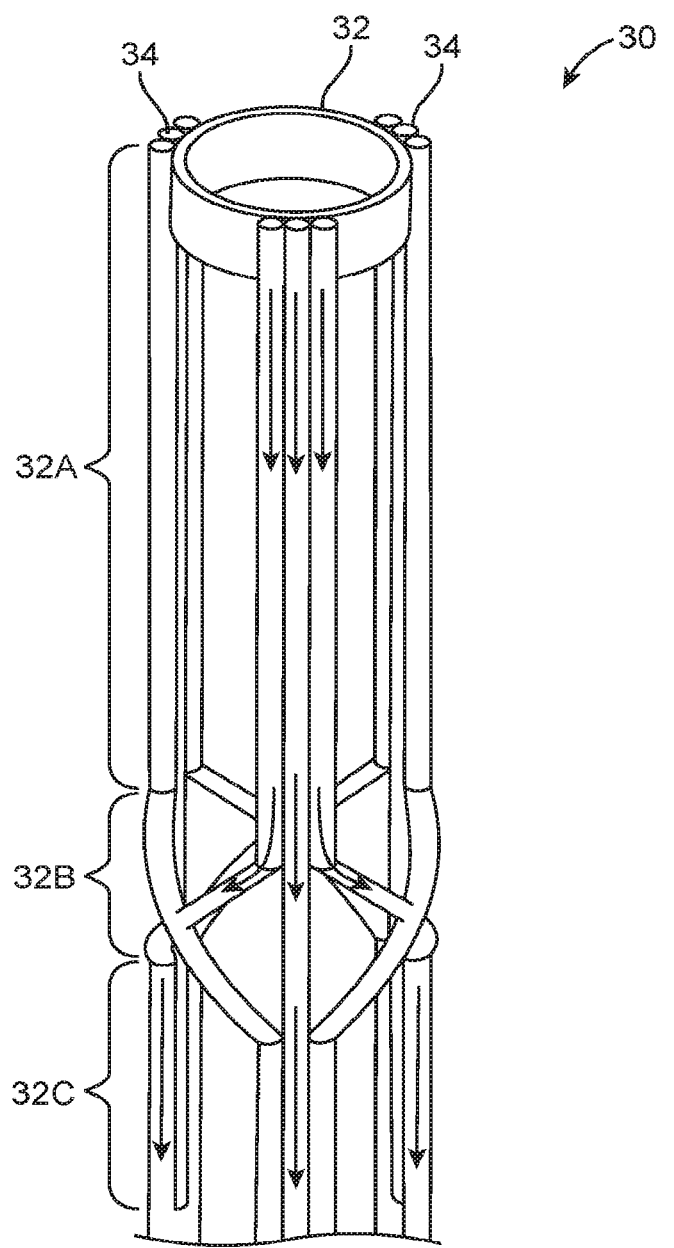
FIG. 7C is a perspective view of a distal portion of the catheter of FIGS. 7A and 7B.

Referring now to FIGS. 7A and 7B, cross-sectional, diagrammatic views of one embodiment of an omnidirectional, nine-wire catheter 30 are shown. FIG. 7C is a perspective view of a distal portion of the same catheter 30, illustrating the articulation section 36A, the divergence section 36B, and a distal portion of the shaft section 36C. The catheter 30 includes a catheter sidewall 32 and three groups of pullwires 34, where each group of pullwires 34 is numbered 1, 2, or 3. In describing this embodiment, the pullwires 34 will be described as belonging to group 1, 2, or 3, and individual pullwires 34 will be described as "pullwire 1*a*," "pullwire 2*b*," and the like. The groups of pullwires 34 may also be referred to, for example, as "articulation set 1" (pullwires 1*a*-1*c*), "articulation set 2" (pullwires 2*a*-2*c*), and "articulation set 3" (pullwires 3*a*-3*c*). The groups of pullwires 34 may also be referred to as "shaft set 1" (pullwires 3*c*, 1*b*, 2*a*), "shaft set 2" (pullwires 1*c*, 2*b*, 3*a*), and "shaft set 3" (pullwires 1*a*, 3*b*, 2*c*).

FIG. 7A is a view taken along the articulation section 36A (or "distal section" or "tip") of the catheter 30, and FIG. 7B is a view taken along the shaft section 36C (or "proximal shaft") of the catheter 30. The numbered pullwires 34 of each group are anchored close together in the articulation section 36A (FIG. 7A), to concentrate or localize the forces in respective isolated areas. In the shaft section 36C (FIG. 7B), the numbered pullwires 34 of each group have diverged and formed new groupings with each of the new groupings having one pullwire 34 from each of the respective numbered groups. This may be referred to as a "polyrail" design, because the shaft load is distributed on multiple "rails."

In the embodiment depicted in FIGS. 7A-7C, one pullwire 34 from each numbered grouping continues straight from the articulation section down to the shaft section. In FIGS. 7A and 7B, those are the pullwires 34 lettered "b" (i.e., 1*b*, 2*b*, and 3*b*). Adjacent pullwires 34, labeled "a" and "c", are switched in the transition from articulation section groupings to shaft section groupings, pullwire 1*a* switches positions with 3*c*, 2*a* switches positions with 1*c*, and 3*a* switches positions with 2*c*. In terms of clock position, pullwire 1*b* has stayed in the 12 o'clock position, 1*c* has been spiraled clockwise on or within the sidewall 32 to the 4 o'clock position, while pullwire 1*a* has spiraled counter clockwise on or within the sidewall 32 to the 8 o'clock position. Likewise, pullwire 2*a* has moved to the 12 o'clock position, pullwire 2*c* has spiraled to the 8 o'clock position, pullwire 3*c* has moved to the 12 o'clock position, and pullwire 3*a* has spiraled to the 4 o'clock position.

If articulation in the 12 o'clock position is desired, pullwire group 1 (or "articulation set 1") will have equal force applied to all three pullwires 34. This results in a net bending moment in the 12 o-clock position in the articulation section, causing the tip to bend toward the 12 o'clock position. For example, if a load of approximately 15 N were required to bend the distal tip of the catheter 30 to a desired angle, a load of 5 N would be placed on each of the pullwires 34 in the group labeled 1*a*-1*c*, and no load would be applied to the pullwires 34 in the groups labeled 2*a*-2*c* and 3*a*-3*c*. In other words, in the articulation section 36A, 15 N is applied at 12 o'clock, 0N is applied at 4 o'clock, and 0 N is applied at 8 o'clock. In the shaft section 36C, however, 5 N will be applied at 12 o'clock, 5 N will be applied at 4 o'clock and 5 N will be applied at 8 o'clock. Therefore, there will be no net bending moment in the shaft section 36C, because there is equal force being applied over equally spaced wires.

Although the examples illustrated in FIGS. 6A-6C and 7A-7C include three pullwires per group, the minimum number of pullwires necessary to achieve shaft load distribution and articulation load localization is two wires per group. Therefore, some embodiments may include as few as six pullwires, while still remaining omnidirectional.

FIGS. 8A and 8B are cross-sectional, diagrammatic views of one embodiment of an omnidirectional catheter 40 that includes a catheter sidewall 42 and six pullwires 44. As in FIGS. 7A and 7B, the pullwires 44 in this catheter 40 are labeled in groups by a number (numbers 1-3), and pullwires 44 within a group are differentiated by letter (letter "a" or "b"). In this embodiment, pullwires 1*a* and 1*b* are adjacent to each other in the articulation section (FIG. 8A) and opposite each other in the shaft section (FIG. 8B). Likewise, pullwires 2*a* and 2*b* are adjacent to each other in the articulation section and opposite each other in the shaft section. The same is true of pullwires 3*a* and 3*b*. Thus, if tension is applied only to pullwire group 1, for example, if pullwires 1*a* and 1*b* are equally tensioned, the articulation section will experience articulation in the 12 o'clock direction.

Figure 9A:
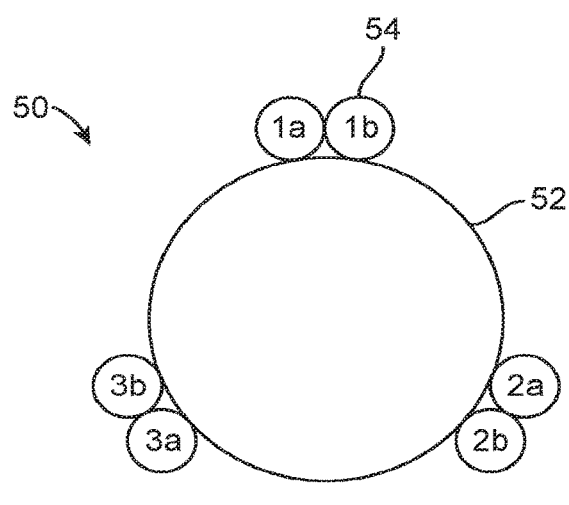
FIGS. 9A and 9B are diagrammatic cross-sectional views of a steerable, six-pullwire catheter, illustrating one possible configuration for pullwires along a distal articulation section (FIG. 9A) and a proximal shaft section (FIG. 9B) of the catheter, according to an alternative embodiment.
Figure 9B:
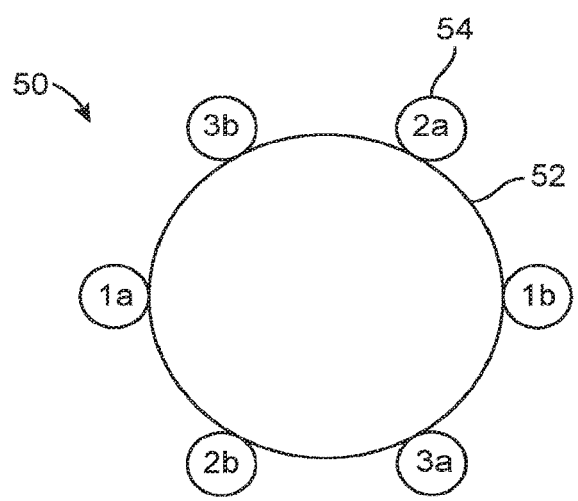

Referring now to FIGS. 9A and 9B, an alternative embodiment of a six-pullwire, omnidirectional catheter 50 is illustrated in cross-section, again having six pullwires 54 and a catheter sidewall 52. In this embodiment, the pullwires 54 have the same configuration along the proximal shaft section (FIG. 9B) as they did in FIG. 8B. Along the articulation/tip section (FIG. 9A), however, the two pullwires 54 in each group (groups 1-3) come together to touch or nearly touch one another. Thus, in various embodiments, pullwires said to be grouped or clustered together in the articulation section may be touching, nearly touching, positioned closer to each other than to any other pullwires, or simply located in adjacent positions. The same is true for pullwires grouped or clustered together in the shaft section.

As described above, some embodiments of "polyrail" catheters may include three groups of pullwires, to achieve omnidirectional articulation of the catheter tip without rotating the shaft. In alternative embodiments, however, polyrail catheters may include four or more groups of pullwires. Alternatively, some embodiments may include two groups, or even just one group, of pullwires, for example in embodiments where it is not required to have omnidirectional articulation or where it is possible to rotate the catheter tip via other means.

Figure 10A:
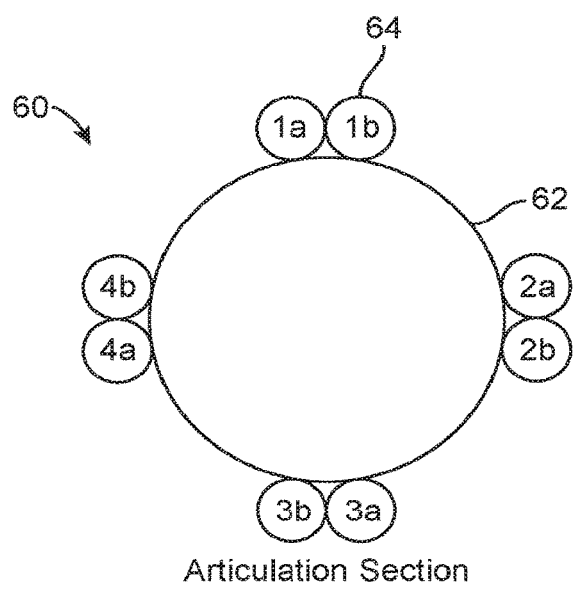
FIGS. 10A and 10B are diagrammatic cross-sectional views of a steerable, eight-pullwire catheter, illustrating one possible configuration for pullwires along a distal articulation section (FIG. 10A) and a proximal shaft section (FIG. 10B) of the catheter, according to one embodiment.
Figure 10B:
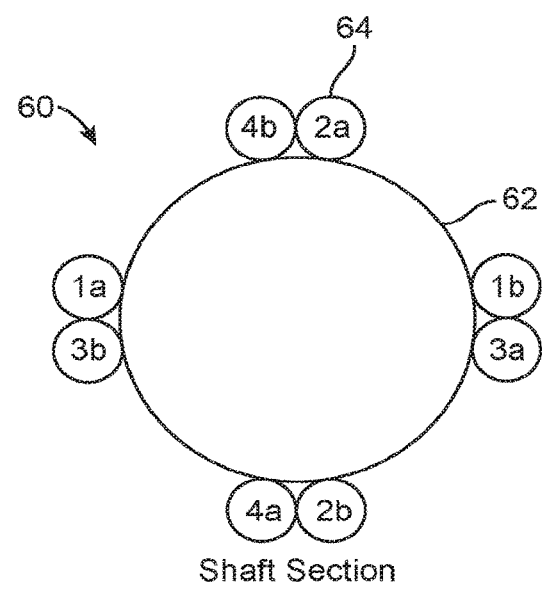

FIGS. 10A and 10B illustrate one embodiment of a polyrail catheter 60, having a catheter sidewall 62 and four groups of two pullwires 64. Each of the two pullwires 64 clustered within a group (e.g., located next to one another) along the articulation section (FIG. 10A) are located across the shaft 62 from one another along the shaft section (FIG. 10B).

Figure 11A:
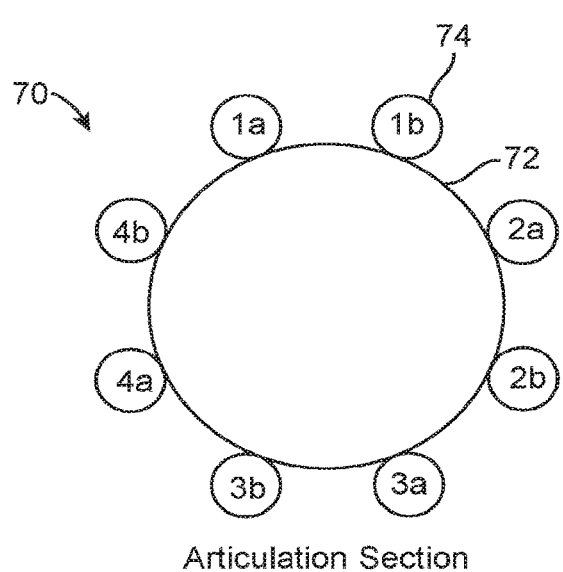
FIGS. 11A and 11B are diagrammatic cross-sectional views of a steerable, eight-pullwire catheter, illustrating one possible configuration for pullwires along a distal articulation section (FIG. 11A) and a proximal shaft section (FIG. 11B) of the catheter, according to an alternative embodiment.
Figure 11B:
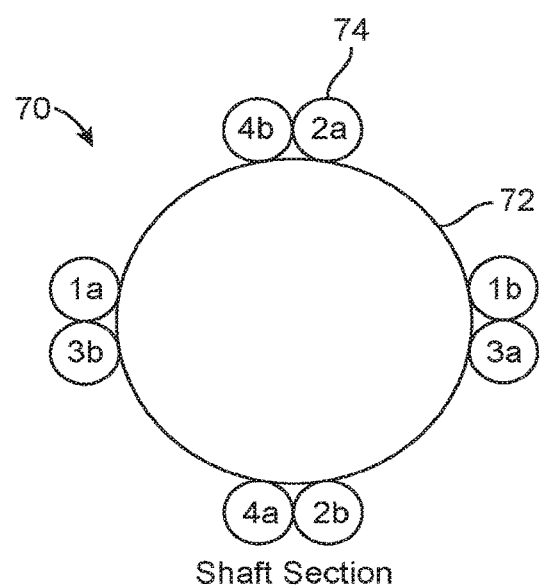

FIGS. 11A and 11B illustrate an alternative embodiment of a polyrail catheter 70, having a catheter sidewall 72 and four groups of two pullwires 74. In this embodiment, the two pullwires 74 clustered together within an articulation section group are located across the shaft 72 from one another along the shaft section (FIG. 11B), as in FIG. 10B. In this embodiment, however, the configuration of the articulation section (FIG. 11A) is different. In the articulation section, the two pullwires 74 of each articulation section group are located farther from one another than they were in the articulation section of FIG. 10A. In other words, the pullwires 74 of each group in the articulation section are separate from one another and not touching one another.

FIGS. 12A and 12B illustrate yet another alternative embodiment of a polyrail catheter 80, having a catheter sidewall 82 and four groups of three pullwires 84 each (twelve pullwires 84 in total). In this embodiment, the three pullwires 84 within an articulation section group are located next to one another along the articulation section (FIG. 12A) and are significantly distributed from one another along the shaft section (FIG. 12B). In some embodiments, the three pullwires 84 of an articulation section group are equally distributed around the circumference of the catheter 80 in the shaft section, such that there are 120 degrees between each pullwire of the group.

The three pullwires 84 within an articulation section group do not necessarily need to be uniformly positioned within the shaft section. Although some embodiments include a uniform distribution, sometimes a uniform distribution may not be possible, due to the position of other pullwires, as shown in FIG. 12B. In such embodiments, the pullwires of an articulation section group are widely distributed within the shaft section, and the load placed on each pullwire is adjusted based on its angular position, to achieve equal load distribution around the shaft section.

Figure 13:
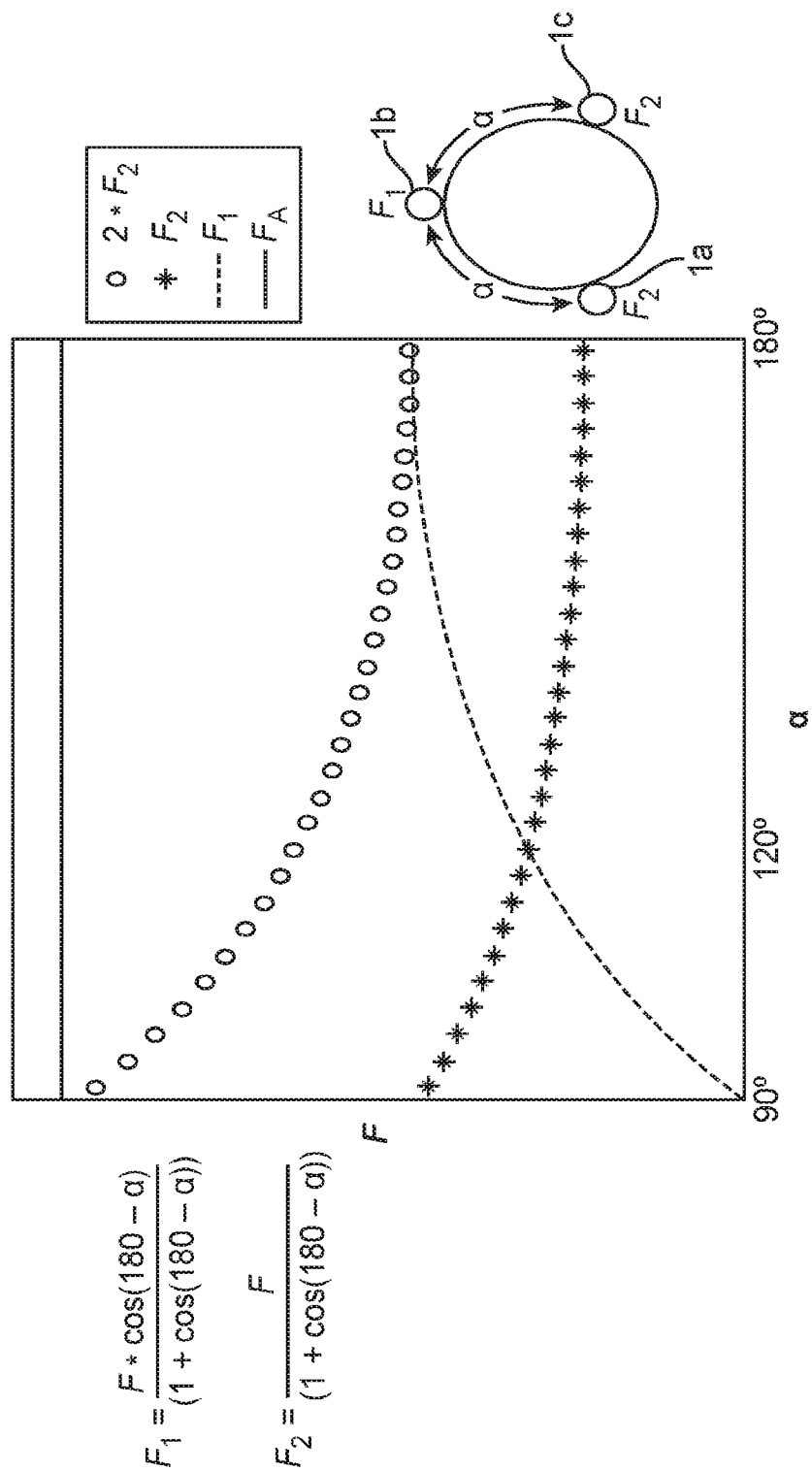
FIG. 13 is a chart, illustrating forces applied to a catheter by pullwires, according to one embodiment.

Referring now to FIG. 13, an equation that relates the load on each pullwire (1a, 1b, 1c) to its angular position on the circumference of the shaft section of a catheter 320 will now be described. For ease of reference, pullwire 1b is positioned at 12 o'clock, and the other two pullwires 1a, 1c are positioned α degrees to either side of pullwire 1b. The overall force applied to the catheter 320 is F. This force is divided among all three pullwires. The force on pullwire 1b is labeled F1, and the force on pullwire 1a and pullwire 1c is labelled F2. If α=120 degrees, and F=15 N, then the force of 15 N is applied equally on the three pullwires (F1 and F2=5 N), to ensure no bending moment in the shaft.

When three pullwires are present, if α=90 degrees or less, then the design does not work. It is not possible to distribute the forces uniformly in the shaft. α must be greater than 90 degrees for the load to be adequately distributed in the shaft section. α cannot be greater than 180 degrees in the embodiment shown, because then pullwire 1a becomes pullwire 1c, and pullwire 1c becomes pullwire 1a. The relationship between F1 and F2 for all three pullwires as α goes from 90 degrees to 180 degrees is shown diagrammatically in the graph 322 of FIG. 13. On the left side of the graph 322, F1 is zero and F2=F/2. This is essentially a two-pullwire design. There is no load applied to pullwire 1b, and the load is shared equally between pullwires 1a and 1c. When α increases to 120 degrees, F2=F1, as shown by the intersection of the dashed line and the starred line. In such arrangements, there is uniform tension on all pullwires. As α continues to increase towards 180 degrees, F2 decreases towards F/4 and F1 increases toward F/2. Therefore, even if all pullwires are not uniformly distributed, but instead, two pullwires are offset an angle α from the first pullwire 1b, a force may be proportionally applied to each pullwire, such that a uniform load is applied to the shaft. The equations for the force F1 to be applied to pullwire 1b and for the force F2 to be applied to pullwire 1a and 1c, in order to uniformly distribute load about the circumference of the shaft section, are depicted in FIG. 13.

Referring back to FIG. 12B, pullwire 1b is in the 12 o'clock position, pullwire 1c is in the 3:30 position, and pullwire 1a is in the 8:30 position. Therefore, there are 105 degrees between pullwires 1b and 1c in the shaft section, 105 degrees between pullwires 1b and 1a in the shaft section, and 150 degrees between pullwires 1a and 1c in the shaft section. Therefore α=105 degrees, and substituting α into the above described equations, the 15 N is distributed and applied as follows: F2=5.958 N on pullwire 1a, F2=5.958 N on pullwire 1c, and F1=3.084 N on pullwire 1b.

Figure 14A:
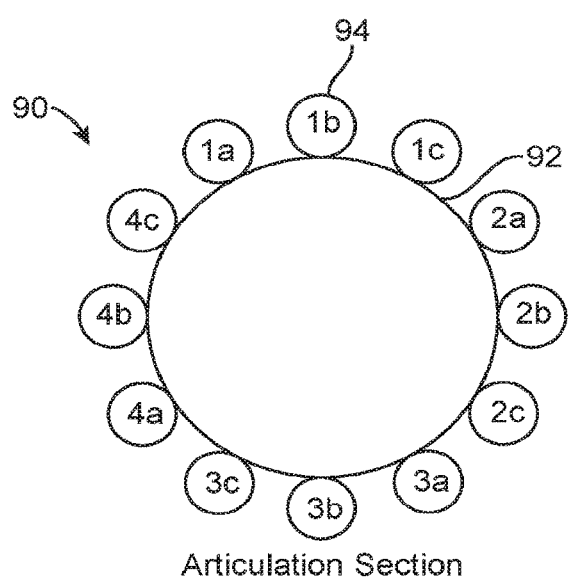
FIGS. 14A and 14B are diagrammatic cross-sectional views of a steerable, twelve-pullwire catheter, illustrating one possible configuration for pullwires along a distal articulation section (FIG. 14A) and a proximal shaft section (FIG. 14B) of the catheter, according to an alternative embodiment.
Figure 14B:
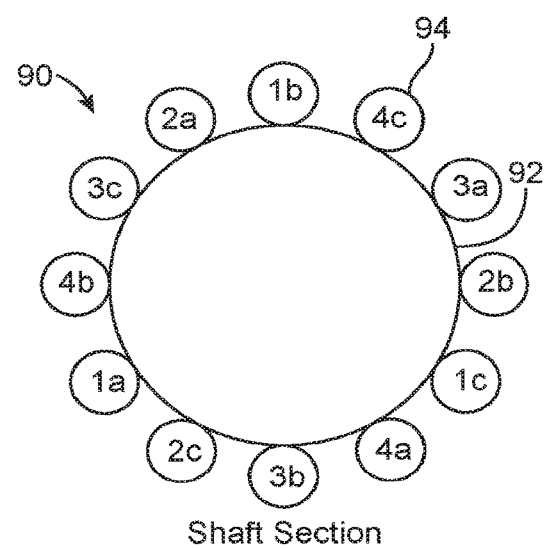

FIGS. 14A and 14B illustrate yet another alternative embodiment of a polyrail catheter 90, having a catheter sidewall 92 and four groups of three pullwires 94. In this embodiment, the three pullwires 94 in each articulation section group are spaced equidistant from one another around the circumference of the catheter along the shaft section (FIG. 14B) and are clustered close to one another (but not touching one another) along the articulation section (FIG. 14A).

As described above, the catheter embodiments disclosed in this application generally include a distal articulation section (or "catheter tip," "distal portion" or other similar terms) and a shaft section (or "proximal shaft portion" or other similar terms). The catheters also typically include a "divergence section" or "transition section," where the pullwires transition from their arrangement along the shaft section to their arrangement along the articulation section. The location of the transition identifies the transition between the shaft and the articulation section of the catheter. This may vary along the catheter. The length of the transition or divergence section may also vary. Typical articulating catheters have a relatively short articulation section, compared to the overall length of the catheter. Thus, a typical transition section is located close to the distal end of the catheter. Alternatively, however, the transition section may be positioned at any location along the catheter length, since the lengths of the shaft and the articulation section may also vary between designs. Some embodiments may even include multiple transition sections along the catheter length, as will be described further below.

Referring again to FIGS. 2A and 2B, a straight catheter is shown with the dashed outline. When a steering wire (i.e., pullwire or control wire) is pulled, a traditional catheter 10, with a soft trackable shaft, would deflect, as shown in FIG. 2A. A traditional catheter 10 with a stiff shaft is shown in FIG. 2B. The embodiment in FIG. 2B would generally be preferred, from an articulation perspective, because it produces predictable articulation. A catheter 10 with a stiff shaft, however, will not track through tortuous anatomy. An articulation shape like the one illustrated in FIG. 2B, however, is achievable with the polyrail catheters described herein, even with a soft, flexible, and trackable shaft.

In addition to eliminating unwanted shaft deflection, the polyrail catheter embodiments described herein isolate the articulation section without varying stiffness. Traditional catheter designs identify the articulation section from the shaft by making the articulation section soft and the shaft section stiffer. The polyrail catheter allows architectures to be better optimized for other performance properties, such as tracking, push-ability and reaching clinical targets.

The polyrail design ensures that the group of pullwires required to articulate the articulation section of the catheter in one direction is significantly distributed around the catheter shaft section, to ensure that the shaft does not undergo any unintended bending moment. As described above, preventing any unintended bending moment requires that an equal force (or a force proportionate to the spacing of non-equally spaced pullwires) be applied to each of the pullwires. One design for accomplishing the application of equal force is to attach all pullwires from one group to the same pulley in the splayer. In other words, in such an embodiment, each group of pullwires is attached at or near one anchor point at the distal end of the catheter, then they diverge to be widely distributed around the catheter in the shaft section, and then they converge to one anchored location at the proximal end at the pulley.

While this design works well if the entire shaft is held straight, it may not work well when the catheter is bent. For a bent catheter, any pullwires positioned in lumens on the inside of the bend will be compressed and have excess slack, whereas any pullwires in lumens on the outside of the catheter will be stretched and have increased tension. Therefore, if all pullwires are attached to one pulley and an articulation command is initiated, the pullwire(s) on the outside of the bend will take more of the load than the pullwire(s) on the inside, because the outside pullwires have a higher initial tension. If the pullwires spread around the shaft do not take an equal (or spacing-proportionate) load, then this design will not work as intended.

II. Interface Design for Manipulating Pullwires

It is important that each pullwire within a set of pullwires have the intended force applied to it, such that the force is truly distributed in the shaft as articulation is commanded. This is especially important as the catheter is put into different tortuosity and bends. As the catheter is put into a bend, the material on the inside of the catheter will compress (shorten) and the material on the outside of the bend will stretch (lengthen). However, the length of the pullwires will remain unchanged, because they are floating (i.e., unconstrained) within the walls of the catheter. That is, rather than compressing or stretching, the pullwires will slide further into, or partially out of, the proximal end of the catheter. Since the proximal end of each pullwire remains attached to a pulley or other control means, this sliding results in slack along the pullwires on the inside of the bend and additional tension on the pullwires on the outside of the bend. For example, if the shaft section of the catheter shown in FIGS. 11A and 11B were bent towards the 12 o'clock direction, the tension on pullwires 4b and 2a would decrease, and the tension on pullwires 4a and 2b would increase.

Figures 15A, 15B:
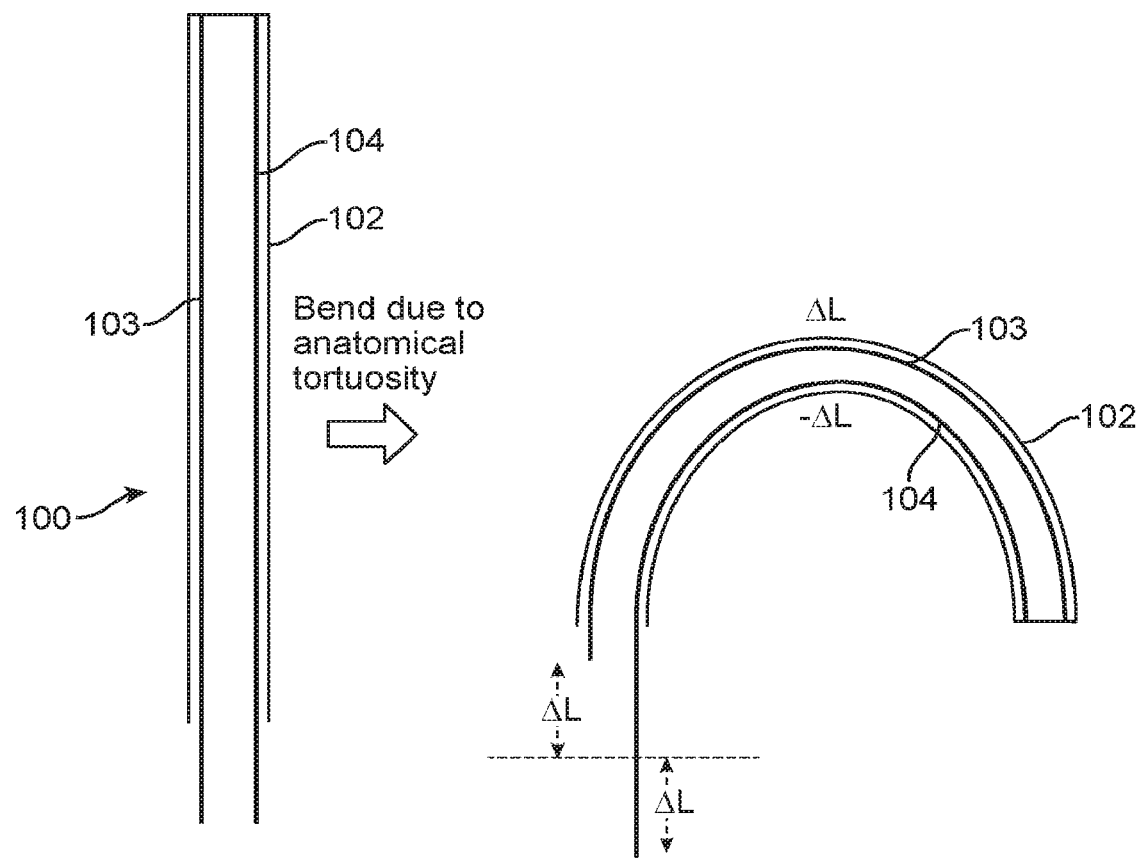
FIGS. 15A and 15B are diagrammatic representations of a steerable catheter embodiment being deformed due to tortuous anatomy; also illustrated is the changing tension and slack experienced by the pullwires as a result.

FIGS. 15A and 15B represent the above-described phenomenon diagrammatically. A catheter 100 with a shaft 102 and two pullwires 103, 104 is illustrated. When the shaft section of the catheter 100 is bent, as in FIG. 15B, a first pullwire 103 tends to slide inward (by $\Delta L$) while remaining attached to a pulley or other attachment point at a proximal end (not shown), and thus, will experience increased tension. A second pullwire 104 tends to slide outward (by $\Delta L$) while remaining attached to a pulley or other attachment point at a proximal end (not shown), and thus, experiences decreased tension or slack.

A. Multiple Pulley and Shared Pulley Embodiments

One way to account for the need for an equal amount of tension (or a carefully controlled amount of tension) on multiple pullwires is by having each pullwire fixed to its own pulley assembly, containing a pulley, torque sensor, and motor. Such an embodiment allows torque sensors to measure the load on each pullwire in a set and adjust the angular displacement of the pulley, such that the force on all pullwires within the set is equal to a commanded force. In such embodiments, the 6, 8, 9, and 12-wire designs require 6, 8, 9, and 12 pulley assemblies, respectively. Ideally, however, a catheter design would not require such a large number of pulley assemblies, due to the complexity, weight and size of an instrument driver having so many pulleys. For example, an instrument driver of a surgical robotic system will have a limited number of motors for driving such pulley assemblies, due to size constraints on the instrument driver at a patient's bedside. To reduce the number of motors required by the robotic system, an alternative actuation method may be implemented.

One simple actuation method used in some embodiments involves fixing each pullwire in a group to the same pulley. Doing this requires the pullwires to either be made of an elastic material or have elasticity added, for example by attaching an extension or torsion spring in series with it. Without an elastic pullwire, when the first pullwire within a group initially has tension applied to it, it will have to elongate an amount equal to the amount of slack in the loosest pullwire in the group before both pullwires are applying load. If a pullwire has an effective spring constant of k, and the amount of slack in the loosest pullwire when the first pullwire is initially tensioned is equal to $\Delta L$, then the difference in force between the two pullwires will be $\Delta L * k$. Given the modulus of elasticity for a typical high-tensile pullwire, the first pullwire may break before the other pullwires in the group gain tension, and if it does not break, there will be a large difference in force between the pullwires. This will result in an unequal load distribution around the circumference and suboptimal polyrail performance.

If a low enough k value for the pullwire is chosen by using pullwires with high elasticity, the issue of unequal load distribution is reduced, however possibly at the cost of tensile strength. Rather than using elastic wires as pullwires, an extension spring may be soldered, welded, or fixed to the proximal end of each pullwire, such that a high tensile wire can be used for tensile strength and a very low k value can still be achieved.

B. Whiffletree Embodiments

Figure 16A:
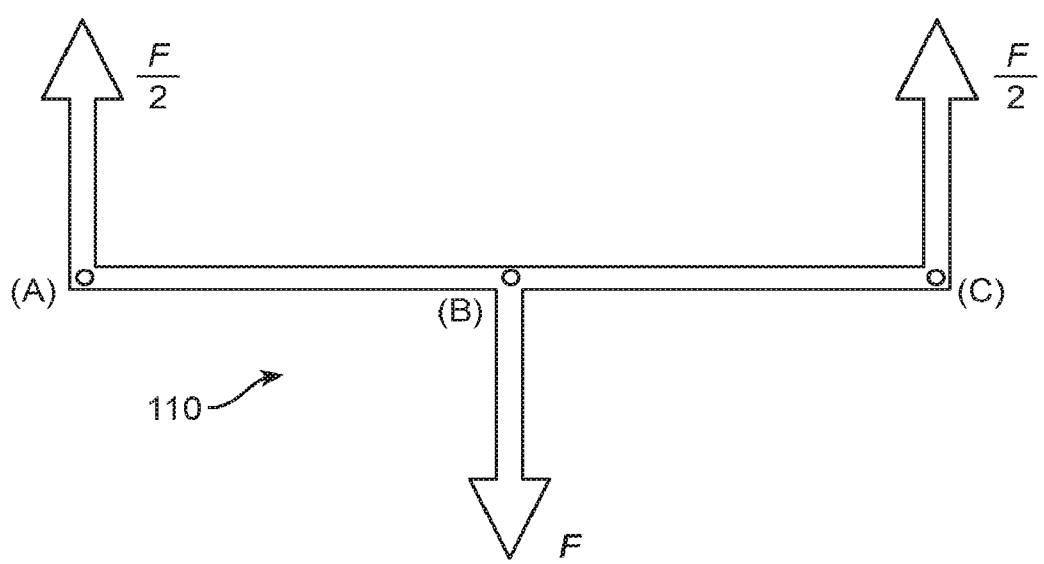
FIGS. 16A and 16B are diagrammatic illustrations of a two-way whiffletree load balancing mechanism, according to one embodiment.
Figure 16B:
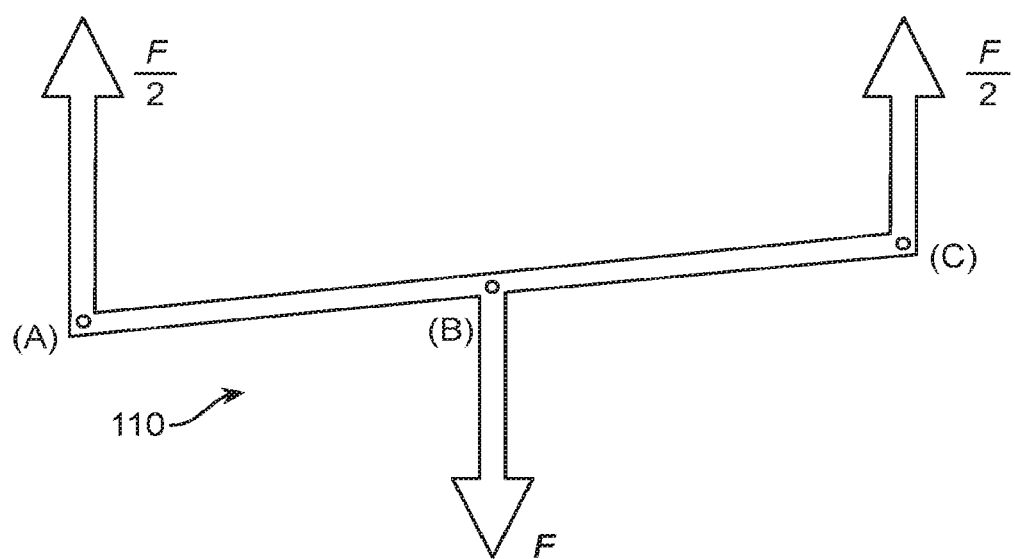

In some embodiments, another actuation method can be implemented in the form of a load balancing mechanism. Referring now to FIGS. 16A and 16B, in one embodiment, a load balancing mechanism in the form of a two-way whiffletree 110 may be employed. This two-way whiffletree 110 is illustrated diagrammatically in FIG. 16A. This mechanism may be used to distribute the forces in any polyrail catheter embodiment that includes two pullwires per pullwire group (for example, the embodiments illustrated in FIGS. 8A-11B). This is done by fixing the two pullwires in a group to opposite ends of a rod with a third wire fixed at the center of the rod extending to the pulley. A free body diagram is shown in FIG. 16A, where the upward pointing arrows 111, 112 represent the tensioned pullwires going into the catheter, and the downward pointing arrow 113 represents the wire fixed to a pulley or linear actuator. Points (A), (B) and (C) are free to pivot, such that when a pullwire path length changes, the rod rotates about point (B) to compensate, as shown in FIG. 16B. If equal force is desired on each pullwire, it is important that point (B) be located an equal distance away from point (A) and point (C). If it is preferred that one pullwire have more load applied to it, however, then point (B) should be located closer to that pullwire. This would be the case, for example, with a three-way whiffletree used for a polyrail embodiment including three pullwires per set (for example, the embodiments in FIGS. 7A-7C, 12A-12B and 14A-14B).

Figure 17:
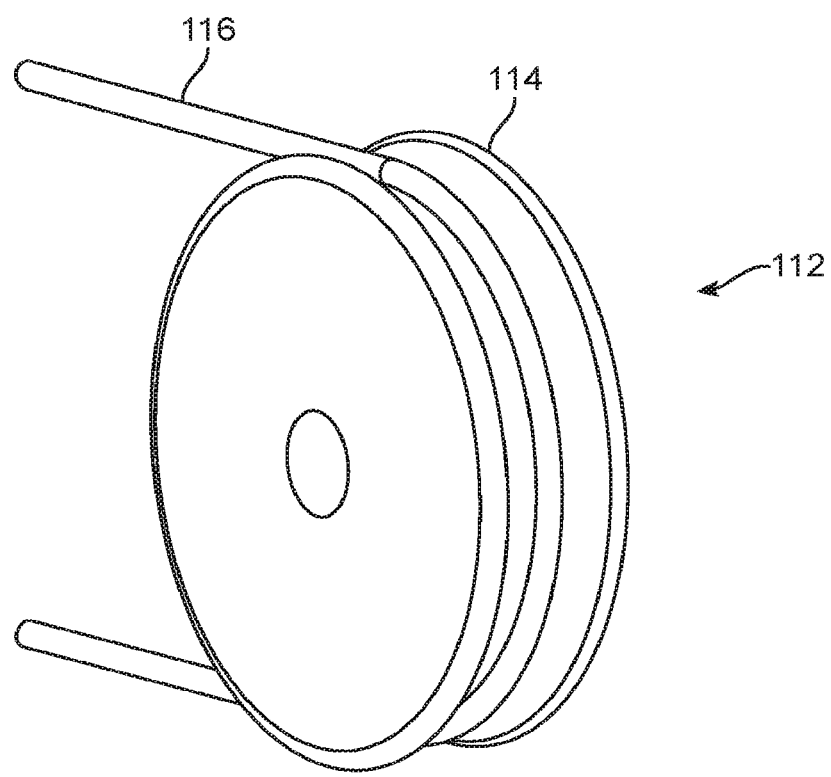
FIG. 17 is a perspective view of a load balancing mechanism including a spool and a continuous pullwire, according to one embodiment.

Referring now to FIG. 17, an alternative embodiment for a load balancing mechanism 114 is illustrated diagrammatically. Load balancing mechanism 114 may include a spool 115 (or "disc") and a continuous pullwire 116 that is one piece but acts as two pullwires. Load balancing mechanism 114 may be used to distribute the forces in any polyrail catheter embodiment that includes two pullwires per pullwire group. The two pullwires of each group may actually take the form of the one continuous pullwire 116, looped around spool 115. Alternatively, two individual pullwires may be attached together and looped around spool 115. Spool 115 is configured such that it may be pulled by the pulley in the splayer (not shown in FIG. 17). As tension increases when the pulley is rotated, spool 115 may rotate such that both ends of continuous pullwire 116 have equal tension.

Figure 18A:
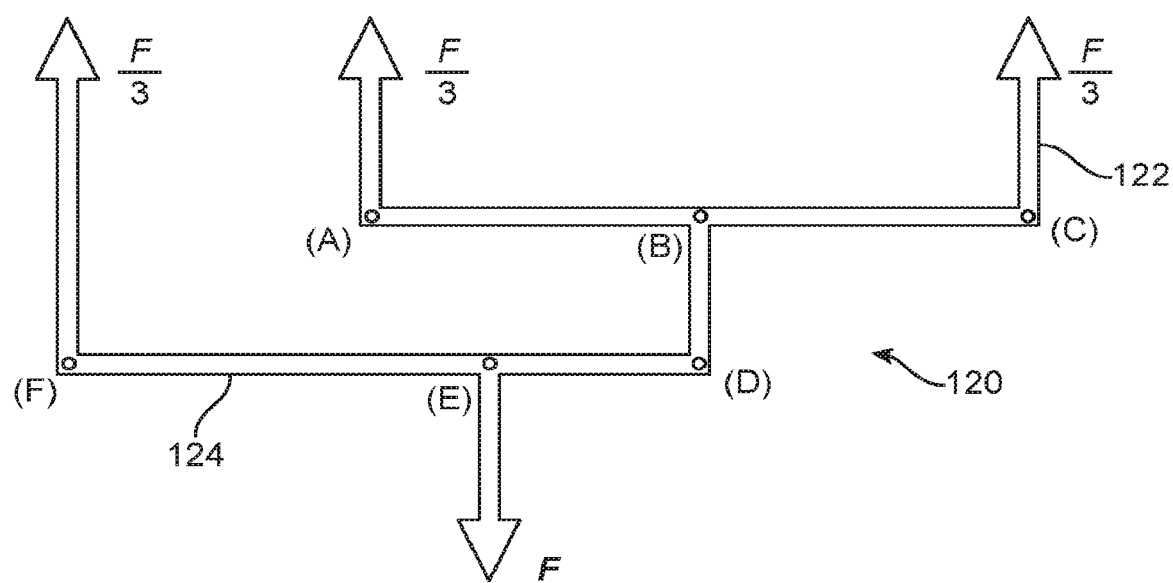
FIGS. 18A and 18B are diagrammatic illustrations of a three-way whiffletree load balancing mechanism, according to one embodiment.
Figure 18B:
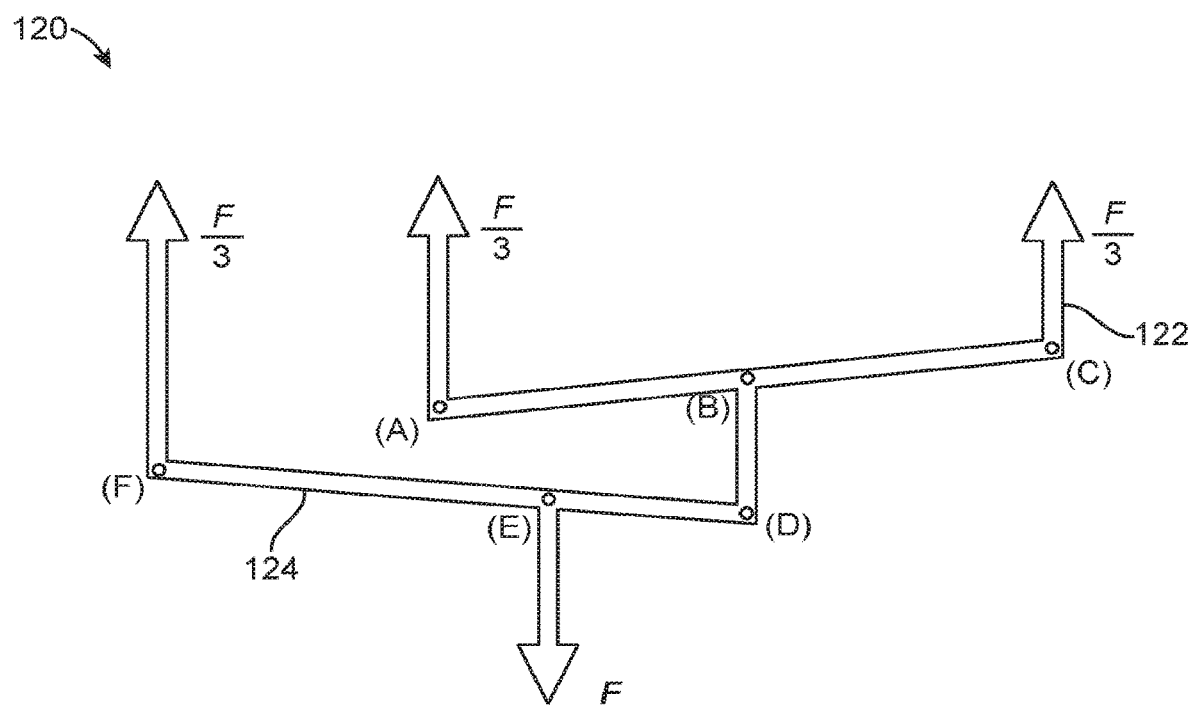
Figure 19:
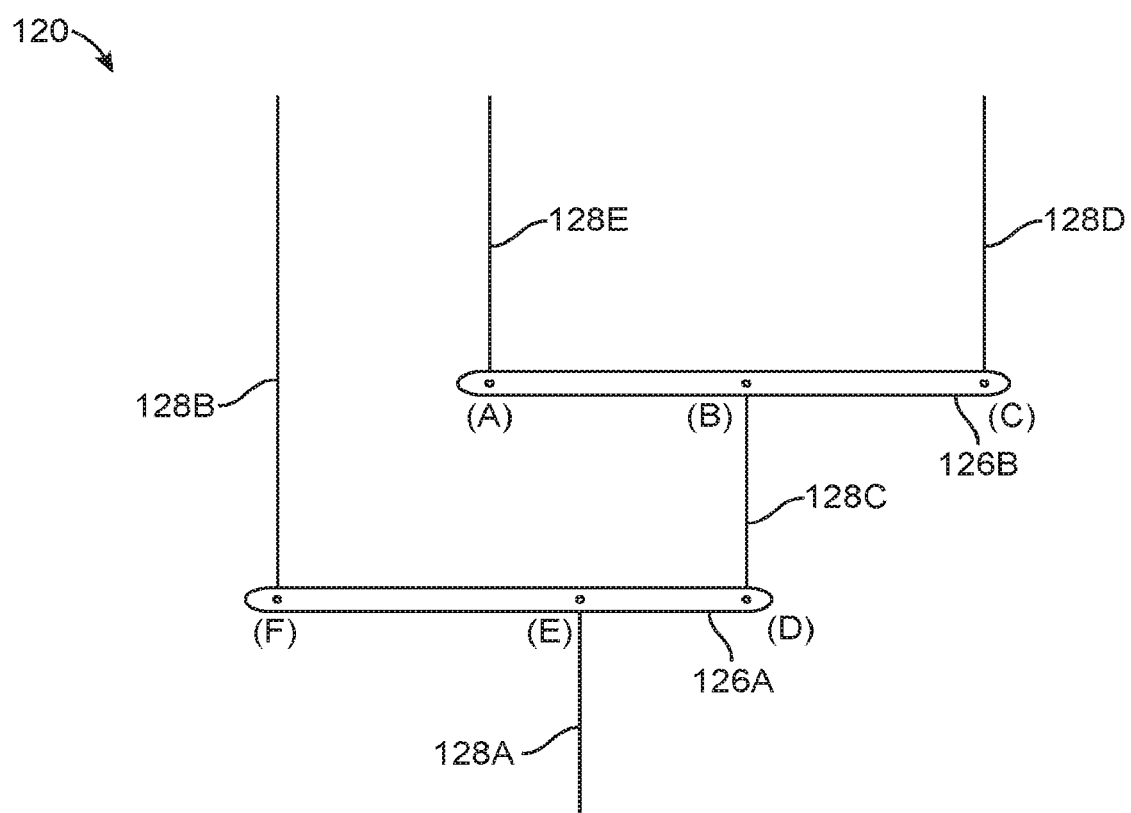
FIG. 19 is a diagrammatic illustration of another three-way whiffletree load balancing mechanism.

Referring now to FIGS. 18A, 18B, and 19, a three-way whiffletree 120 may include two whiffletrees—one unbiased (i.e., balanced) whiffletree 122, as in FIGS. 16A and 16B, and one biased whiffletree 124. FIGS. 16A and 16B depict a free body diagram of the three-way whiffletree 120. FIG. 16 is a front view of one embodiment of a three-way whiffletree assembly 120, which includes two rods 126A, 126B attached to five wires 128A-128E.

Wires 128B, 128E, and 128D represent pullwires in the catheter and are fixed at locations F, A, and C, such that they can pivot about their fixed locations. Force is applied to the entire assembly 120 at location E. A wire or linkage 128C also extends between locations B and D and can pivot about those points as well. When location E is actuated, the assembly 120 will adjust itself, such that loads applied to pullwires 128B, 128E, and 128D at locations F, A, and C are equal. Pullwires 128E and 128D at locations A and C are equal, because they are a part of the unbiased whiffletree 122 (location B is the same distance from point A as from point C). Pullwire 128B and linkage 128C at locations F and D are a part of the biased whiffletree 124 and have unequal load applied to them, because point E is closer to point D than to point F. If the distance between point E and D is half of the distance between point F and point E, then the wire/linkage 128C fixed at point D has twice the leverage as the pullwire 128B at point F. This balances the load from the unbiased whiffletree, with load applied at point F.

The loads applied at points F, A, and C do not need to be split equally either. For example, if the pullwires in a group of the nine-wire design of FIGS. 7A-7C are not equally spaced, the whiffletree could be designed such that the load is still equally distributed. If instead of pullwires 1a and 1c being located 120 degrees from pullwire 1b in the shaft, they are 100 degrees apart, and load is still equally applied to all three, there will be unwanted shaft deflection in the 12 o'clock direction. To solve this, the whiffletree of some embodiments is biased, such that pullwires 1a and 1c are fixed at points A and C, and point E is located such that point F receives slightly more load (E is moved closer to F than depicted in FIGS. 18A and 18B but still not closer than point E to D). The non-uniform distribution of the pullwires within each group in FIG. 12B would also require a similar whiffletree design such that a non-uniform load is applied to each pullwire so that the overall load is still equally distributed on the shaft.

Figure 20A:
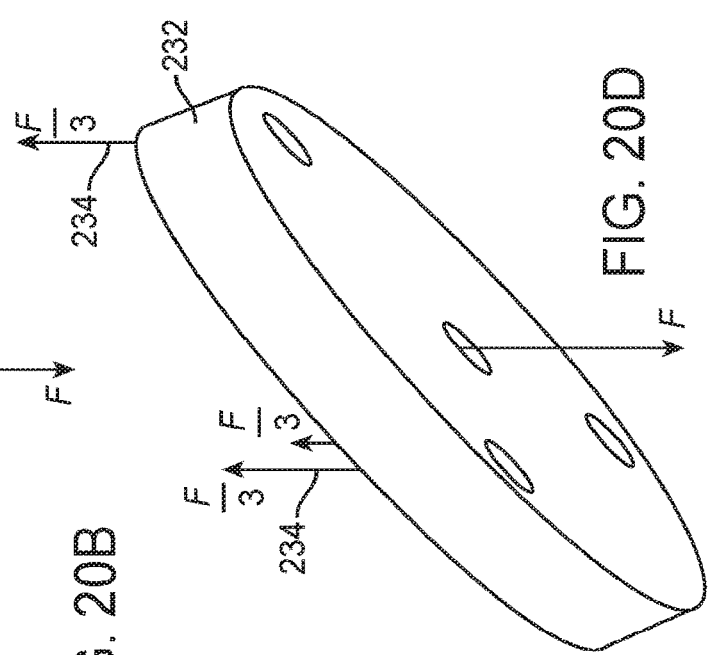
FIGS. 20A-20D are perspective views of a disc-based load balancing mechanism, illustrated in different positions, according to one embodiment.
Figure 20B:
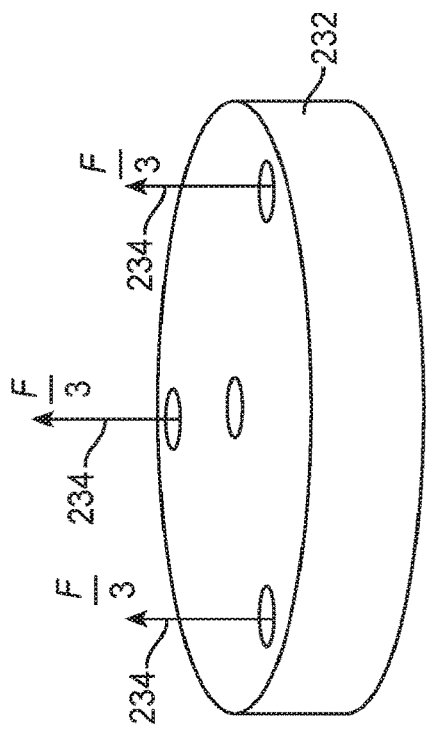
Figure 20C:
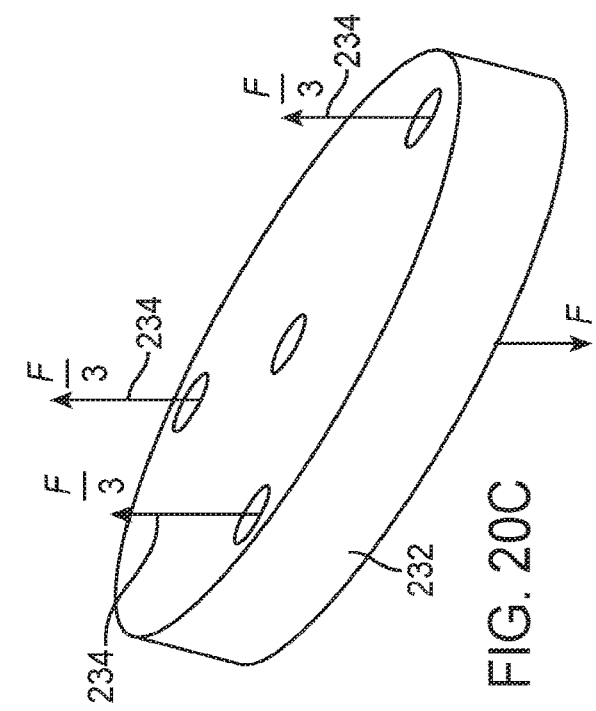
Figure 20D:
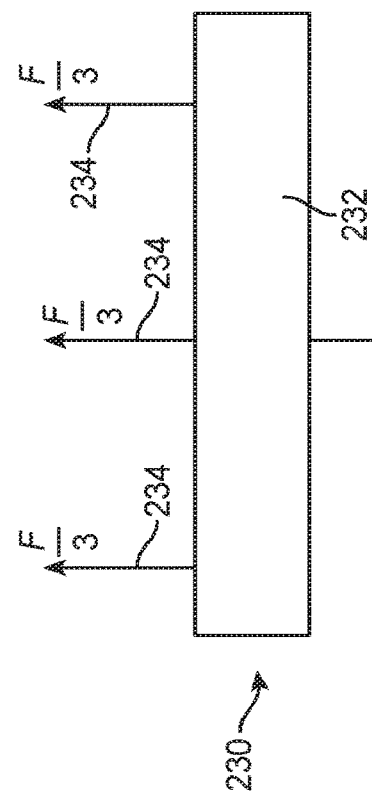

Referring now to FIGS. 20A-20D, another alternative embodiment of a three-way load balancing mechanism 230 is illustrated diagrammatically. The illustrated mechanism 230 may include a disc 232, coupled with three pullwires 234, and it may be used to distribute the forces in any polyrail catheter embodiment that includes three pullwires 234 per pullwire group. The three pullwires 234 may be attached at different points near the circumference of the disc 232. If all three pullwires 234 are equal length, then the disc 232 will be maintained in a straight configuration, as shown in FIG. 20A. If the pullwires 234 become unbalanced, then the disc 232 tilts or pivots about its central axis to compensate and balance the load.

Figure 21:
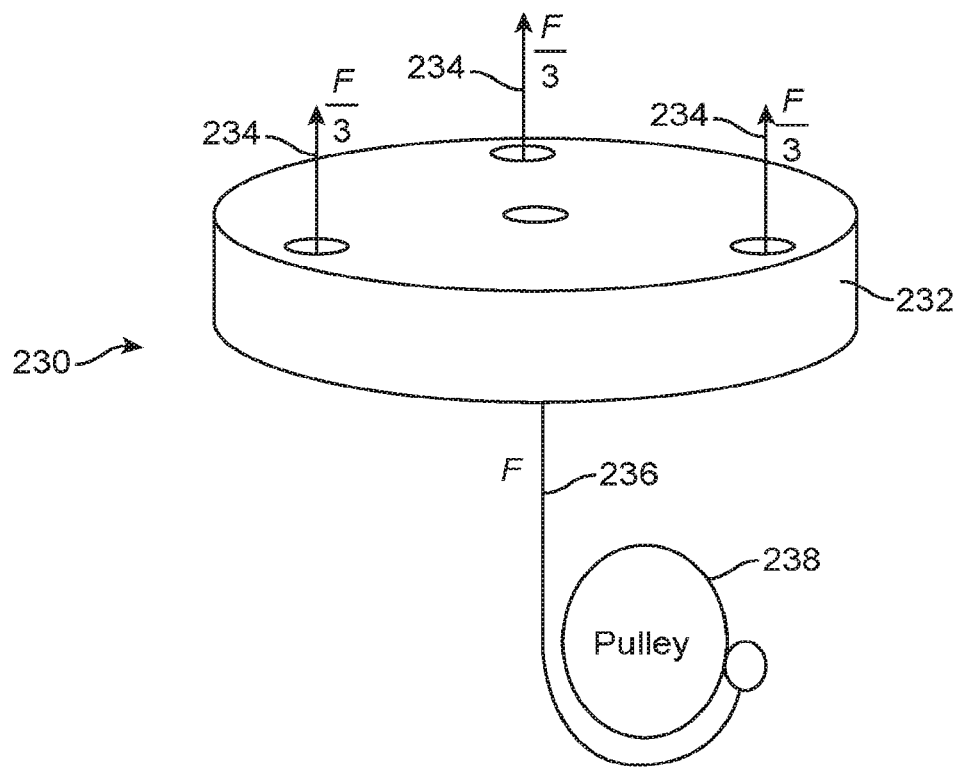
FIG. 21 is a perspective view of the disc-based load balancing mechanism of FIGS. 20A-20D, coupled with a pulley.

Referring to FIG. 21, the center of the disc 232 is attached to a pulley 238 in the splayer via a wire 236, for example. As tension increases with rotation of the pulley, the disc 232 may orient (e.g., tilt or pivot) as necessary, such that all three pullwires 234 have equal or intended tension. In embodiments where uniform tension in all three pullwires 234 is desired, it is achieved by putting equal spacing (i.e., 120 degrees) between each pullwire 234 and by placing each pullwire 234 an equal radial distance away from the center of the disc 232 (and an equal distance away from the location of the pulley attachment). Similar to the other load balancing designs described above, the load balancing mechanism 230 may also be used even if the pullwires 234 are not intended to be uniformly tensioned. In such embodiments, the desired relative load adjustment can be achieved by adjusting the spacing and/or radial location of the pullwires 234 such that the distance between them compensates for the load to be applied to them.

C. Gear Differential Embodiments

While the whiffletree mechanism just described may be used to distribute the pullwire load in a polyrail catheter design, it might not be ideal in all embodiments. In alternative embodiments, therefore, a rotational differential mechanism may be implemented on the pulley within the splayer of the catheter. A rotational differential mechanism may be preferred in some embodiments, because the pulley itself can be replaced by it. Additionally, the rotational differential mechanism can be scaled, such that it fits in the same area of the splayer as the pulley. Also, a differential can balance or distribute load over much greater changes in shaft deflection, as compared to a whiffletree.

Figure 22:
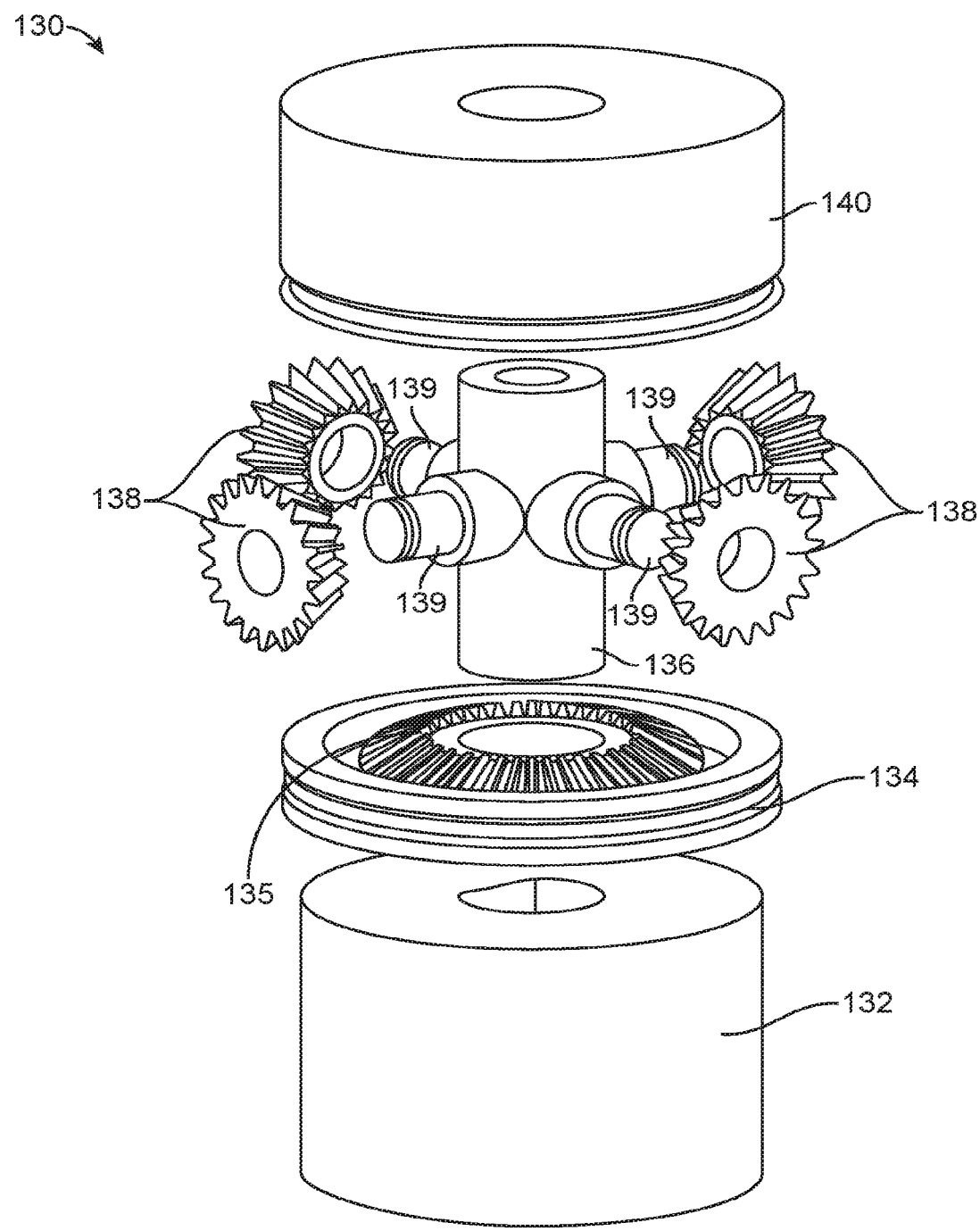
FIG. 22 is an exploded view of a two-way differential for balancing pullwire tension in a catheter, according to one embodiment.

FIG. 22 is an exploded, perspective view of one embodiment of a two-way differential mechanism 130. In this embodiment, the differential mechanism includes an input shaft 132, a stage one 134, a drive shaft 136, four pinions 138, four pinion axles 139 and a stage two 140. The input shaft 132 of the differential 130 is configured to engage with the output shaft of the robotic surgical system or sterile adaptor (not shown here). As the robot commands articulation, the output shaft of the robotic instrument driver rotates and directly results in rotation of the input shaft 132. The input shaft 132 is fixed to the drive shaft 136. Therefore, when articulation is commanded, the instrument driver rotates the output shaft, which directly results in rotation of the input shaft 132 and the drive shaft 136. In various embodiments, multiple pinions 138 are provided, which are free to rotate about their axes. In this embodiment, there are four pinions 138. Each pinion 138 is concentric with, and disposed on, a separate axle 139 extending perpendicularly from the drive shaft 136. Alternative embodiments may have as few as one pinion 138 or more than four pinions 138. In this embodiment, the drive shaft 136 and the axles 139 are all one piece, although in alternative embodiments, the axles 139 may be separate pieces attached to the drive shaft 136. Stage one 134 and stage two 140 are cylindrical components, free to rotate around drive shaft 136. Each stage 134, 140 has one pullwire fixed to it (not shown). The pullwires extend from the catheter. Each stage 134, 140 also includes a bevel gear 135, which is driven by the bevel on the pinions 138.

Figure 23B:
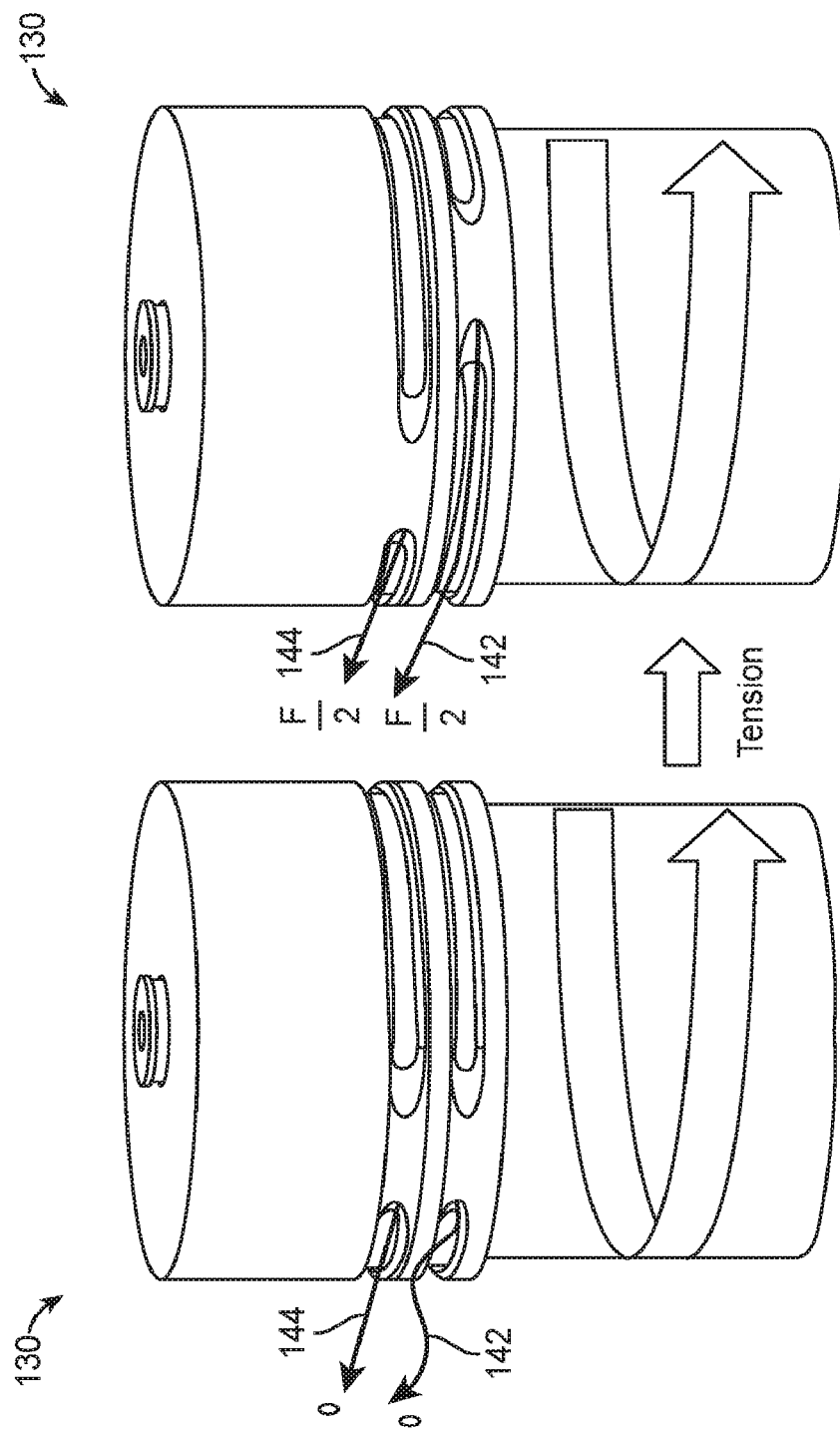
Figure 23C:
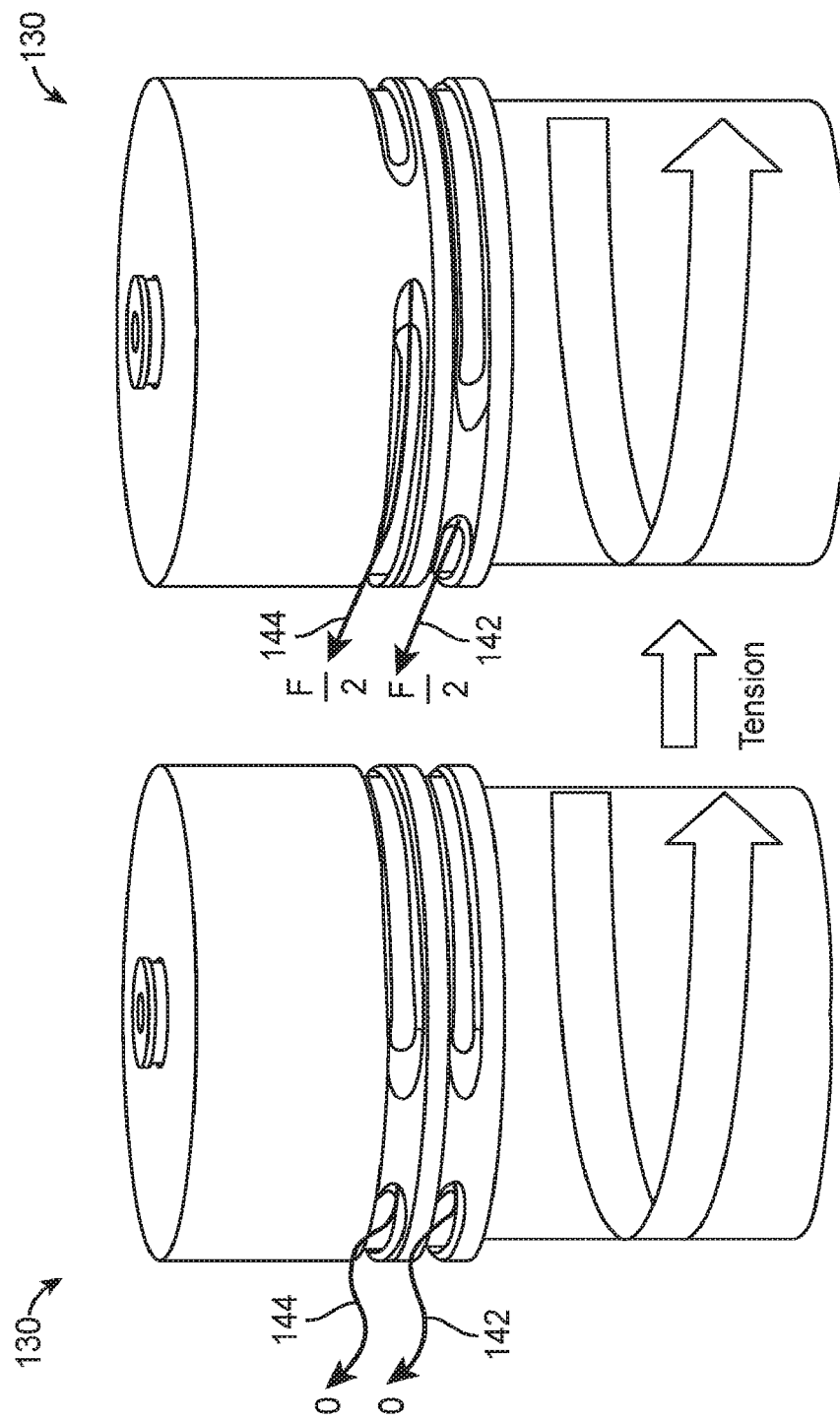

FIGS. 23A-23C illustrate how the differential 130 may operate to balance forces equally, independent of the path length of two pullwires 142, 144. A first pullwire 142 is attached to stage one 134, and a second pullwire 144 is attached to stage two 140. Each figure shows the differential 130 before (left hand side) and after (right hand side) tension is applied to the pullwires 142, 144 by the robotic instrument driver. On the left side of FIG. 23A, for example, both pullwires 142, 144 have equal slack. Therefore, as the drive shaft 136 is rotated, the pinions 138 do not rotate, and stage one 134 and stage two 140 rotate together until all the slack is taken up and tension is applied to the pullwires 142, 144

(left hand side of FIG. 23A). Then, as the drive shaft 136 continues to rotate and tension is applied, the force is split equally between the two pullwires 142, 144 (right hand side of FIG. 23A).

In FIG. 23B, the first pullwire 142, fixed to stage one 134, has more slack than the second pullwire 144, fixed to stage two 140. As the drive shaft 136 rotates, this time the pinions 138 rotate (as described in more detail below), which drives stage one 134 to rotate and take up the slack, while stage two 140 remains stationary. This ensures that the tension on the second pullwire 144, fixed to stage two 140, does not increase until the tension on the first pullwire 142, fixed to stage one 134, is equal to it. Then, when there is uniform tension on both pullwires 142, 144, the pinions 138 no longer rotate, and stage one 134 and stage two 140 rotate with the drive shaft 136.

FIG. 23C illustrates the opposite scenario of FIG. 23B. This time, there is more slack in the second pullwire 144 than in the first pullwire 142. In such a scenario, the pinions 138 drive stage two 140 to rotate and take up the slack while stage one 134 remains stationary until the tension in both pullwires 142, 144 is equal.

Figure 24A:
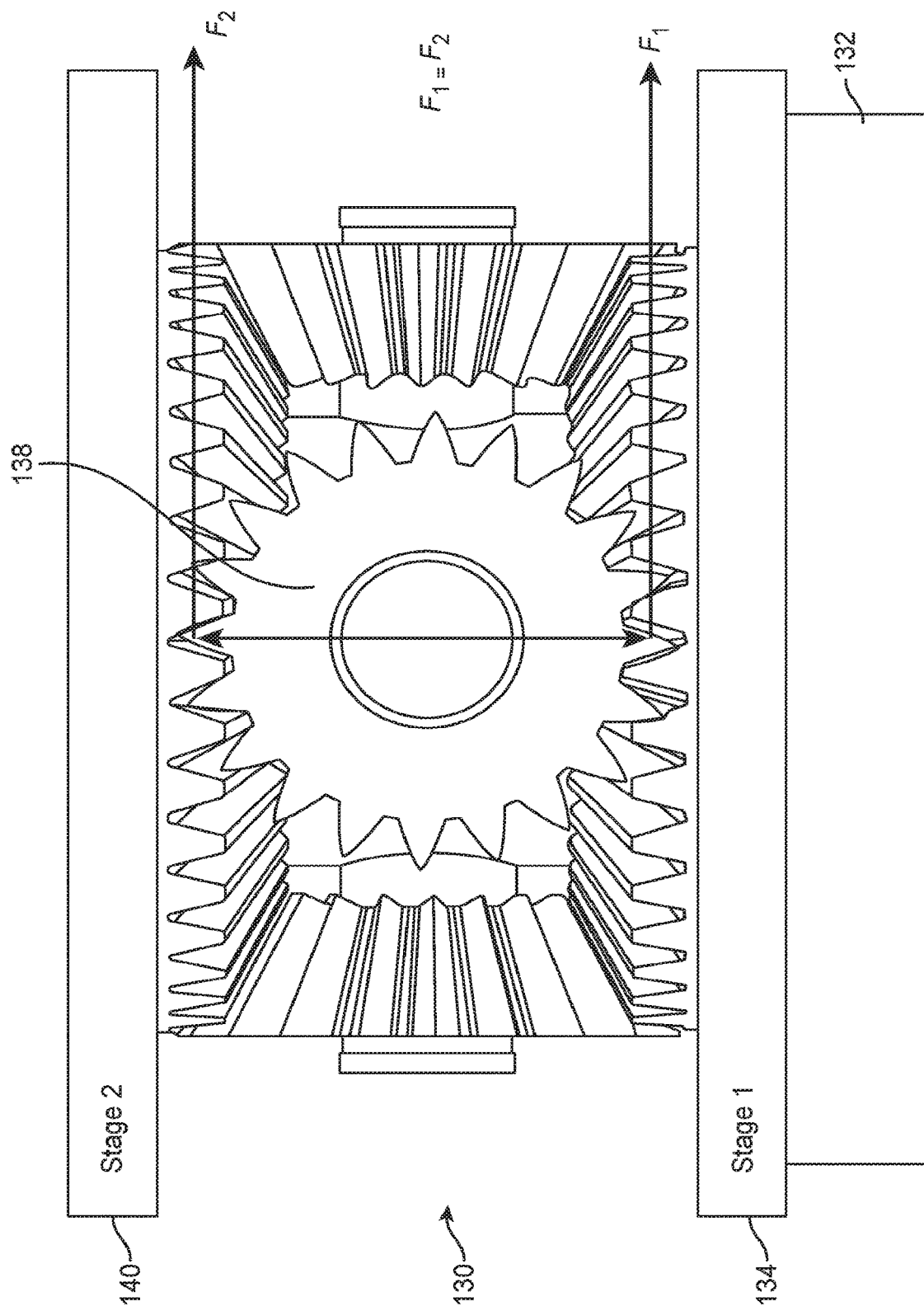
FIGS. 24A-24C are partial side views of the two-way differential of FIG. 17, illustrating three different tension balancing scenarios.

FIG. 24A shows a partial side view of the differential 130 in the same configuration as illustrated in FIG. 23A, when each of the pullwires 142, 144 has equal slack. When there is equal slack, F1 is equal to F2, and thus, the pull on the upper teeth of the pinion 138 to rotate in the counterclockwise direction is equal and opposite to the pull on the lower teeth of the pinion 138 to rotate in the clockwise direction. In such a scenario, each side of a pinion 138 applies equal force to stage one 134 and stage two 140, and the pinion 138 does not rotate about its axle. Each of the pinions 138 will rotate with the input shaft and driver shaft about the central axis of the differential 130.

Figure 24B:
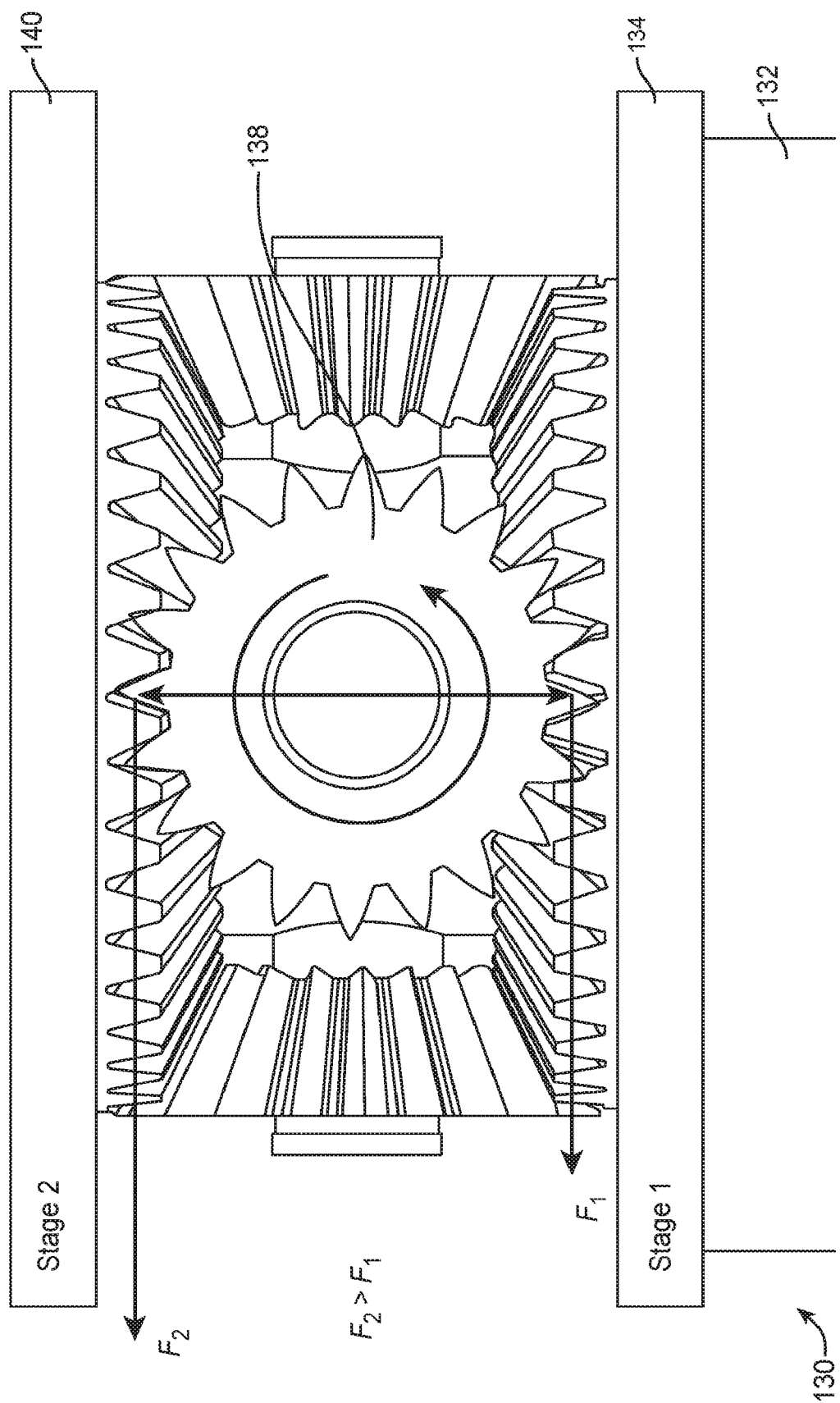
Figure 24C:
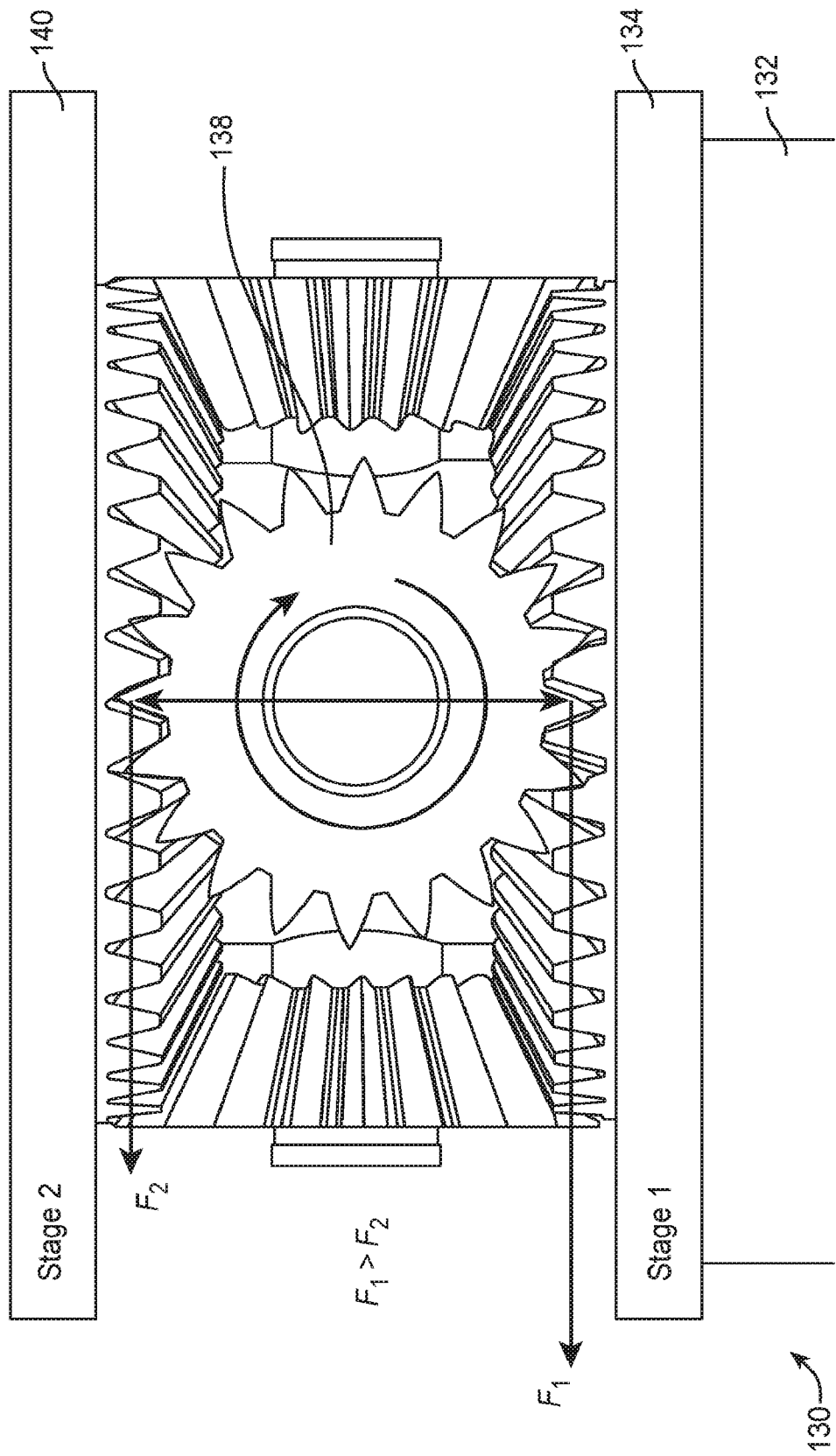

FIGS. 24B and 24C show partial side views of the differential 130 in the same configurations as depicted in FIGS. 23B and 23C, respectively. In FIG. 24B, F2 is greater than F1, due to slack on the first pullwire 142 attached to stage one 134. Therefore, the pinions 138 rotate in the counterclockwise direction, thereby taking up the slack. In FIG. 24C, F1 is greater than F2, due to slack on the second pullwire 144 attached to stage two 140. Therefore, the pinions 138 rotate in the clockwise direction to take up the slack. Pinions 138 generally rotate as required, to achieve uniform tension on both pullwires 142, 144.

The achievement of uniform tension on both pullwires assumes that each of the pullwires is attached to stage one 134 and stage two 140 at equal distances from the central axis. This general gear differential design may also be used in embodiments where it is desired to apply more force on one pullwire than the other. In such embodiments, the pullwire that requires higher loads should be placed at a proportionally smaller distance from the central axis than the pullwire requiring smaller loads.

Figure 26:
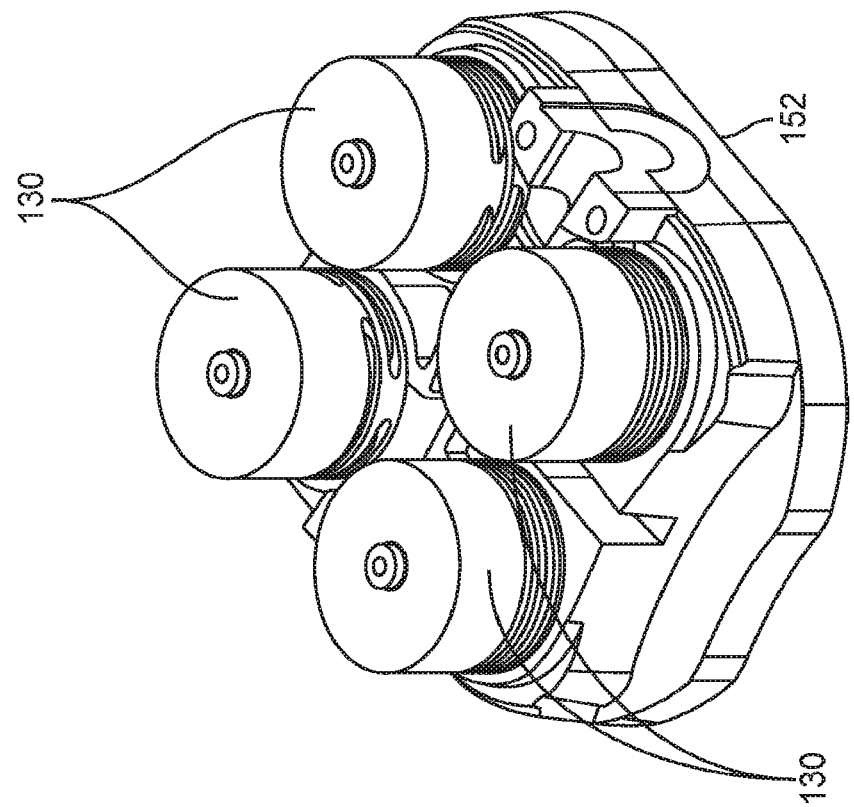
FIG. 26 is a perspective views of a splayer coupled with four two-way differentials, according to one embodiment.
Figure 25:
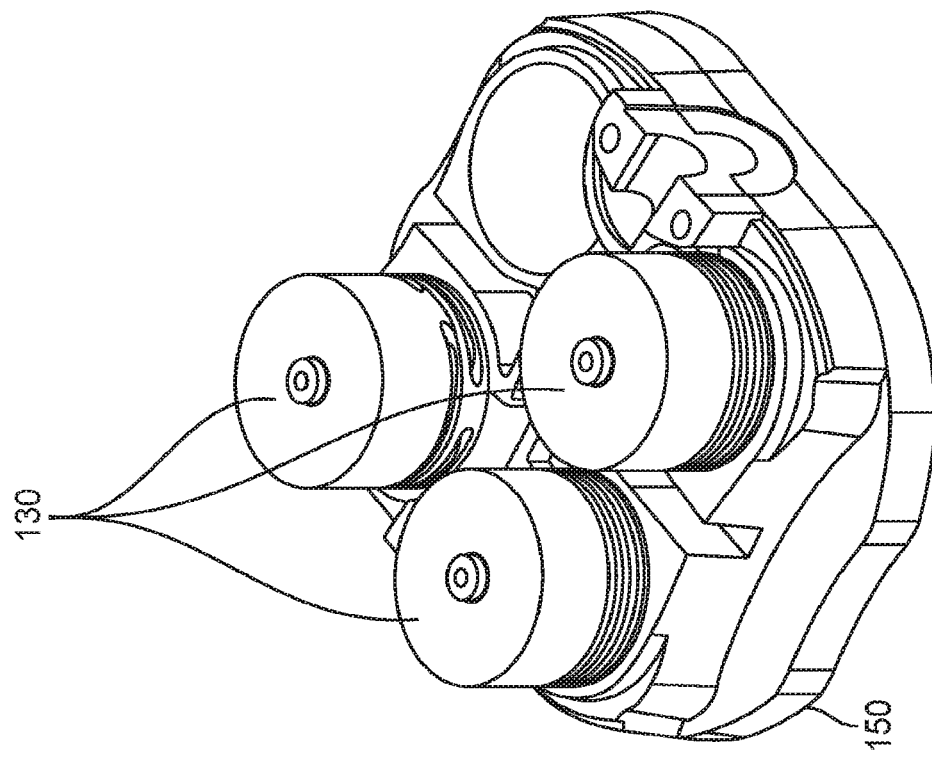
FIG. 25 is a perspective views of a splayer coupled with three two-way differentials, according to one embodiment.

FIGS. 25 and 26 illustrate two different embodiments of a splayer 150, 152 coupled with different numbers of differentials 130—splayer 150 coupled with three differentials 130 in FIG. 25, and splayer 152 coupled with four differentials 130 in FIG. 26. A splayer 150, 152 is often used to attach pullwires to pulleys, so that they can interface with an instrument driver. Such splayers are described, for example, in U.S. Pat. No. 8,052,636, which is fully incorporated herein by reference. Splayers 150, 152 are often described as interfaces between a robotic catheter and an instrument driver. Many instrument drivers in use today are designed to control four pulleys, and hence, four pullwires. The splayer 150 illustrated in FIG. 25 may allow six pullwires, and the splayer 152 illustrated in FIG. 26 may allow eight pullwires, to be attached to the splayer 150, 152 via three or four two-way differentials 130.

The differential 130 described above is designed to balance the forces between two pullwires and is thus used in 6-wire or 8-wire embodiments, for example. In catheter embodiments that include nine pullwires, forces must be distributed in groups of three wires, and thus a three-way differential is needed.

Figure 27A:
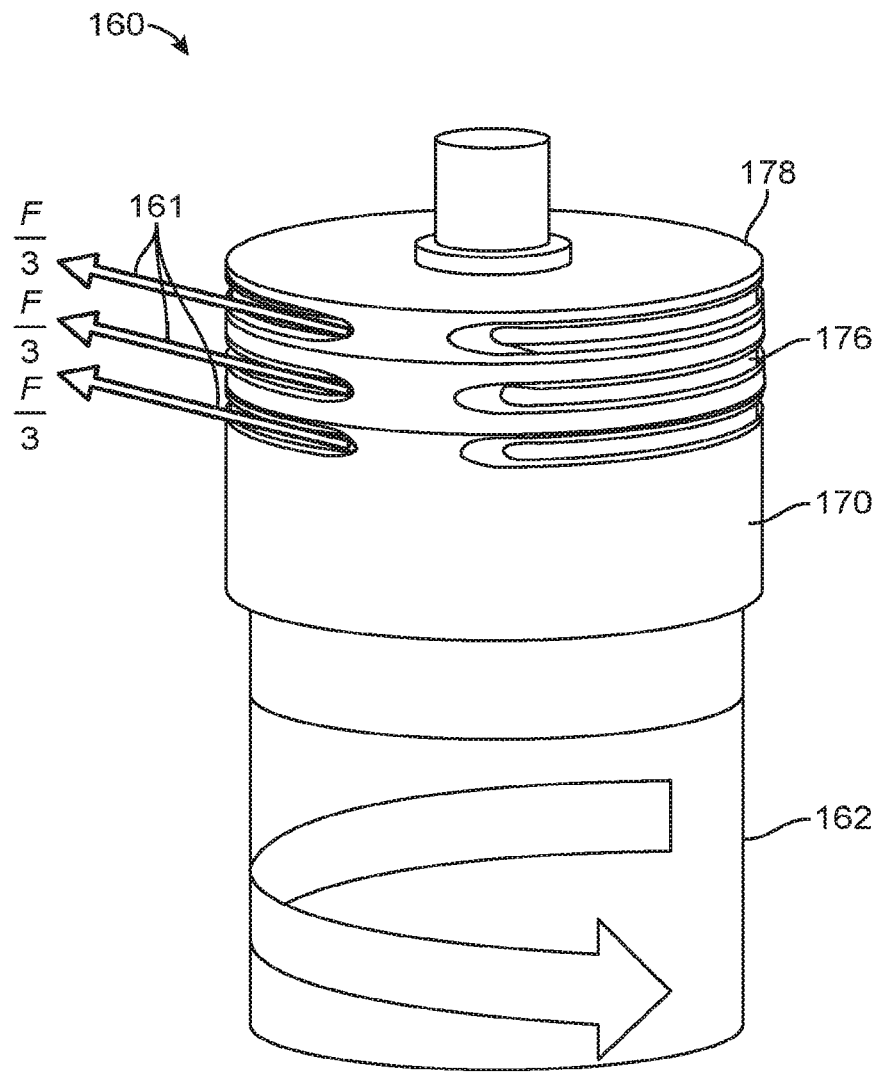
FIGS. 27A and 27B are perspective and side views, respectively, of a three-way differential for balancing tension in pullwires of a catheter, according to one embodiment.
Figure 27B:
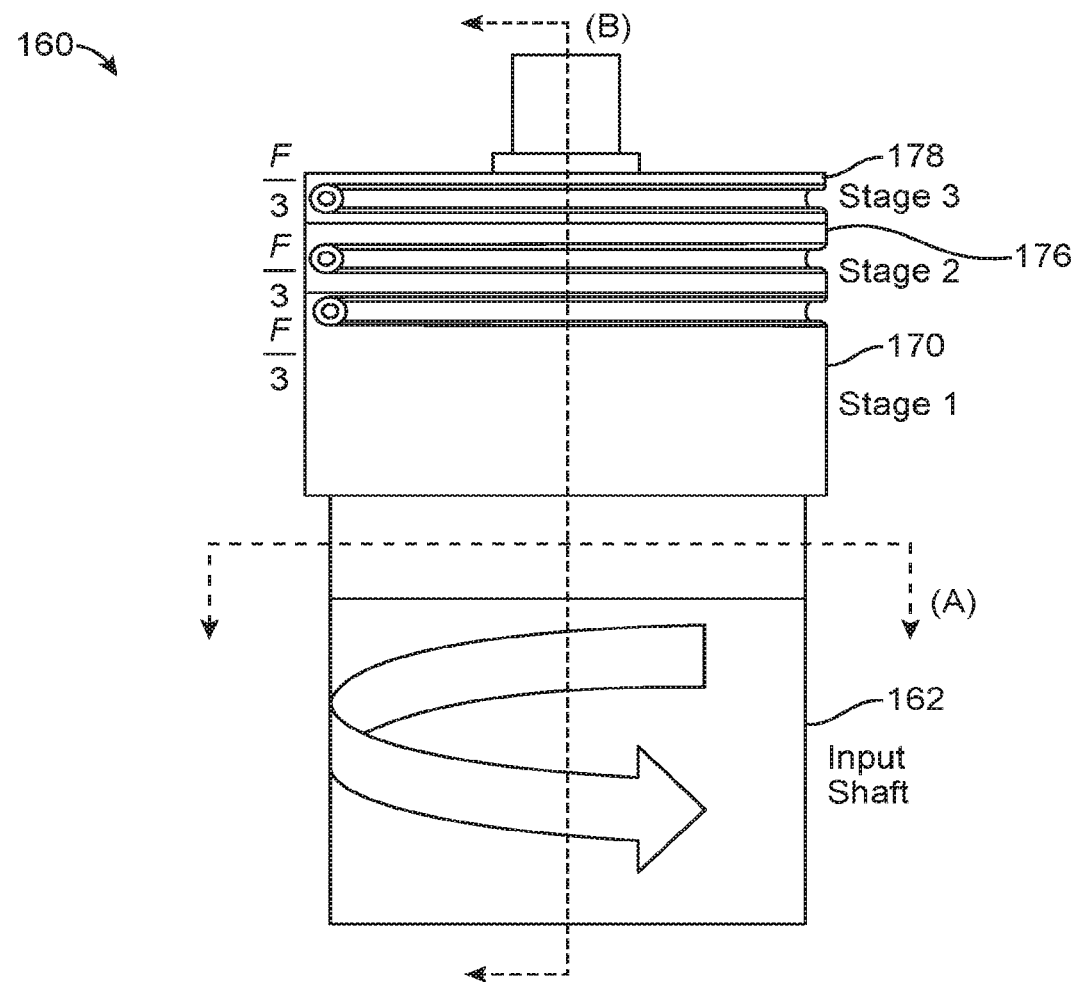
Figure 27C:
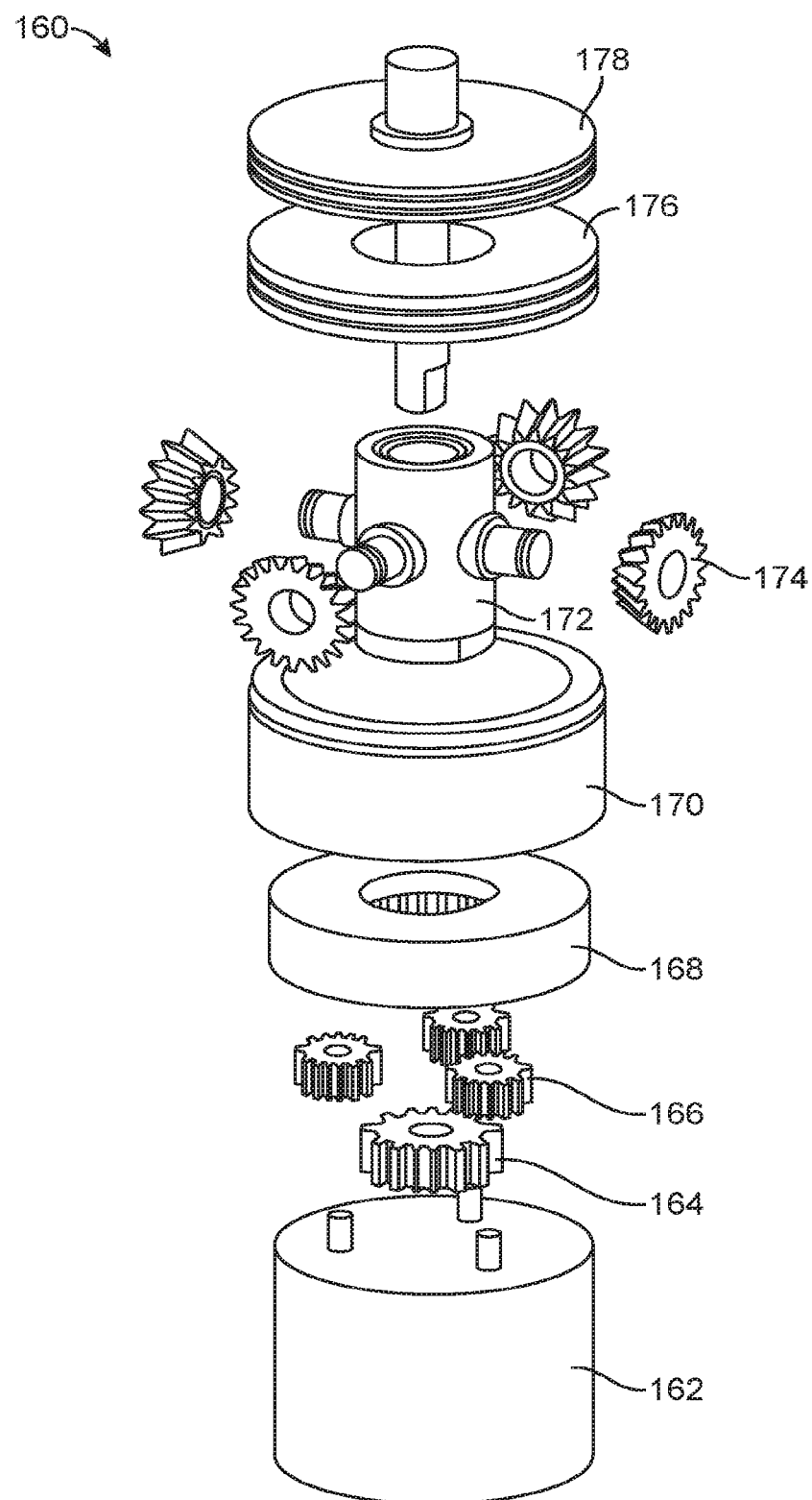
FIG. 27C is an exploded view of the three-way differential of FIGS. 27A and 27B.
Figure 27D:
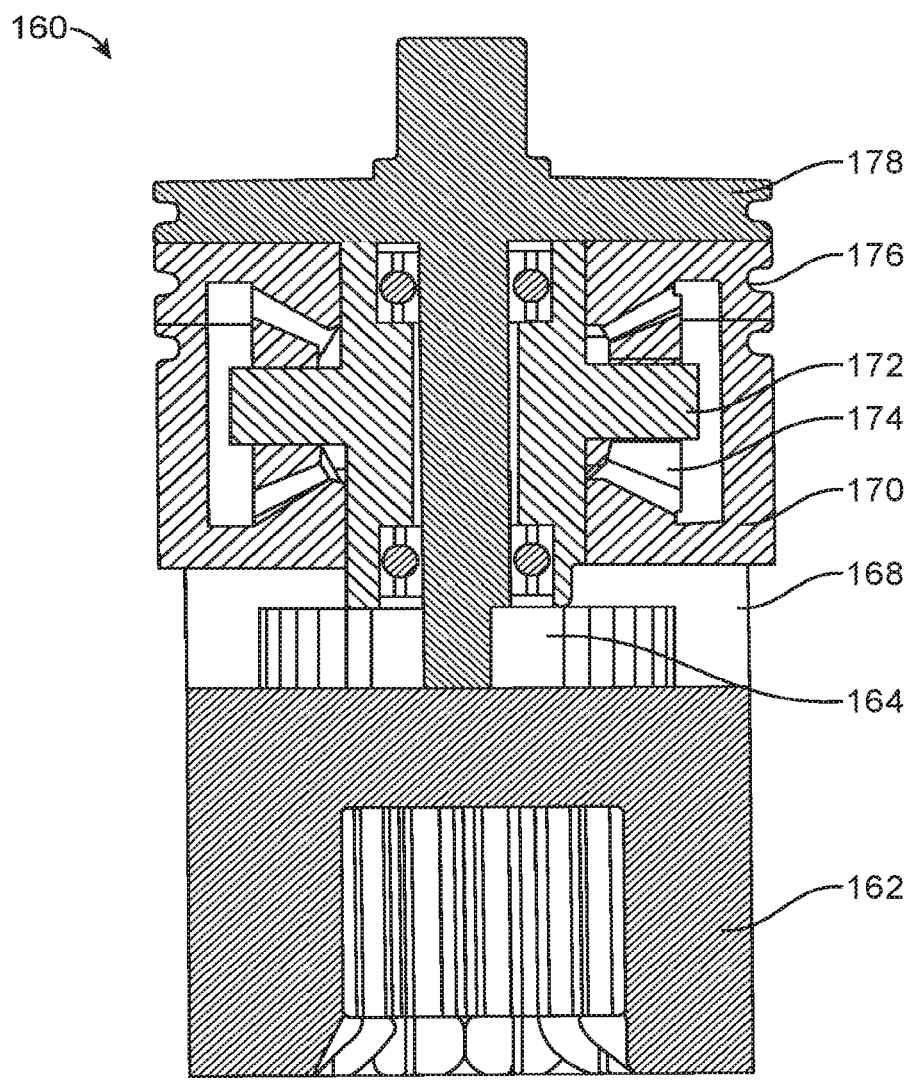
FIG. 27D is a side, cross-sectional view of the three-way differential of FIGS. 27A and 27B, from the perspective indicated by dotted line "B" in FIG. 27B.

Referring now to FIGS. 27A-27H, one embodiment of a three-way differential 160 is illustrated. As shown in the perspective view of FIG. 27A, the three-way differential 160 is configured to distribute the load applied between three pullwires 161 within a group. FIG. 27B is a side view of the three-way differential 160, showing locations of a first cross-sectional view (dotted line A, corresponding to FIGS. 27E and 27F) and a second cross-sectional view (dotted line B, corresponding to FIG. 27D). As shown in the exploded view of FIG. 27C and the side, cross-sectional view of FIG. 27D, the three-way differential 160 may include an input shaft 162 (with three pegs 163), a sun gear 164, three planet gears 166, a ring gear 168, a stage one 170, a drive shaft 172 (with four pinion axles 173 protruding from it), four bevel pinion gears 174, a stage two 176, a stage three 178, and a stage three shaft 179. The differential 160 may operate according to the same principle as the three-way whiffletree, except rotationally, where one pullwire per articulation direction is fixed to each of the three stages 170, 176, 178. The three-way differential 160 is split up into two, two-way differentials—one biased differential and one unbiased differential. The biased differential distributes the torque 2-to-1 between the unbiased differential and stage three 178, respectively. The unbiased differential then balances torque equally between stage one 170 and stage two 176. If tension on the three pullwires is not equal, then stages 170, 176, 178 will rotate relative to each other with the aid of the rotating pinions 174, until equal torque in each stage 170, 176, 178 is achieved. This results in a balanced equilibrium between the three pullwires, regardless of catheter curvature or manufacturing tolerances. An omnidirectional catheter will typically include three differentials 160 total, one for each articulation direction.

The stage three shaft 179 includes a keyed end, which passes through a bore in the drive shaft and mates with a central bore in the sun gear 164. Similarly, the drive shaft 172 has a keyed end, which passes through a bore in the stage one 170 and mates with a central bore in the ring gear. Thus, the stage three shaft 179 is driven by the sun gear 164, and the drive shaft 172 is driven by the ring gear 164. The pegs 163 of the input shaft 162 drive the planet gears 166, which are able to spin about their own axes and also about the central axis of the input shaft 162.

Figure 27E:
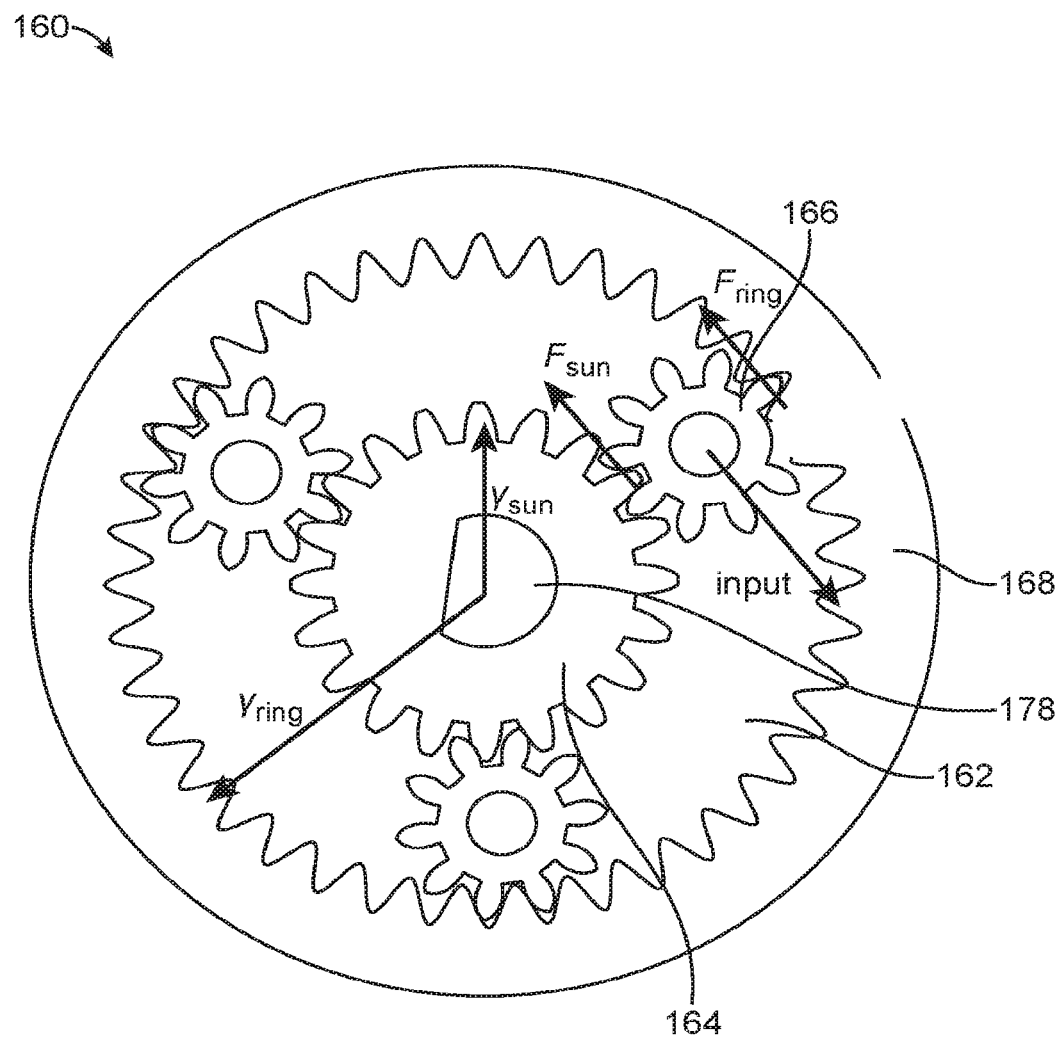
FIGS. 27E and 27F are top, cross-sectional views of the three-way differential of FIGS. 27A and 27B, from the perspective indicated by dotted line "A" in FIG. 27B.
Figure 27F:
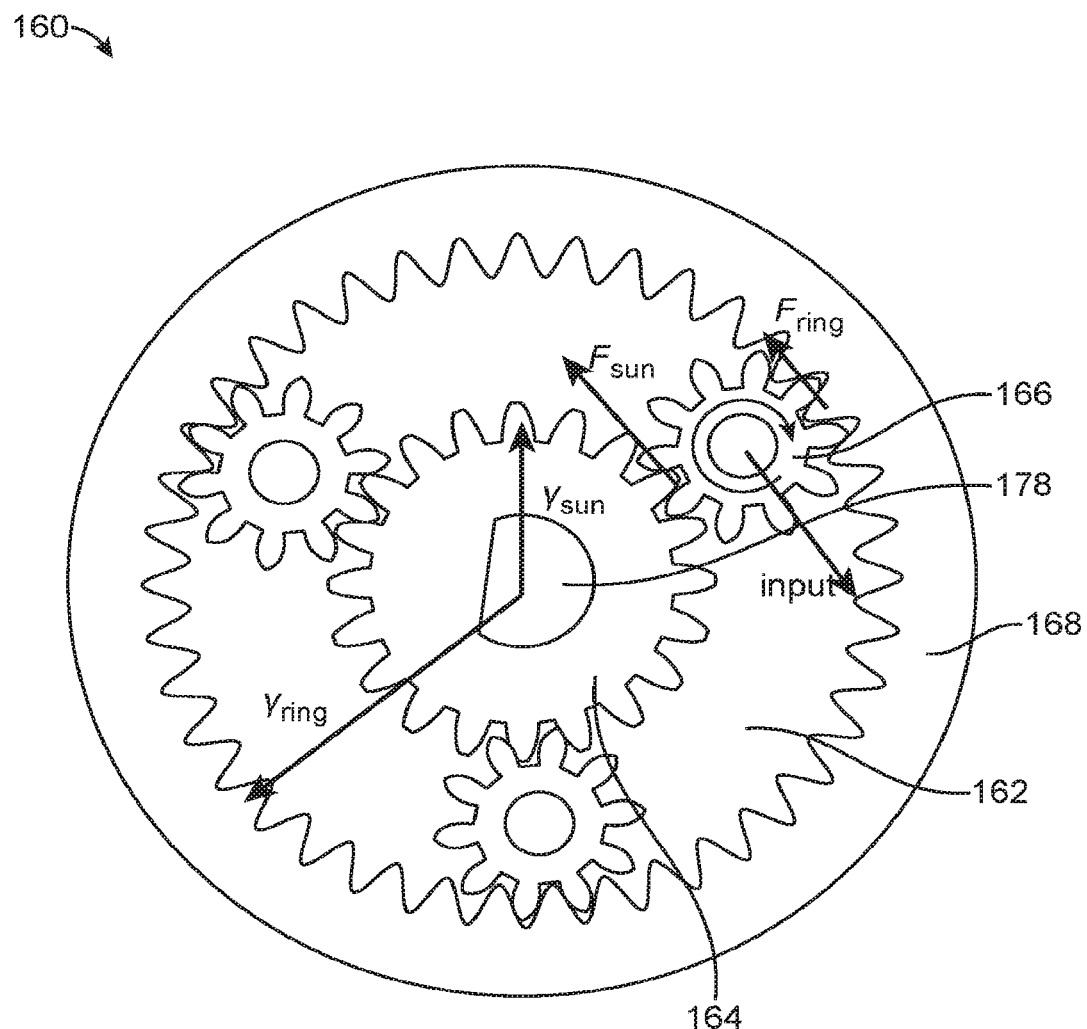

Referring to FIGS. 27E and 27F, the mechanism of the three-way differential will be described. Torque from the input shaft 162 applies a radial force to the inside of planet gears 166. The planet gears 166 mesh with the sun gear 164 and the ring gear 168 and are free to rotate about their own axes. In some embodiments, the radius of the sun gear 164 is half the radius of the ring gear 168. Thus, if the torque of the sun gear 164 is half the torque of the ring gear 168, the resultant tangential force on each side of the planet gear 166 will be equal, as shown in FIG. 27E. Because the tangential forces on the planet gear 166 are equal and opposite, the planet gear 166 does not rotate about its own axis, but rather the axis of the differential 160. The reduction is biased, such that the ring gear 168 has twice the mechanical advantage as the sun gear 164. Therefore, two pullwires driven by the ring gear 168 have equal tension to the one pullwire driven by the sun gear 164. If the torques of the ring gear 168 and the sun gear 164 are not distributed 2-to-1 respectively (in other words, if the two pullwires driven by the ring gear 168 are not applying two times the tension as the pullwire driven by the sun gear 164 because of shaft curvature), the planet gears 166 will rotate until equilibrium is achieved.

FIG. 27F shows the planetary gear system in an unbalanced state. Once the torque between the sun gear 164 and the ring gear 168 is distributed 2-to-1 respectively, torque is applied to the sun gear 164, which is fixed to stage three 178, and the ring gear 168, which will balance stage one 168 and stage two 176 through an unbiased differential.

$$T_{sun} = r_{sun} * F$$

$$T_{ring} = r_{ring} * F$$

$$F_{sun} = F_{ring} = \frac{T_{sun}}{r_{sun}} = \frac{T_{ring}}{r_{ring}}$$

$$\frac{T_{sun}}{1} = \frac{T_{ring}}{2}$$

$$T_{ring} = 2 * T_{sun}$$

Referring again to FIGS. 27C and 27D, the ring gear 168 is fixed to the drive shaft 172, which applies a radial force to the bevel pinion gears 174 in the unbiased differential. The unbiased differential is essentially the two-way differential shown in FIG. 22, except the torque is applied from the ring gear 168, rather than the input shaft 162. The unbiased differential drives two of the three pullwires of an articulation axis and balances the torques equally between stage one 170 and stage two 176.

Figure 27G:
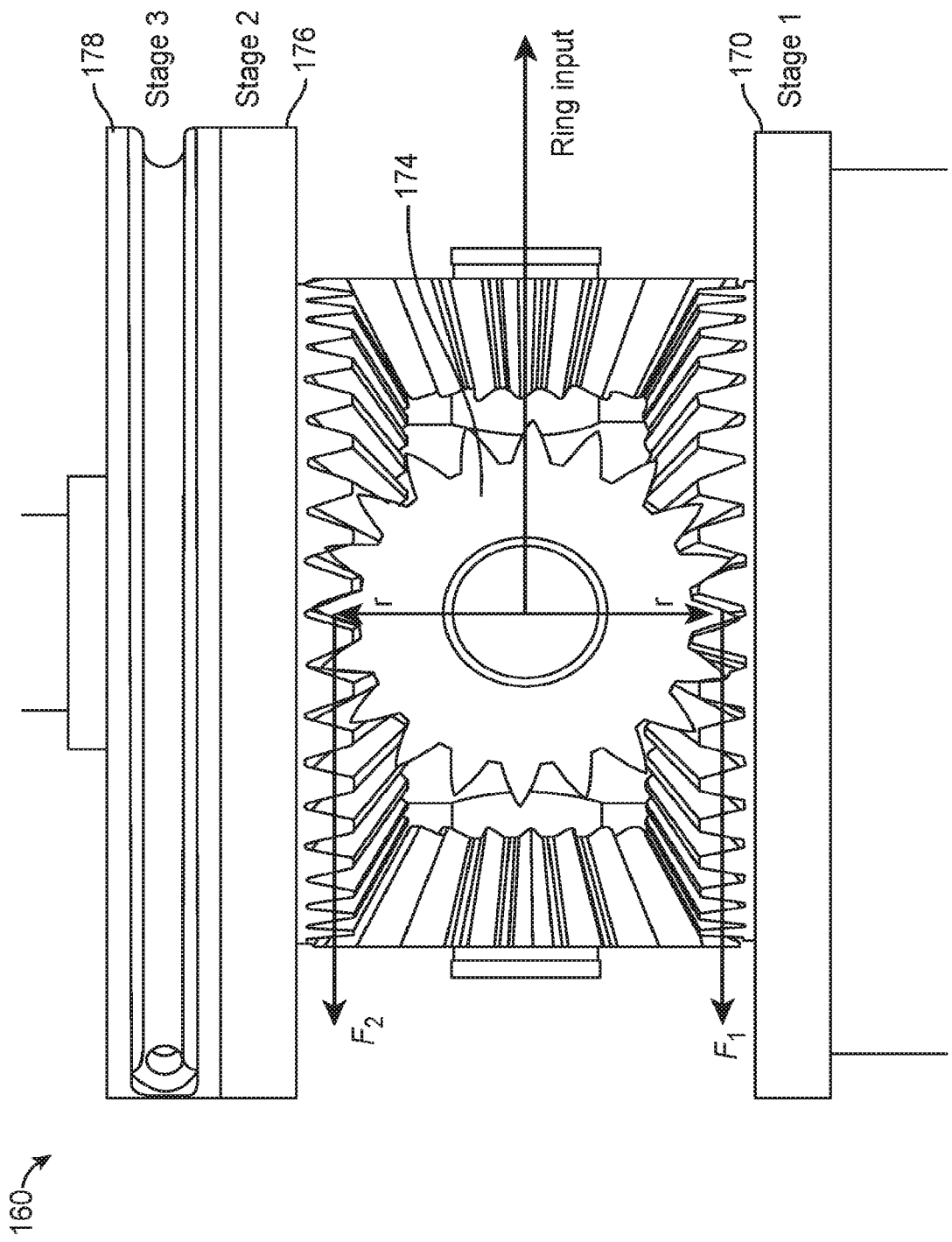
FIGS. 27G and 27H are partial side views of the three-way differential of FIGS. 27A and 27B.
Figure 27H:
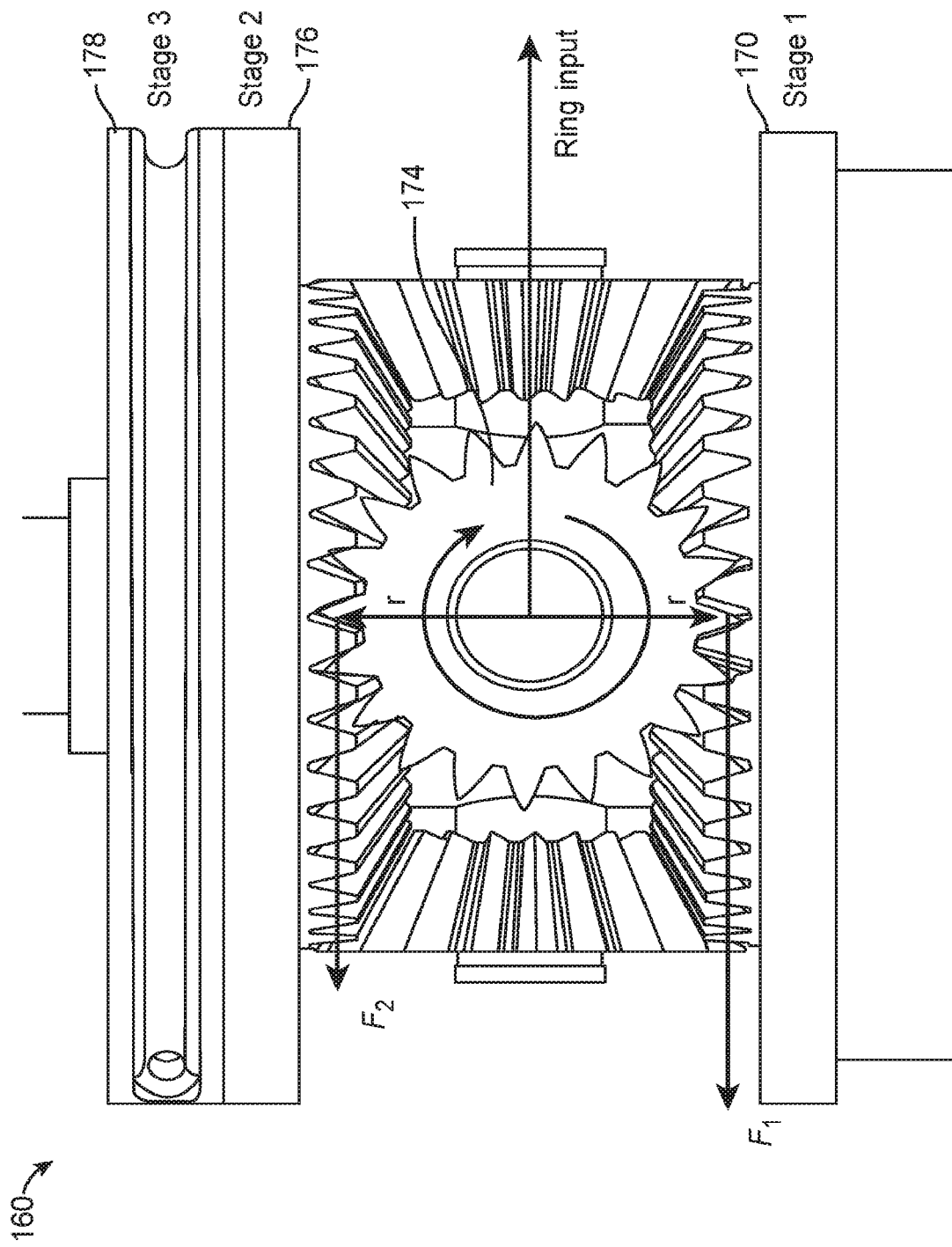

FIG. 27G shows the unbiased differential balancing forces on stage one 170 and stage two 176 equally. Torque from the ring gear 168 applies a force on the pinion bevel gear 174 until stage one 170 and stage two 176 are applying equal force. FIG. 27H is an example of the unbiased differential in an unbalanced state, where the torque of stage two 176 is less than the torque of stage one 170. In this case, stage two 176 would rotate, while stage one 170 would be kept stationary, until the torques were balanced.

As described above, in other embodiments, the loads to the two pullwires are intentionally distributed unequally. In such embodiments, the pullwires are not uniformly positioned within the catheter shaft. In such embodiments, a biased differential may be provided by attaching each of the pullwires at a different radius from the center axis, such that the loads are still distributed throughout the shaft and there is no net bending moment.

III. Multi-Bending Catheter Design

In some embodiments, the load distribution mechanisms described above may be used in a double-bending catheter or multi-bending catheter. A multi-bending catheter includes a catheter body having a proximal non-articulating shaft section and two or more distal articulation sections. The articulation sections are aligned along the catheter body with one or more articulation sections being more distally located relative to one or more other articulation sections. Accordingly, "distal articulation sections" and "proximal articulation sections" are referred to herein; however, in general, each of these articulation sections is distal to the proximal non-articulating shaft section. The articulation sections each include one or more pullwires attached thereto, such that each articulation section is configured to independently articulate in one or more directions with the actuation of corresponding pullwire(s). In some embodiments, the articulation sections are in direct contact with each other; in other embodiments, the articulation sections are spaced apart, with additional non-articulating sections positioned between them.

One of the challenges with multiple bending catheters is how to anchor the pullwires of a proximal section while allowing adequate space for the pullwires of the distal section to extend past this anchor point. A typical catheter 180 is illustrated in FIG. 28, including a catheter tip 182, a distal anchor ring 184, a distal articulation section 186, a pullwire 188, a proximal articulation section 181, a proximal anchor ring 185, and a bump 183 in the outer diameter (OD) of the catheter shaft at the location of the proximal anchor ring 185. Typically, pullwires 188 are anchored to a fixed location on the catheter tip 182. The pullwires 188 are often soldered or welded to a control ring or anchor ring 184, 185, which is embedded into the wall of the catheter 180. There will often be a bump 183 or increase in the OD of the catheter 180 at the proximal anchor ring 185, where the pullwires 188 going to the distal ring 184 need to pass over, under, or through the proximal ring 185.

Figure 29C:
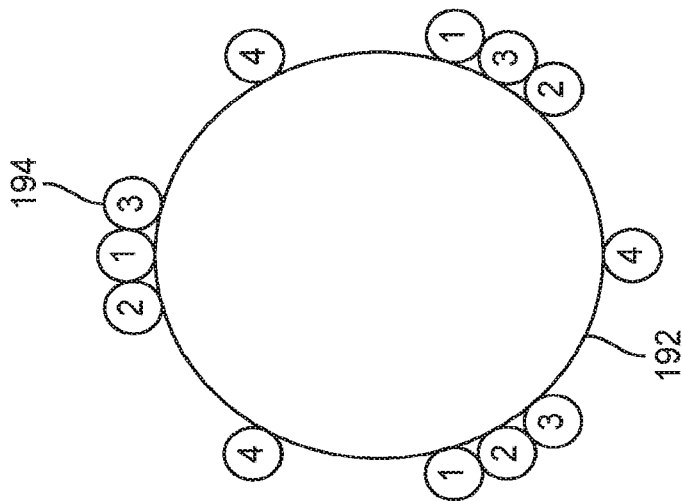
FIGS. 29A-29C are diagrammatic cross-sectional views of a multi-bend, twelve-pullwire catheter, illustrating one possible configuration for pullwires along a distal articulation section (FIG. 29A), a proximal articulation section (FIG. 29B), and a proximal shaft section (FIG. 29C) of the catheter, according to one embodiment.
Figure 29B:
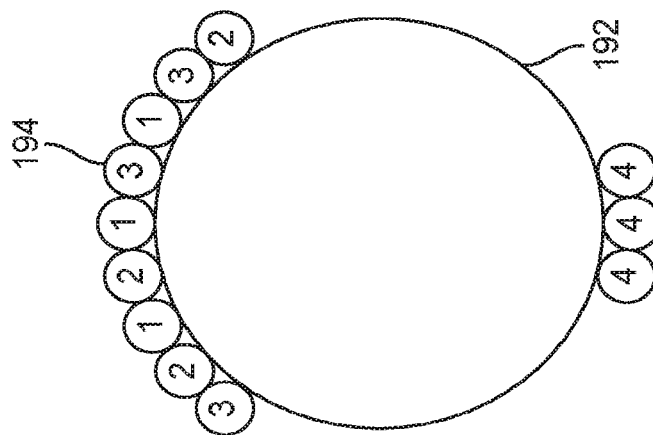
Figure 29A:
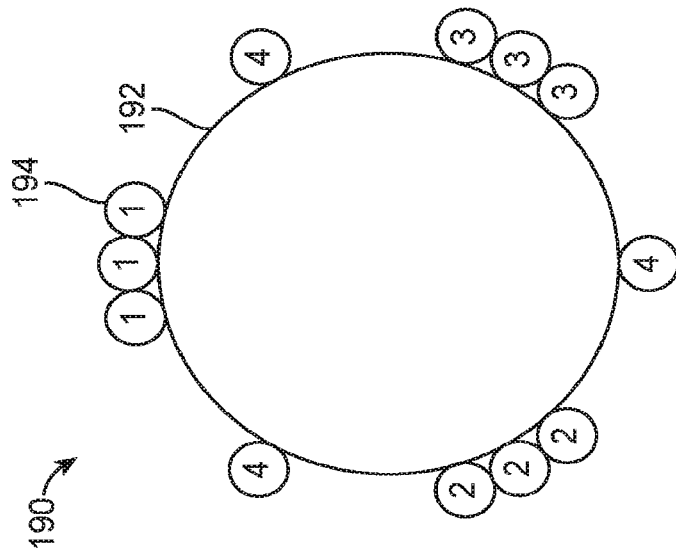

In one embodiment of the present disclosure, the load distribution mechanisms described above are used in a double-bending catheter having an omnidirectional distal section and a single-plane proximal articulation section without a proximal solder. FIGS. 29A-29C illustrate one embodiment of a catheter 190 with a shaft 192 (or "sidewall") and multiple pullwires 194, configured to be a double bending catheter having load distribution. All four groups of pullwires 194 are made up of three individual wires 194. The fourth wires are placed centrally between the first three wires in the distal articulation section, as shown in FIG. 29A. When distal articulation is required toward the 12 o'clock position, all three group 1 wires are pulled uniformly. When articulation towards 4 o'clock is required, all three group 3 wires are pulled uniformly. When articulation towards 6 o'clock is required, all three group 3 wires and all three group 2 wires are pulled uniformly. The group 4 wires are not used to actuate the distal bend.

In the proximal articulation section of the catheter 190, shown in FIG. 29B, wire groups 1, 2, and 3 all merge together at one side of the catheter shaft 192, and wire group 4 merges together directly opposite. This transition of the articulation wires 194 from being uniformly positioned in the articulation section to being closely positioned where articulation is not intended or being closely positioned to control a degree of freedom of another bend is described in U.S. Pat. No. 8,894,610, which is fully incorporated by reference. To achieve controlled proximal articulation, wire tension may be applied to wire group 4, or wire tension may be applied to wire groups 1, 2, and 3 simultaneously. If distal articulation is desired, wire tension can be applied to wire groups 1, 2, or 3 but must be counterbalanced with wire tension on wire group 4 to prevent unwanted proximal articulation.

The designs presented in U.S. Pat. No. 8,894,610 rely on all wires converging at one side of the shaft to minimize shaft deflection. In contrast, the embodiment of the multi-bend catheter 190 presented here redirects the pullwires 194 in the proximal non-articulating shaft 192, as shown in FIG. 29C. Therefore, wire groups 1, 2, 3, and 4 are all equally distributed in the proximal shaft 192, resulting in no bending moment in the shaft 192 when any of the 4 groups are tensioned.

Figures 30A, 30B:
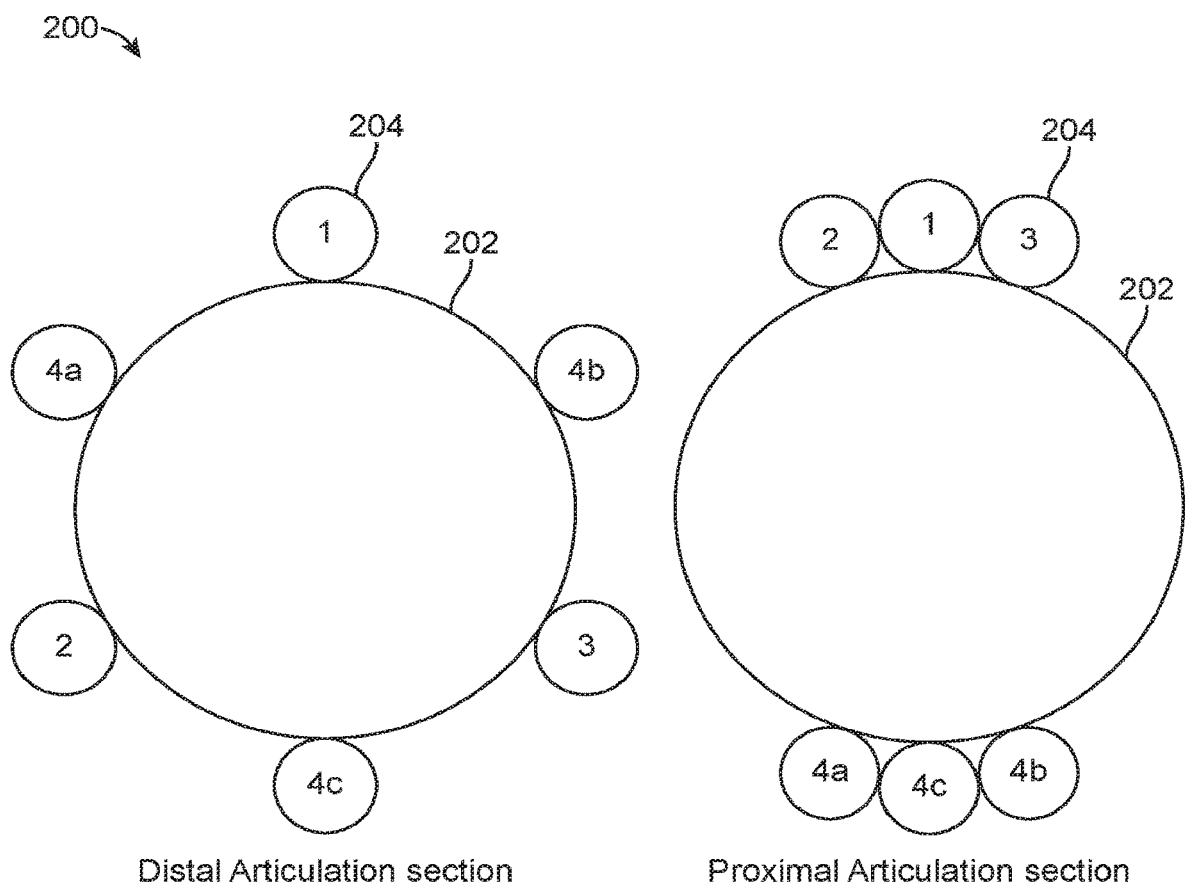
FIGS. 30A and 30B are diagrammatic cross-sectional views of a multi-bend, six-pullwire catheter, illustrating one possible configuration for pullwires along a distal articulation section (FIG. 30A) and a proximal articulation section (FIG. 30B), according to one embodiment.

Referring now to FIGS. 30A and 30B, an alternative embodiment of a multi-bend catheter 200 may include a catheter shaft 202 and multiple pullwires 204. In this embodiment, the catheter 200 may include only one pullwire 204 (instead of the three wires) in each of the pullwire groups 1, 2, and 3. Pullwire group 4 still includes three pullwires 204. Therefore, this alternative embodiment includes a total of six wires. Wires 1, 2, and 3 are equally positioned in the distal bend (FIG. 30A) and are co-located in the proximal bend (FIG. 30B). The three pullwires 204 of group 4 are spread uniformly between the three distal pullwires 204 in the distal section (FIG. 30A) and combined on the opposite side of the distal wires 204 in the proximal bend (FIG. 30B). This design has the same bending capability as the design presented in FIGS. 29A-29C, except that this design cannot isolate the proximal portion of the shaft 202. The proximal shaft 202 may thus be made of stiffer material or may employ the unirail design to minimize unwanted deflection.

In the multi-bend catheter embodiments described immediately above, the proximal articulation section is unidirectional. That is, it can only bend in one plane. In some alternative embodiments, it may be advantageous to have a catheter with omnidirectional distal and proximal articulation capabilities.

Figure 31A:
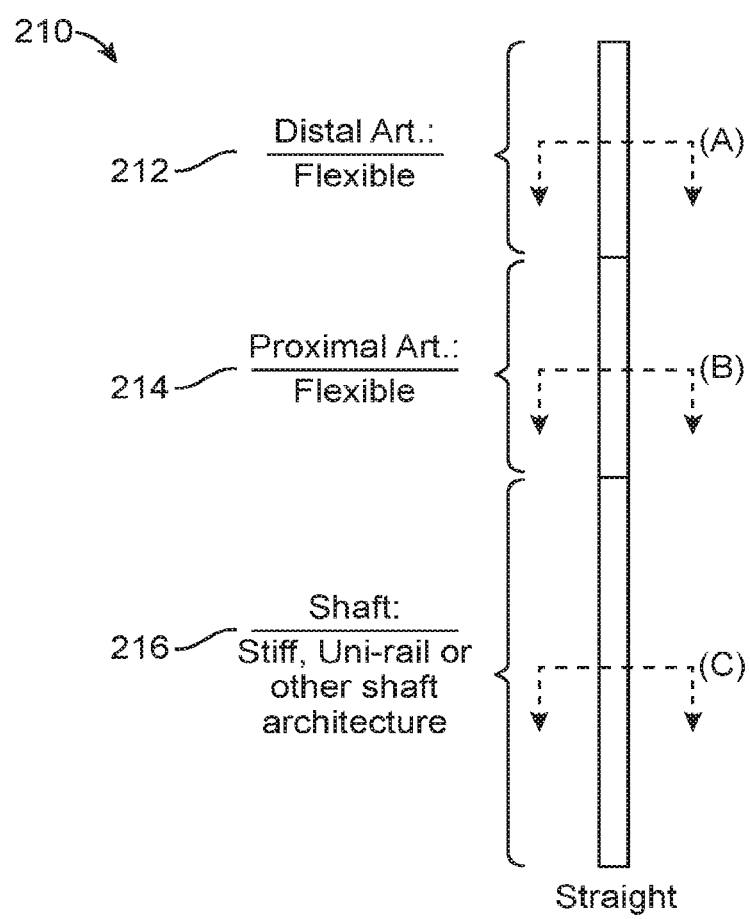
FIGS. 31A and 31B are diagrammatic side views of a multi-bend catheter in a straight configuration (FIG. 31A) and a double-bend configuration (FIG. 31B), according to one embodiment.
Figure 31B:
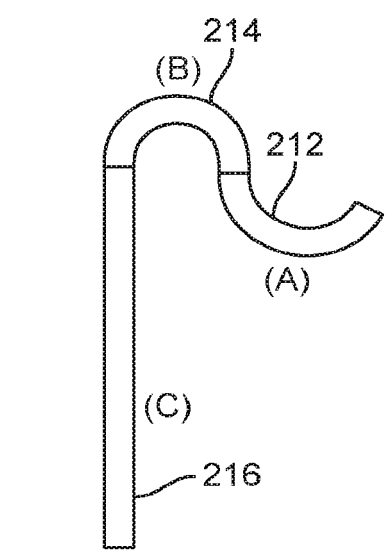

Referring now to FIGS. 31A and 31B, one embodiment of an omni-directional, multi-bend catheter 210 is illustrated in simplified form. FIG. 31A shows the catheter 210 in a straight configuration, and FIG. 31B shows the catheter 210 in a double-bend configuration. As illustrated in both figures, the catheter 210 may include a distal articulation section 212, a proximal articulation section 214 and a shaft section 216. The dotted lines labeled "A," "B," and "C" illustrate sections through the catheter 210, which are illustrated in different embodiments in FIGS. 32A-32C and 33A-33C. The shaft section 216 is a proximal portion of the catheter 210 and may also be referred to herein as a "proximal shaft section" or "proximal shaft portion."

Referring now to FIGS. 32A-32C, one embodiment of the multi-bend catheter 210 is illustrated, with six pullwires 218 organized in three groups of two. In the distal articulation section 212 (FIG. 32A), pullwires 218 paired together do not need to be touching but are positioned adjacent to each other. The pullwires 218 are then spread out equally about the shaft in the proximal articulation section 214 (FIG. 32B), to distribute tension. Finally, all the pullwires 218 are grouped together on one side of the catheter along the shaft section 216 (FIG. 32C)—in other words, the shaft section 216 has a unirail configuration.

Pulling on wires 1a and 1b will articulate the distal articulation section 212, while not affecting the proximal articulation section 214 or the shaft section 216. However, if bending of the proximal articulation section 214 is desired, pullwires 3b and 2a may be tensioned, and it would not affect the bend in the distal articulation section 212, because in that section, pullwires 3b and 2a are positioned 180° opposite each other. In this way, the same pullwires may extend through, and couple to, each articulation section while being arranged such that independent articulation of each articulation section can be achieved with selective tensioning of the various pullwires.

The articulation capability of the catheter 210 in FIGS. 32A-32C includes the following articulations. For distal articulation toward 12 o'clock, pull 1a and 1b. For distal articulation toward 4 o'clock, pull 2a and 2b. For distal articulation toward 8 o'clock, pull 3a and 3b. For distal articulation toward 6 o'clock, pull 2a, 2b, 3a, and 3b. For distal articulation toward 10 o'clock, pull 1a, 1b, 3a and 3b. For distal articulation toward 2 o'clock, pull 2a, 2b, 1a, and 1b. In all these articulations of the distal articulation section 212, the proximal articulation section 214 will not bend, because the pullwires 218 being pulled are located 180° opposite to one another in the proximal articulation section 214.

For proximal articulation toward 12 o'clock, pull 2a and 3b. For proximal articulation toward 4 o'clock, pull 3a and 1b. For proximal articulation toward 8 o'clock, pull 2b and 1a. For proximal articulation toward 6 o'clock, pull 1a, 2b, 3a, and 1b. For proximal articulation toward 10 o'clock, pull 2a, 2b, 1a, and 3b. For proximal articulation toward 2 o'clock, pull 3a, 3b, 2a, and 1b. In all of these articulations of the proximal articulation section 214, the distal articulation section 212 will not bend, because the pullwires 218 being tensioned are 180° opposite one another in the distal articulation section 212.

FIGS. 33A-33C illustrate an alternative embodiment of a multi-bend catheter 220, with a distal articulation section 222 (FIG. 33A), a proximal articulation section 224 (FIG. 33B), and a shaft section 226 (FIG. 33C). In this embodiment, rather than using the unirail configuration in the shaft section 226, the shaft section 226 instead is made stiffer, to resist deflection. This stiffer shaft may be accomplished by using a higher durometer material and/or a different catheter shaft braid architecture. With this stiffer architecture, the pullwires 228 may continue through the shaft section 226 in the same configuration as in the proximal articulation section 224.

In another alternative embodiment (not shown), a multi-bending catheter may include nine pullwires, where each pullwire is attached to individual motors.

Although the above description is believed to be a complete and accurate description of a number of embodiments of articulating steerable catheter for use in medical or surgical procedures, any suitable variations on the embodiments described above may be made, without departing from the scope of the invention. For example, features of one of the described embodiments may be applied to other embodiments, features may be added to or omitted from a given embodiment, or the like. Thus, the above description is meant to provide details of various embodiments only, and it should not be interpreted as limiting the scope of the invention as it is defined by the claims.

The invention claimed is:

1. An apparatus comprising:
   (a) an elongate member comprising:
      (i) a first longitudinal portion,
      (ii) a second longitudinal portion proximal to the first longitudinal portion, and
      (iii) a third longitudinal portion proximal to the second longitudinal portion; and
   (b) an articulation assembly operable to drive articulation of the first longitudinal portion via a first set of pullwires without simultaneously driving articulation of the second longitudinal portion, the first set of pullwires having a non-equal angular distribution in the first longitudinal portion and an equal angular distribution in the second longitudinal portion, the articulation assembly being further operable to drive articulation of the second longitudinal portion via a second set of pullwires without simultaneously driving articulation of the first longitudinal portion, the second set of pullwires having an equal angular distribution in the first longitudinal portion and a non-equal angular distribution in the second longitudinal portion, such that the first longitudinal portion and the second longitudinal portion are operable to articulate independently relative to each other.

2. The apparatus of claim 1, the elongate member comprising a catheter.

3. The apparatus of claim 1, the third longitudinal portion being configured to remain straight as the first longitudinal portion and the second longitudinal portion are in respective articulated states.

4. The apparatus of claim 3, the third longitudinal portion being configured to form a stiff rail.

5. The apparatus of claim 4, the third longitudinal portion having sufficient stiffness to resist deflection while the articulation assembly drives articulation of one or both of the first longitudinal portion or the second longitudinal portion.

6. The apparatus of claim 1, the first set of pullwires comprising a first pair of pullwires, the pullwires of the first pair being angularly spaced apart from each other by approximately 180 degrees along the second longitudinal portion, the pullwires of the first pair being angularly spaced apart by less than 180 degrees along the first longitudinal portion.

7. The apparatus of claim 6, the pullwires of the first pair being angularly spaced apart by less than 180 degrees along the third longitudinal portion.

8. The apparatus of claim 6, the pullwires of the first pair being angularly spaced apart by approximately 180 degrees along the third longitudinal portion.

9. The apparatus of claim 6, the second set of pullwires comprising a second pair of pullwires, the pullwires of the second pair being angularly spaced apart from each other by approximately 180 degrees along the first longitudinal portion, the pullwires of the second pair being angularly spaced apart by less than 180 degrees along the second longitudinal portion.

10. The apparatus of claim 9, the pullwires of the second pair being angularly spaced apart by less than 180 degrees along the third longitudinal portion.

11. The apparatus of claim 9, the pullwires of the second pair being angularly interposed between the pullwires of the first pair along the third longitudinal portion.

12. The apparatus of claim 1, the articulation assembly comprising a plurality of motors, the plurality of motors being operable to drive movement of the pullwires to thereby drive articulation of the elongate member.

13. The apparatus of claim 1, the articulation assembly being operable to drive articulation of the first longitudinal portion in at least four different directions without simultaneously driving articulation of the second longitudinal portion.

14. The apparatus of claim 1, the articulation assembly being operable to drive articulation of the first longitudinal portion in at least six different directions without simultaneously driving articulation of the second longitudinal portion.

15. The apparatus of claim 1, the articulation assembly being operable to drive articulation of the second longitudinal portion in at least four different directions without simultaneously driving articulation of the first longitudinal portion.

16. The apparatus of claim 1, the articulation assembly being operable to drive articulation of the second longitudinal portion in at least six different directions without simultaneously driving articulation of the first longitudinal portion.

17. An apparatus comprising:
(a) an elongate member comprising:
(i) a first longitudinal portion,
(ii) a second longitudinal portion proximal to the first longitudinal portion, and
(iii) a third longitudinal portion proximal to the second longitudinal portion; and
(b) a plurality of pullwires operable to drive articulation of the first longitudinal portion along two or more different articulation planes independently of the second longitudinal portion, the plurality of pullwires being further operable to drive articulation of the second longitudinal portion along two or more different articulation planes independently of the first longitudinal portion, the plurality of pullwires having a first angular arrangement relative to each other along the first longitudinal portion and a second angular arrangement relative to each other along the second longitudinal portion, the first angular arrangement being configured to distribute loads so that no bending moment is applied to the first longitudinal portion upon driving articulation of the second longitudinal portion via the plurality of pullwires, the second angular arrangement being configured to distribute loads so that no bending moment is applied to the second longitudinal portion upon driving articulation of the first longitudinal portion via the plurality of pullwires.

18. The apparatus of claim 17, wherein the second angular arrangement is different from the first angular arrangement.

19. An apparatus comprising:
(a) an elongate member comprising:
(i) a distal articulation section,
(ii) a proximal articulation section proximal to the distal articulation section, and
(iii) a shaft section proximal to the proximal articulation section; and
(b) a plurality of pullwires, the plurality of pullwires comprising a first set of pullwires and a second set of pullwires, the first set of pullwires operable to drive articulation of the distal articulation section in a first direction to thereby form a first bend along the distal articulation section, the second set of pullwires being operable to drive articulation of the proximal articulation section in a second direction to thereby form a second bend along the proximal articulation section, the first direction and the second direction being different such that the elongate member forms a double bend configuration, the first set of pullwires having a non-equal angular distribution in the distal articulation section and an equal angular distribution in the proximal articulation section, the second set of pullwires having an equal angular distribution in the distal articulation section and a non-equal angular distribution in the proximal articulation section.

20. The apparatus of claim 19, further comprising a plurality of motors configured to:
pull the first set of pullwires to drive articulation of the distal articulating section independently from the proximal articulating section, and
pull the second set of pullwires to drive articulation of the proximal articulating section independently from the distal articulating section.

* * * * *